US012558411B2

(12) United States Patent
Kim et al.

(10) Patent No.: US 12,558,411 B2
(45) Date of Patent: Feb. 24, 2026

(54) ANTIGEN COMPOSITION FOR PREVENTING OR TREATING VIRAL INFECTIOUS DISEASES

(71) Applicant: Korea University Research and Business Foundation, Sejong Campus, Sejong (KR)

(72) Inventors: Kyung Hyun Kim, Seoul (KR); Mi Sook Chung, Seoul (KR)

(73) Assignee: Korea University Research and Business Foundation, Sejong Campus, Sejong (KR)

( * ) Notice: Subject to any disclaimer, the term of this patent is extended or adjusted under 35 U.S.C. 154(b) by 701 days.

(21) Appl. No.: 17/997,703

(22) PCT Filed: Jan. 15, 2021

(86) PCT No.: PCT/KR2021/000590
§ 371 (c)(1),
(2) Date: Nov. 1, 2022

(87) PCT Pub. No.: WO2021/145720
PCT Pub. Date: Jul. 22, 2021

(65) Prior Publication Data
US 2024/0042006 A1 Feb. 8, 2024

(30) Foreign Application Priority Data

Jan. 15, 2020 (KR) ........................ 10-2020-0005553
Sep. 25, 2020 (KR) ........................ 10-2020-0124945

(51) Int. Cl.
| | |
|---|---|
| *C12N 15/86* | (2006.01) |
| *A61K 39/00* | (2006.01) |
| *A61K 39/145* | (2006.01) |
| *A61P 31/16* | (2006.01) |
| *C07K 16/00* | (2006.01) |
| *C07K 16/12* | (2006.01) |
| *C12N 9/10* | (2006.01) |
| *C12N 15/113* | (2010.01) |

(52) U.S. Cl.
CPC ............ *A61K 39/145* (2013.01); *A61K 39/00* (2013.01); *A61P 31/16* (2018.01); *A61K 2039/6031* (2013.01)

(58) Field of Classification Search
CPC .......................... C07K 16/00; C07K 2317/14; C07K 2317/24; C07K 14/005; C12N 15/86
See application file for complete search history.

(56) References Cited

FOREIGN PATENT DOCUMENTS

| | | | |
|---|---|---|---|
| JP | 2015-501141 A | 1/2015 |
| KR | 10-2018-0054091 A | 5/2018 |
| KR | 10-1921384 B1 | 11/2018 |

OTHER PUBLICATIONS

Gali, Himabindu, et al. "Role of SUMO modification of human PCNA at stalled replication fork." *Nucleic acids research* 40.13 (2012): 6049-6059.
Lu, Yuan, John P. Welsh, and James R. Swartz. "Production and stabilization of the trimeric influenza hemagglutinin stem domain for potentially broadly protective influenza vaccines." *Proceedings of the National Academy of Sciences* 111.1 (2014): 125-130.
Lee, Ji-Hye et al., "Development of next-generation universal vaccine to control viral infectious diseases" *Science On*, 2016.
International Search Report issued on May 11, 2021, in counterpart PCT/KR2021/000590 (4 pages in Korean).
Korean Decision of Grant issued on Jun. 16, 2021 in corresponding Korean Patent Application No. 10-2020-0005553 (3 pages in Korean).
Korean Office Action issued on Oct. 17, 2022 in corresponding Korean Patent Application No. 10-2020-0124945 (5 pages in Korean).

*Primary Examiner* — Barry A Chestnut
(74) *Attorney, Agent, or Firm* — NSIP Law

(57) ABSTRACT

The present invention relates to an antigen composition for preventing or treating viral infectious diseases, comprising, as an active ingredient, a multiple variant protein of a recombinant hemagglutinin monomeric protein in an influenza virus. In addition, the present invention relates to an antigen composition for preventing or treating viral infectious diseases, comprising a scaffold-based fusion protein. The antigen composition for preventing or treating viral infectious diseases, according to the present invention, has an outstanding preventive effect of inhibiting the proliferation and replication of viruses having various mutations, and is recyclable and safe by means of using a recombinant protein, and thus can be widely used in various industrial fields, such as the medicine and life science fields.

12 Claims, 37 Drawing Sheets

Specification includes a Sequence Listing.

【Fig.1A】
A
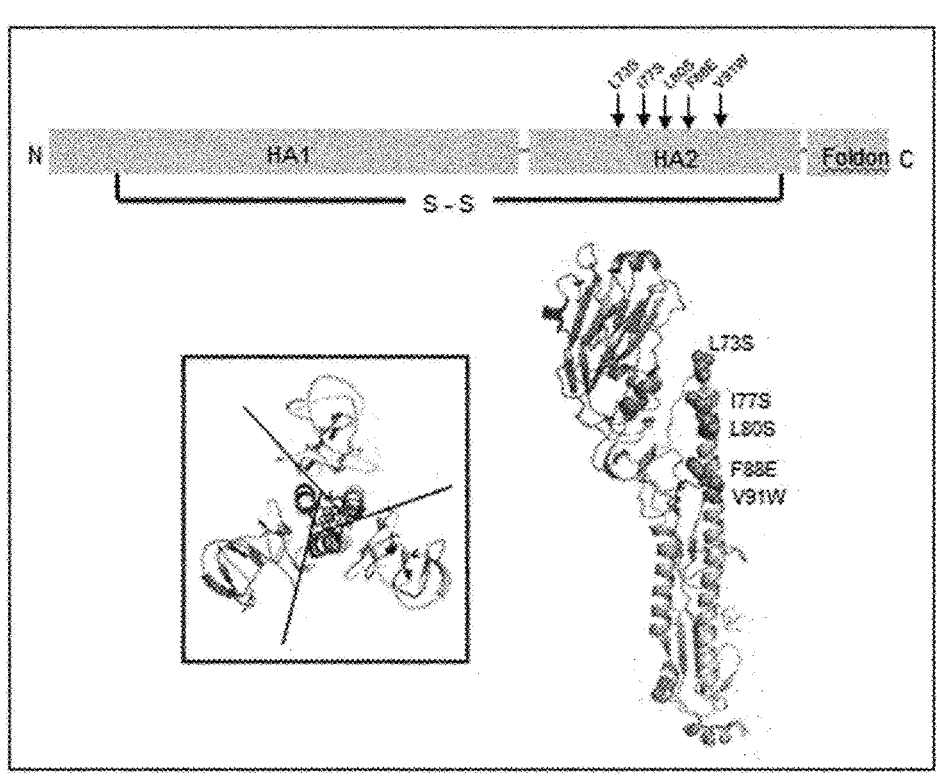
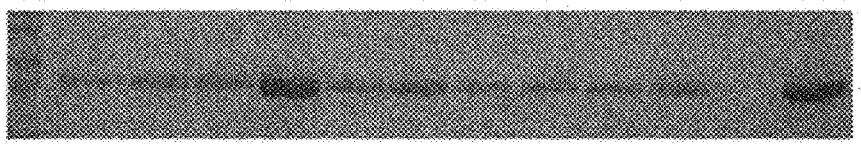
| HA subtypes | Mutant site |
|---|---|
| H1 HA<br>A/California/04/2009(CA04) | L73S/I77S/L80S/F88E/V91W<br>V20C-E105C/M320C-H111C |
| H3 HA<br>A/Gyeongnam/684/2006 (Gy684) | V73S/I77S/L80S/V84W/L91W<br>M320C-T111C |
| B HA<br>B/Florida/4/2006 (FL04) | L73S/I77S/L80W/V84W/L87S/<br>T91W/L98S/L102W |

MSYYHHHHHHDYDIPTTENLYFQGAMDMLLVNQSHQGFNKEHTSKMVSAIVLYVLLAAAAHSAFA
ADPGDTLCIGYHANNSTDTVDTCLEKNVTVTHSVNLLEDKHNGKLCKLRGVAPLHLGKCNIAGWILG
NPECESLSTASSWSYIVETPSSDNGTCYPGDFIDYEELREQLSSVSSFERFEIFPKTSSWPNHDSNKGVT
AACPHAGAKSFYKNLIWLVKKGNSYPKLSKSYINDKGKEVLVLWGIHHPSTSADQQSLYQNADAYVFV
GSSRYSKKFKPEIAIRPKVRDQEGRMNYYWTLVEPGDKITFEATGNLVVPRYAFAMERNAGSGIIISDTP
VHDCNTTCQTPKGAINTSLPFQNIHPITIGKCPKYVKSTKLRLATGCRNIPSIQSRGLFGAIAGFIEGGWT
GMVDGWYGYHHQNEQGSGYAADLKSTQNAIDEITNKVNSVIEKMNTQFTAVGKEFNHSEKRSENS
NKKVDDGELDWWTYNAELLVLLENCRTLDYCDSNVKNLYEKVRSQLKNNAKEIGNGCFEFYHKCDN
TCMESVKNGTYDYPKYSEEAKLNREEIDGVSGRLVPRGSPGSGYIPEAPRDGQAYVRKDGEWVLLSTFL
GHHHHHH

H3 HA_5m_DS

MSYYHHHHHHDYDIPTTENLYFQGAMDMLLVNQSHQGFNKEHTSKMVSAIVLYVLLAAAAHSAFA
ADPGATLCLGHHAVQNGTIVKTITNDQIEVTNATELVQNSSTGGICDSPHQILDGENCTLIDALLGDP
QCDGFQNKKWDLFVERSKAYSNCYPYDVPDYASLRSLVASSGTLEFNNESFNWTGVTQNGTSSACK
RGSNNSFFSRLNWLTHSKFKYPALNVTMPNNEEFDKLYIWGVHHPGTDNDQIFLYAQASGRITVSTK
RSQQTVIPNIGSRPRVRDIPSRISIYWTIVKPGDILLINSTGNLIAPRGYFKIRSGKSSIMRSDAPIGKCNSE
CITPNGSIPNDKPFQNVNRITYGACPRYVKQNTLKLATGCRNVPEKQTRGIFGAIAGFIENGWEGMV
DGWYGFRHQNSEGIGQAADLKSTQAAIDQINGKLNRLIGKTNEKFHQIEKEFSESEGRSQDSEKYWE
DTKIDWWSYNAELLVALENQHTIDLCDSEMNKLFEKTKKQLRENAEDMGNGCFKIYHKCDNACIGSI
RNGTYDHDVYRDEALNNRFQIKGLSGRLVPRGSPGSGYIPEAPRDGQAYVRKDGEWVLLSTFLGHH
HHHH

B HA_8m

MSYYHHHHHHDYDIPTTENLYFQGAMDPEFKGLMLLVNQSHQGFNKEHTSKMVSAIVLYVLLAAA
AHSAFAADPGYLLEFDRICTGITSSNSPHVVKTATQGEVNVTGVIPLTTTPTKSYFANLKGTRTRGKLCP
DCLNCTDLDVALGRPMCVGTTPSAKASILHEVRPVTSGCFPIMHDRTKIRQLPNLLRGYENIRLSTQN
VIDAEKAPGGPYRLGTSGSCPNATSKIGFFATMAWAVPKDNYKNATNPLTVEVPYICTEGEDQITVW
GFHSDNKTQMKNLYGDSNPQKFTSSANGVTTHYVSQIGDFPDQTEDGGLPQSGRIVVDYMMQKP
GKTGTIVYQRGVLLPQKVWCASGRSKVIKGSLPLIGEADCLHEKYGGLNKSKPYYTGEHAKAIGNCPI
WVKTPLKLANGTKYRPPAKLLKERGFFGAIAGFLEGGWEGMIAGWHGYTSHGAHGVAVAADLKSTQ
EAINKITKNLNSLSELEVKNLQRLSGAMDESHNESLEWDEKWDDSRADWISSQIESAVLWSNEGIINS
EDEHLLALERKLKKMLGPSAVDIGNGCFETKHKCNQTCLDRIAAGTFNAGEFSLPTFDSSGRLVPRGSP
GSGYIPEAPRDGQAYVRKDGEWVLLSTFLGHHHHHH

【Fig.1C】
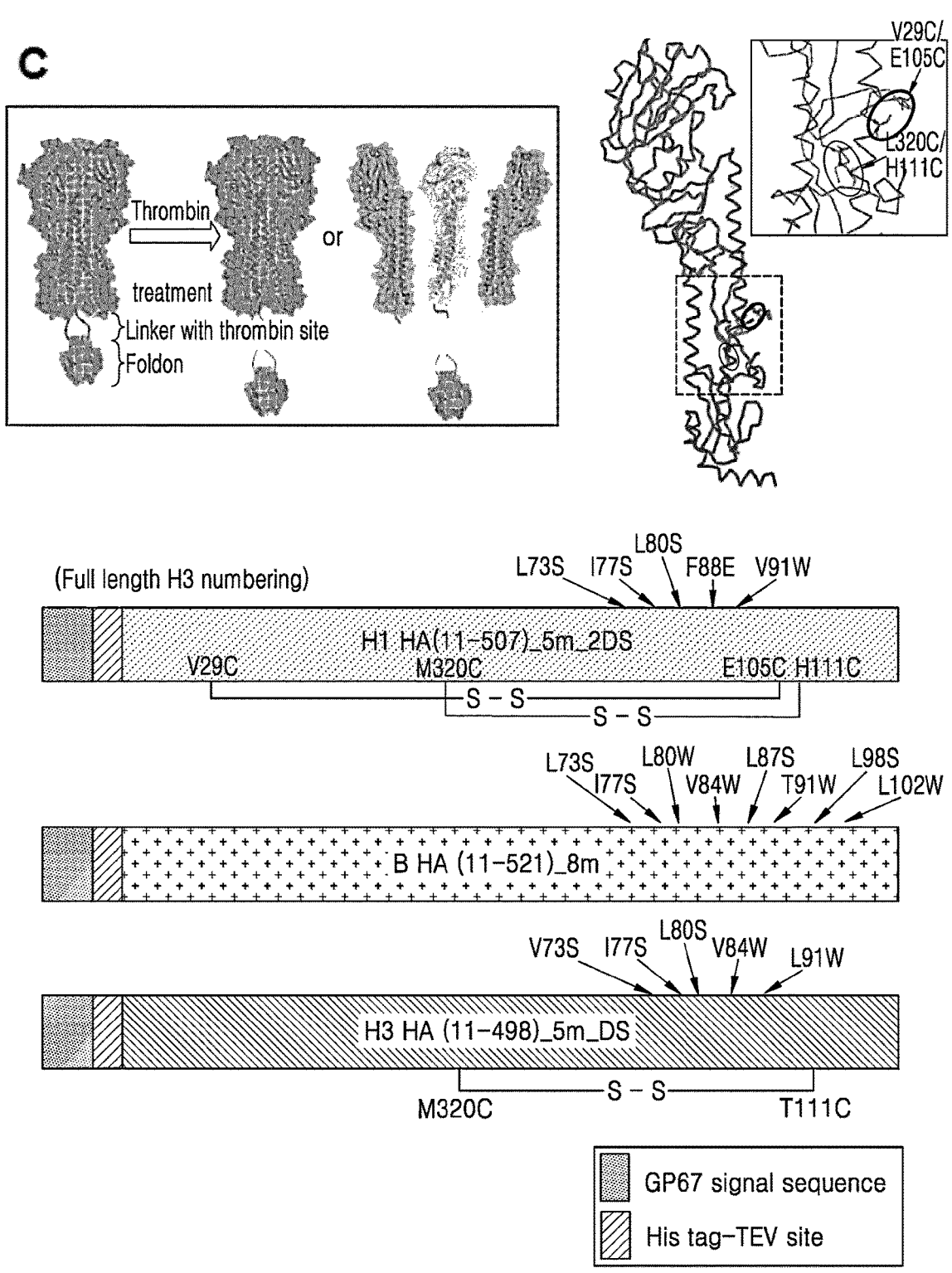

【Fig.2A】
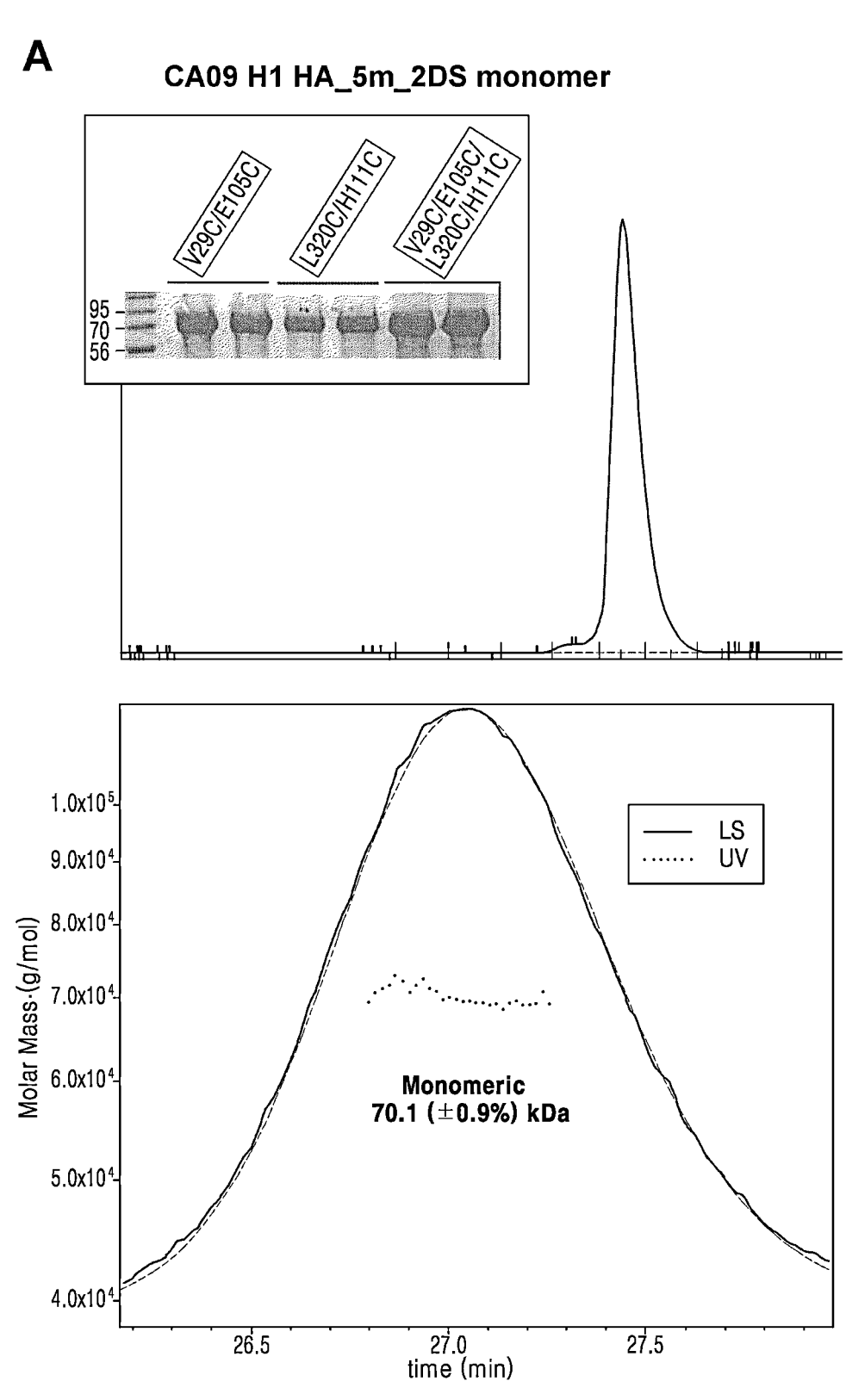
A
CA09 H1 HA_5m_2DS monomer

【Fig.2B】
B
Gy684 H3 HA_5m_DS monomer
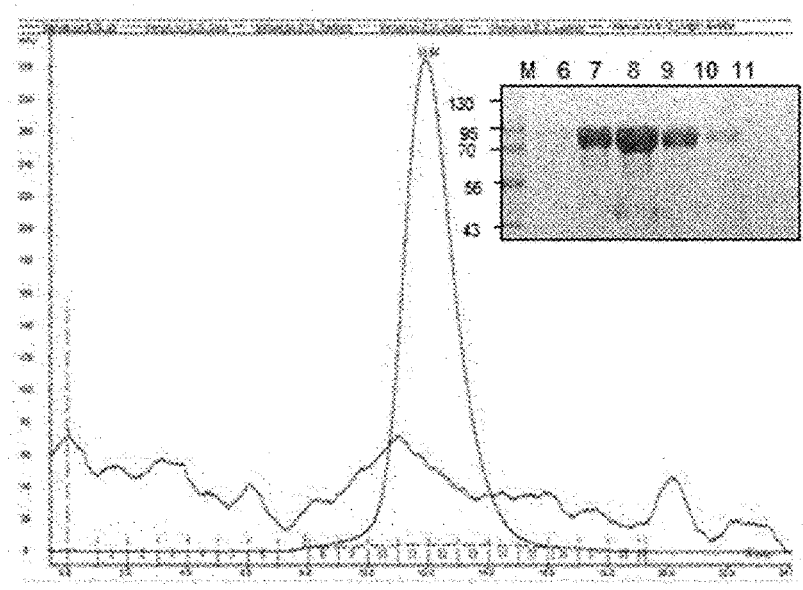
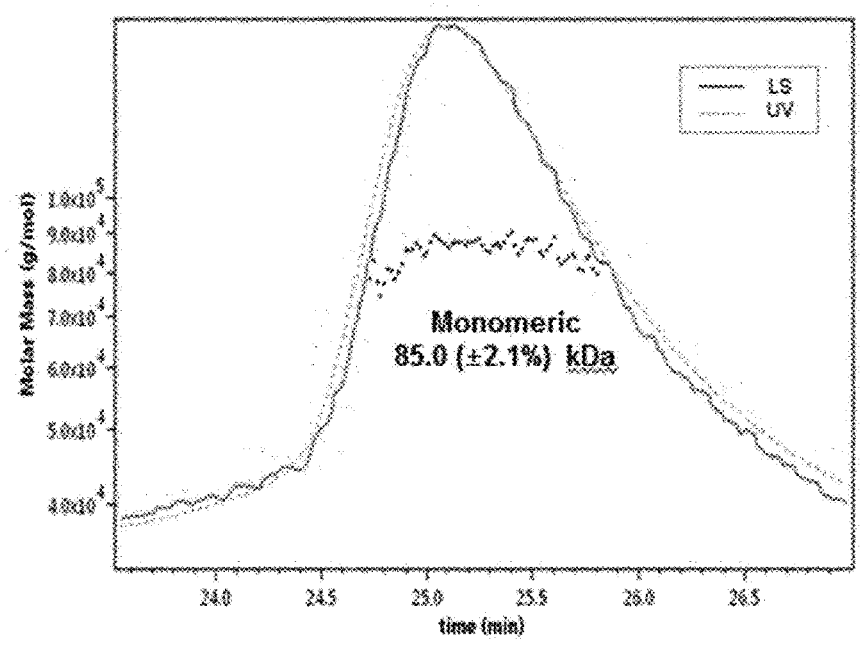

【Fig.2C】
C
FL04 B HA_8m monomer
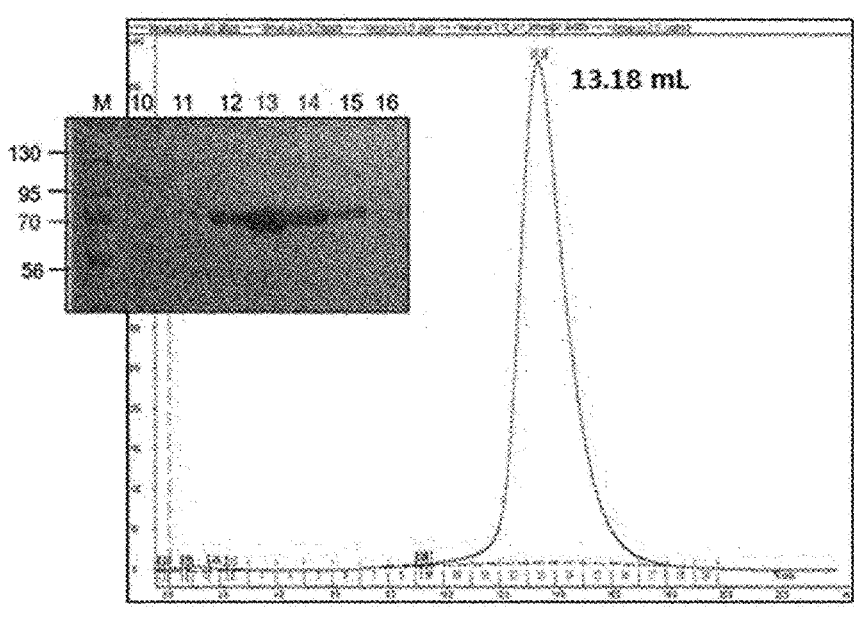
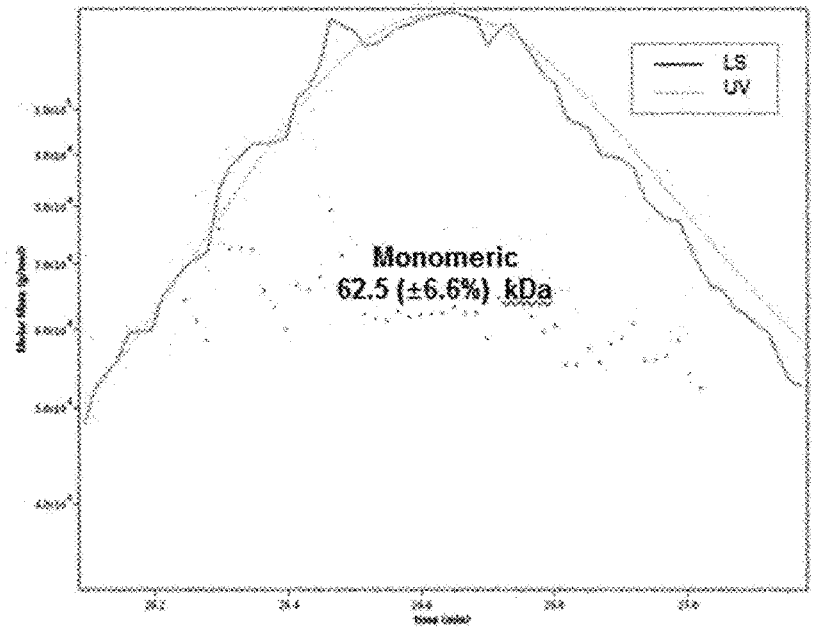

【Fig.3A】
A
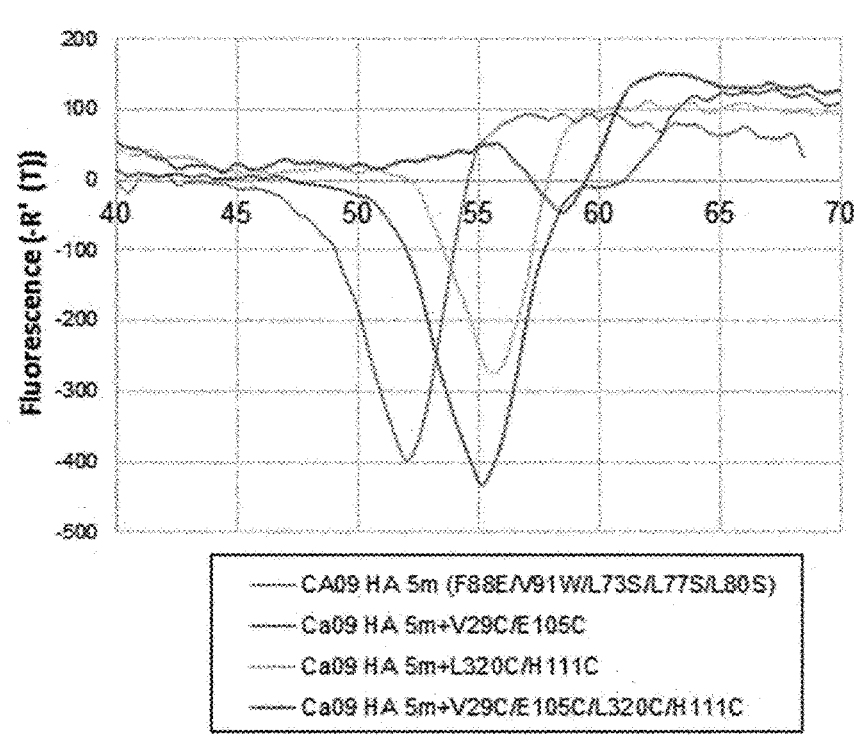
- CA09 HA 5m (F88E/V91W/L73S/L77S/L80S)
- Ca09 HA 5m+V29C/E105C
- Ca09 HA 5m+L320C/H111C
- Ca09 HA 5m+V29C/E105C/L320C/H111C
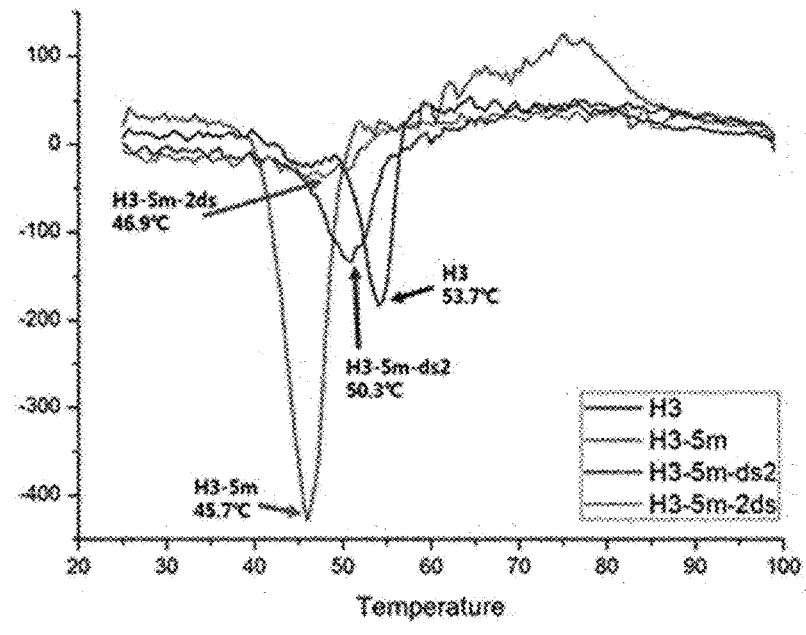
- H3
- H3-5m
- H3-5m-ds2
- H3-5m-2ds 【Fig.3B】
B
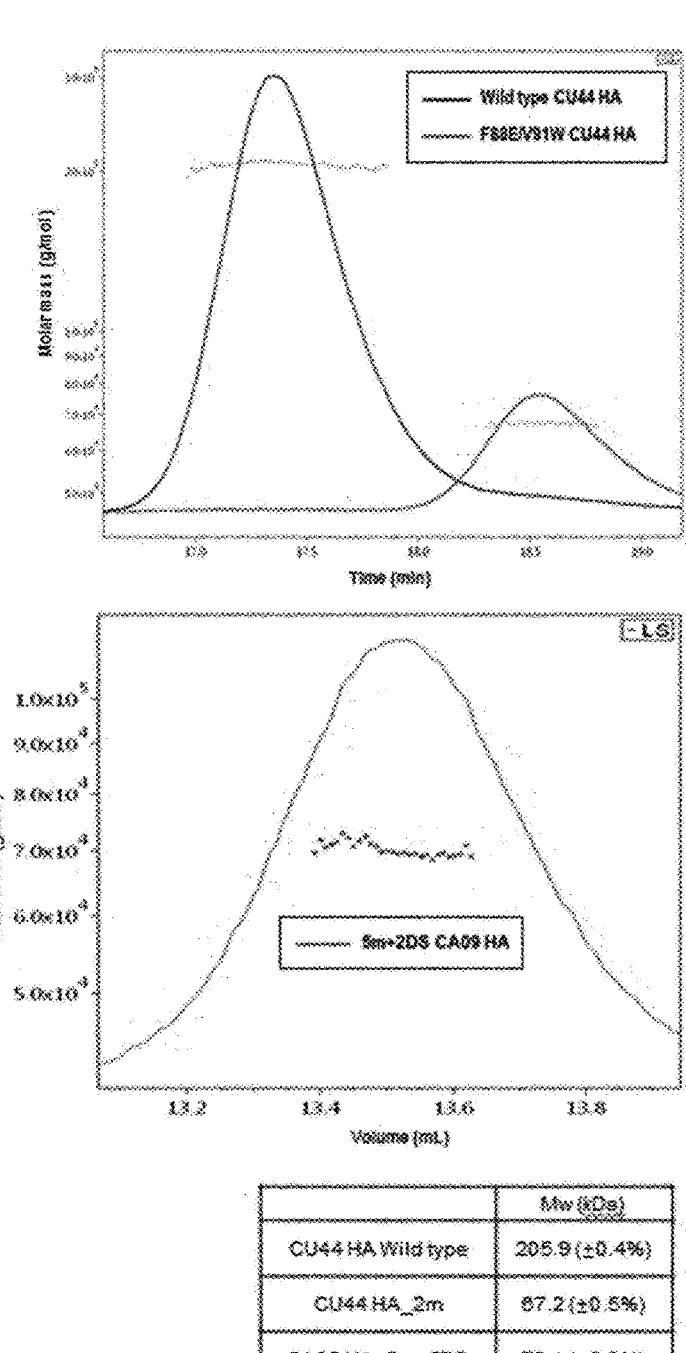
| | Mw (kDa) |
|---|---|
| CU44 HA Wild type | 205.9 (±0.4%) |
| CU44 HA_2m | 87.2 (±0.5%) |
| CA09 HA_5m_2DS | 70.1 (±0.9%) |

【Fig.3C】
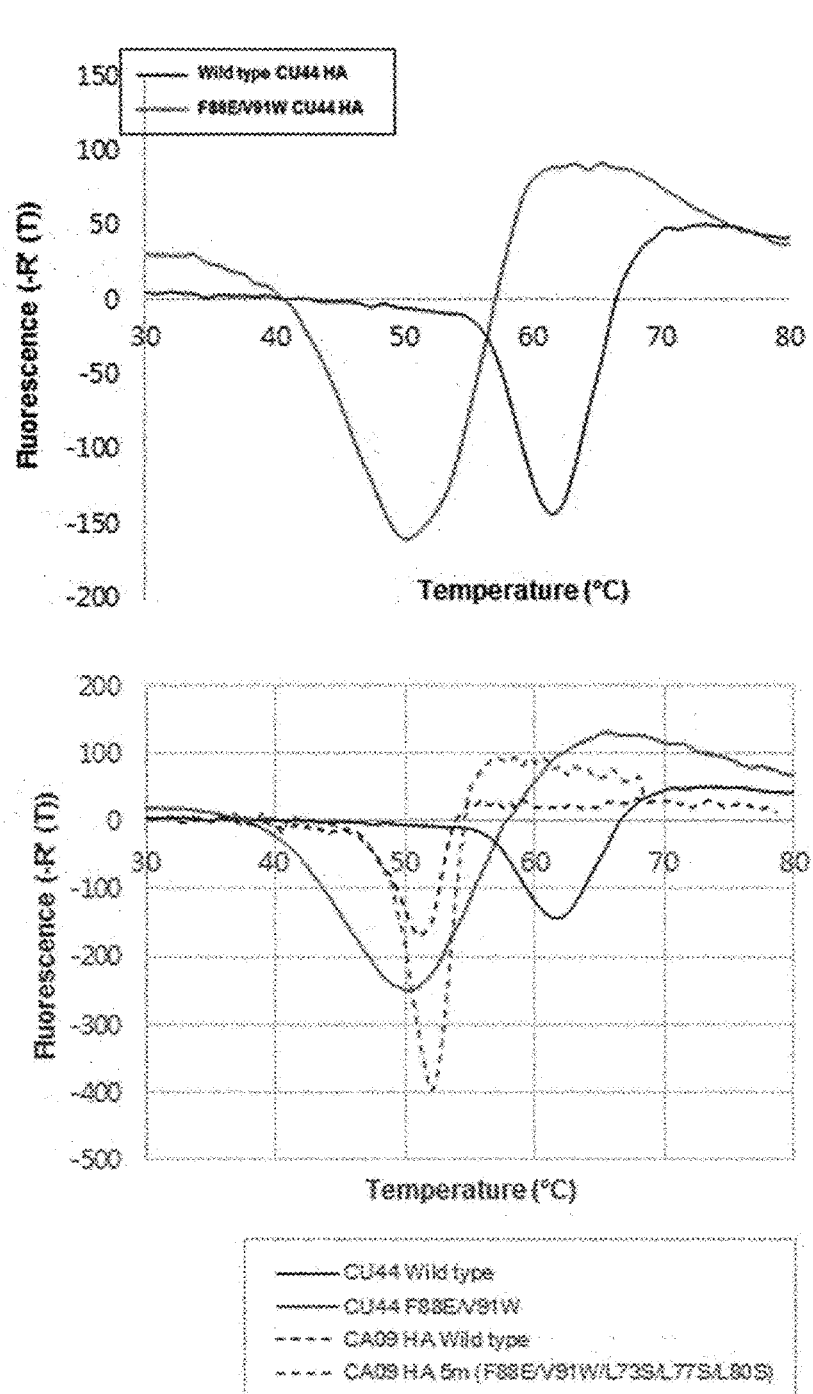

【Fig.4】
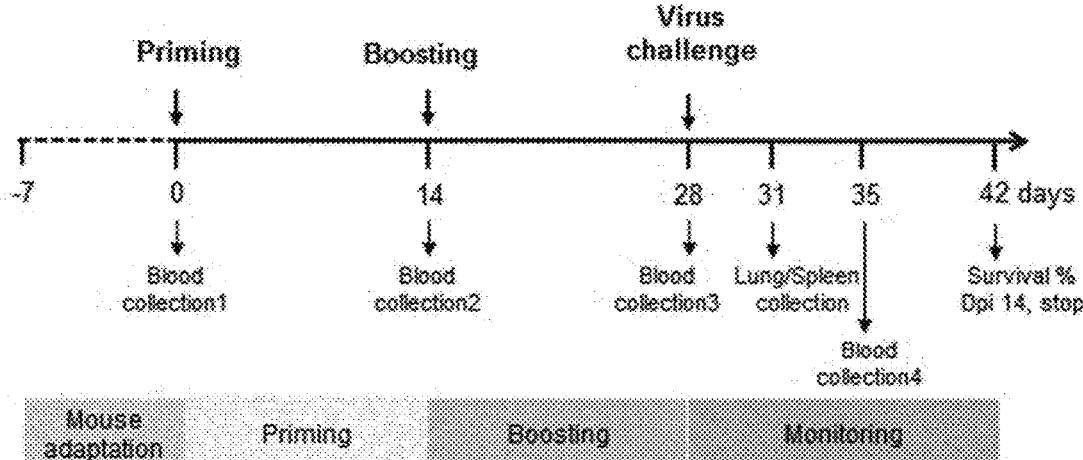
Female BALB/c mice, 6 wk
| | Mouse group | No. of mouse (total 36) |
|---|---|---|
| 1 | Naive (no vaccine, no virus) | 4 |
| 2 | PBS buffer + adjuvant | 8 |
| 3 | H1(CA09) HA monomer + adjuvant | 8 |
| 4 | Commercial SK bioscience trivalent vaccine | 8 |
| 5 | H1 HA, B HA, H3 HA mutant monomer mixture + adjuvant | 8 |

【Fig.5】
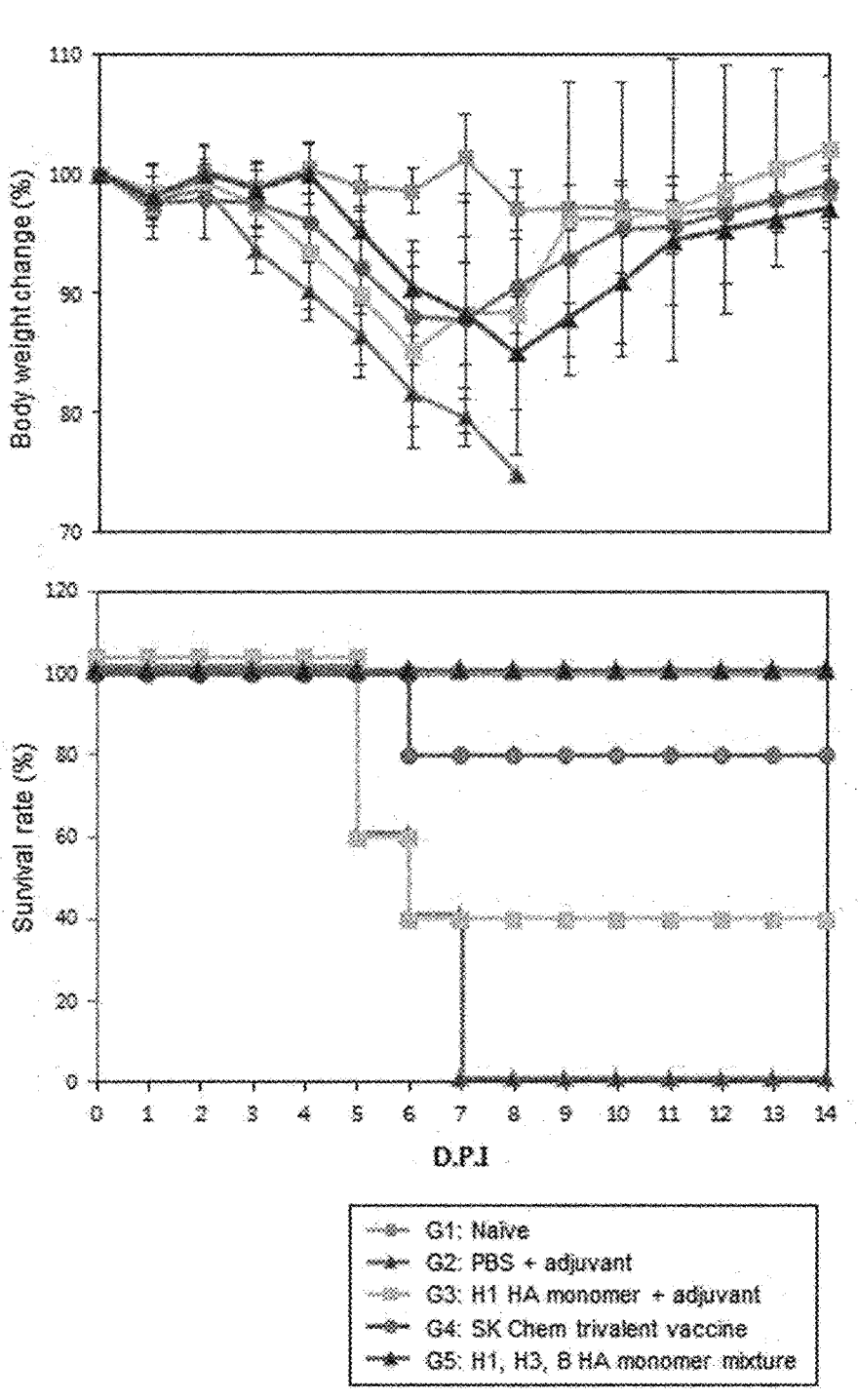

【Fig.6】
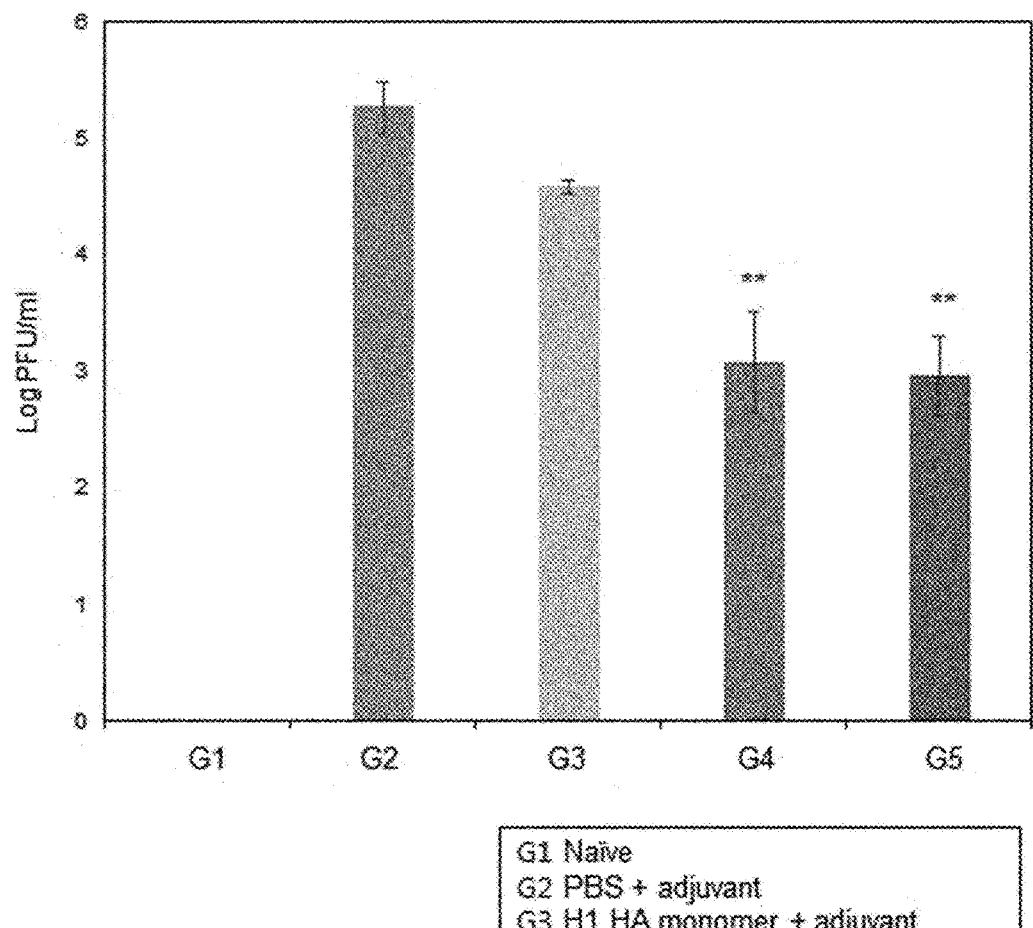
G1 Naïve
G2 PBS + adjuvant
G3 H1 HA monomer + adjuvant
G4 SK Chem trivalent vaccine
G5 H1, H3, B HA monomer mixture 【Fig.7】
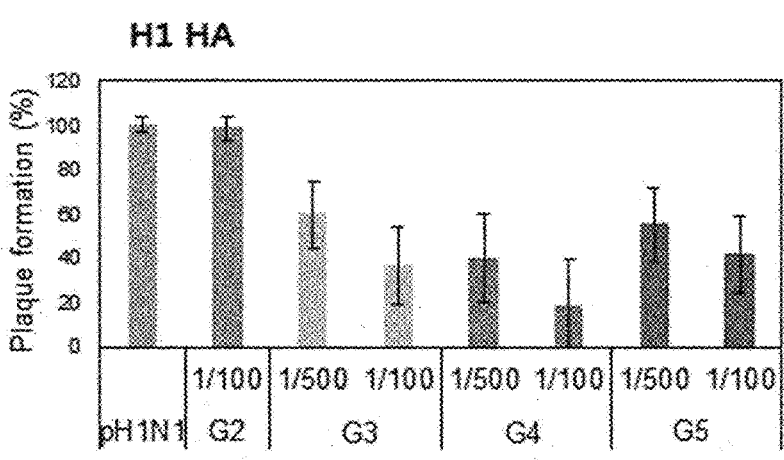
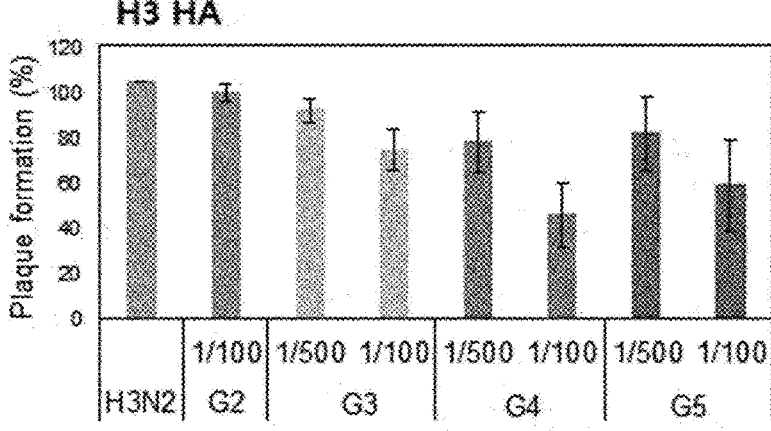
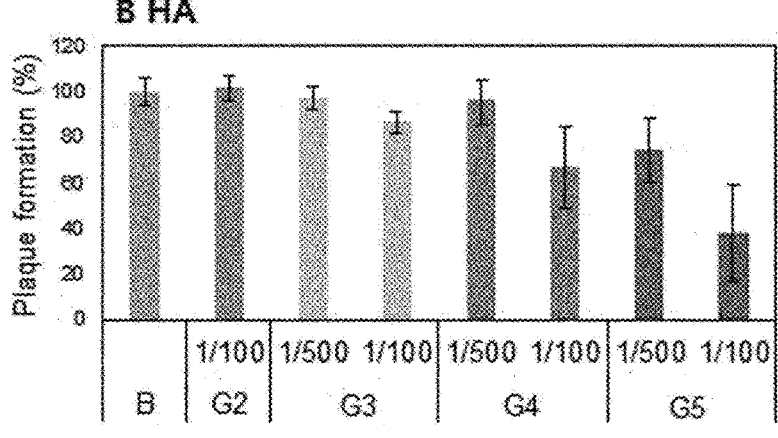

【Fig.8A】
A
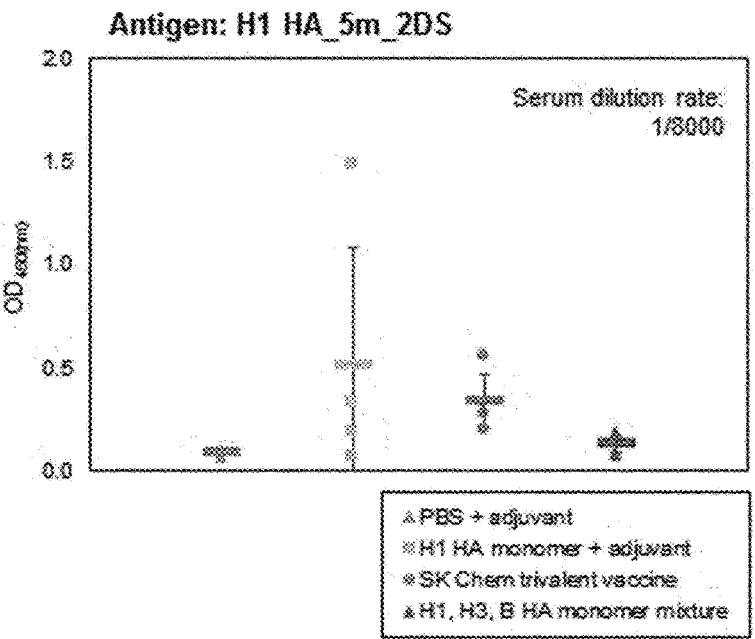
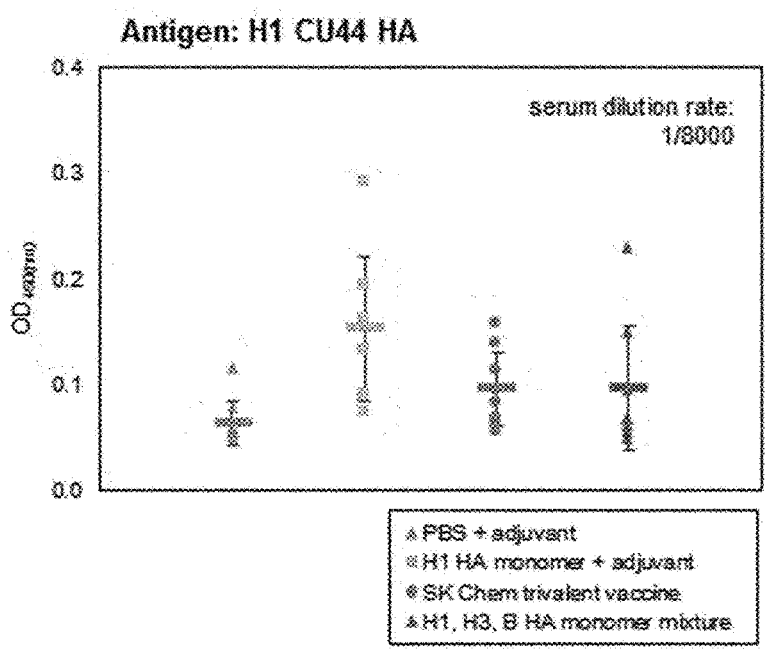

【Fig.8B】
B
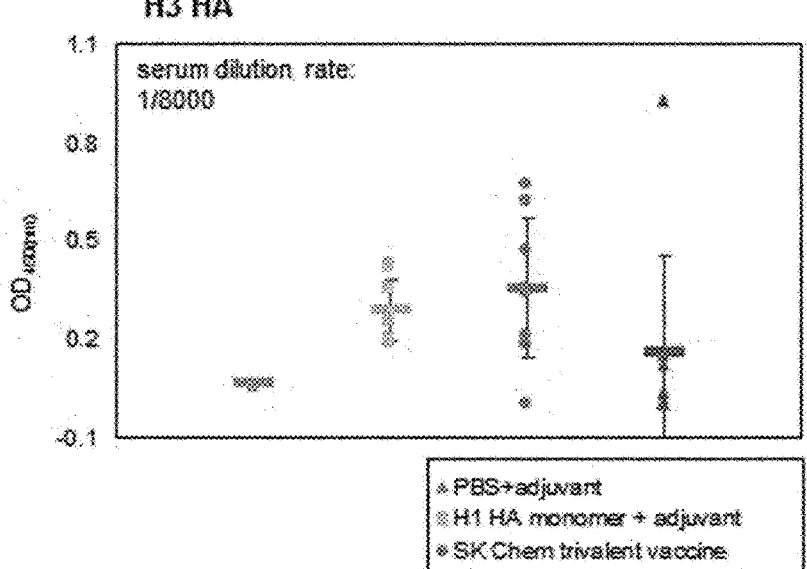
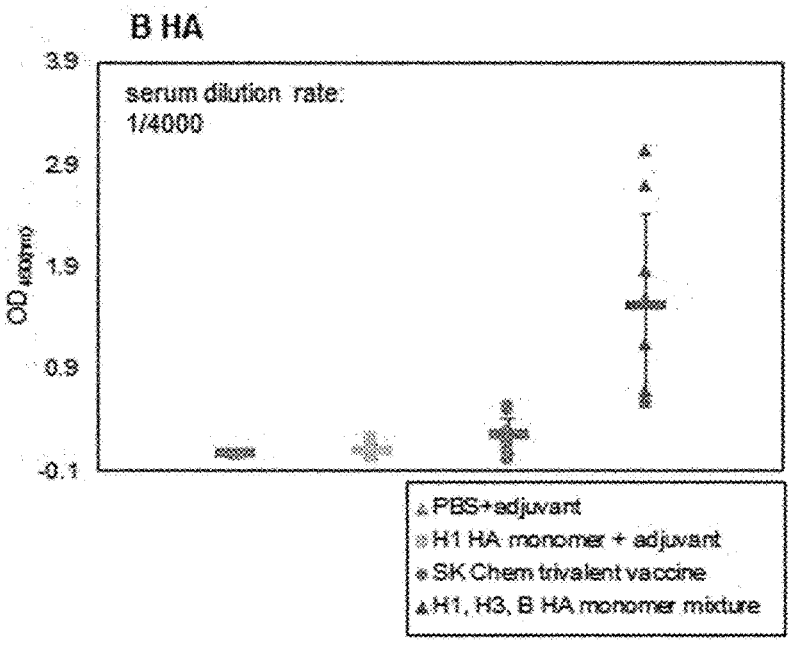

【Fig.8C】
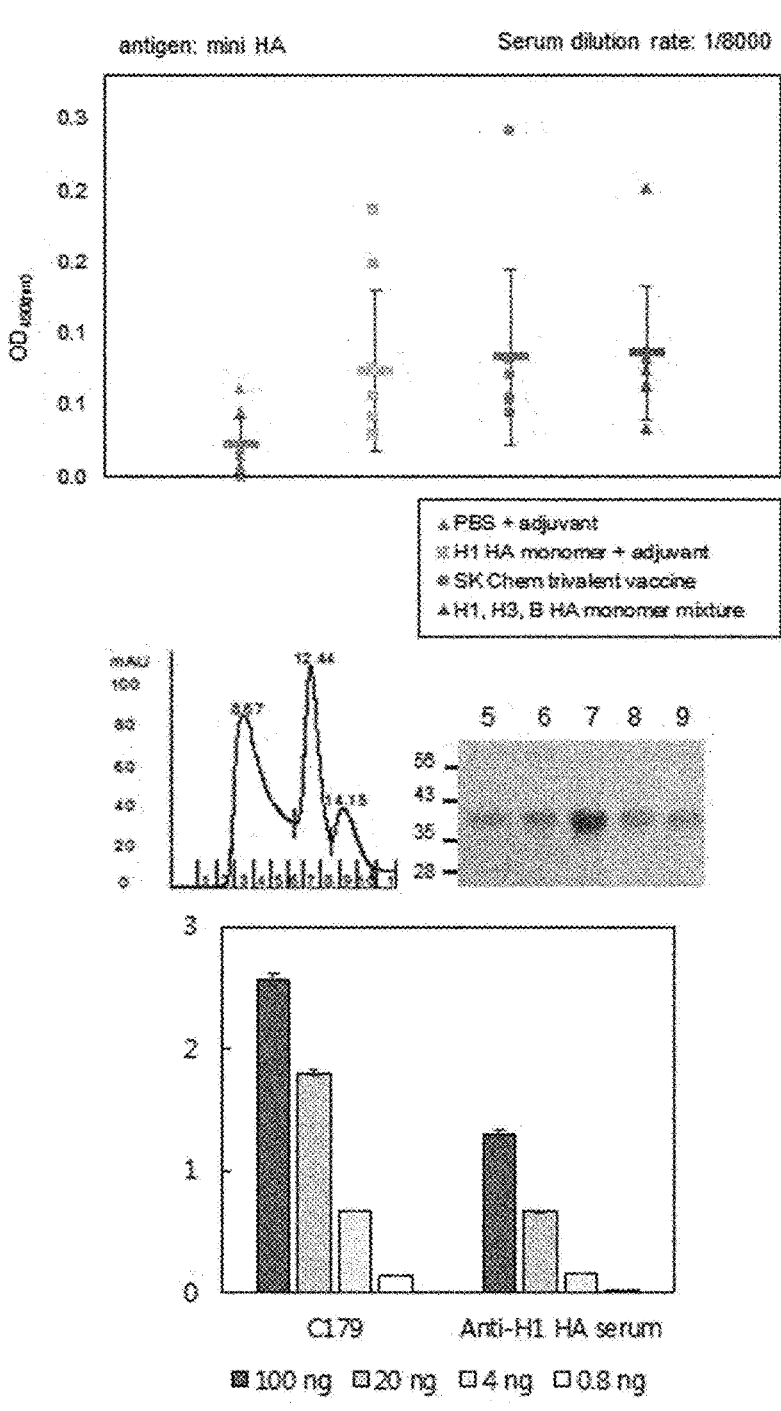

【Fig.9】
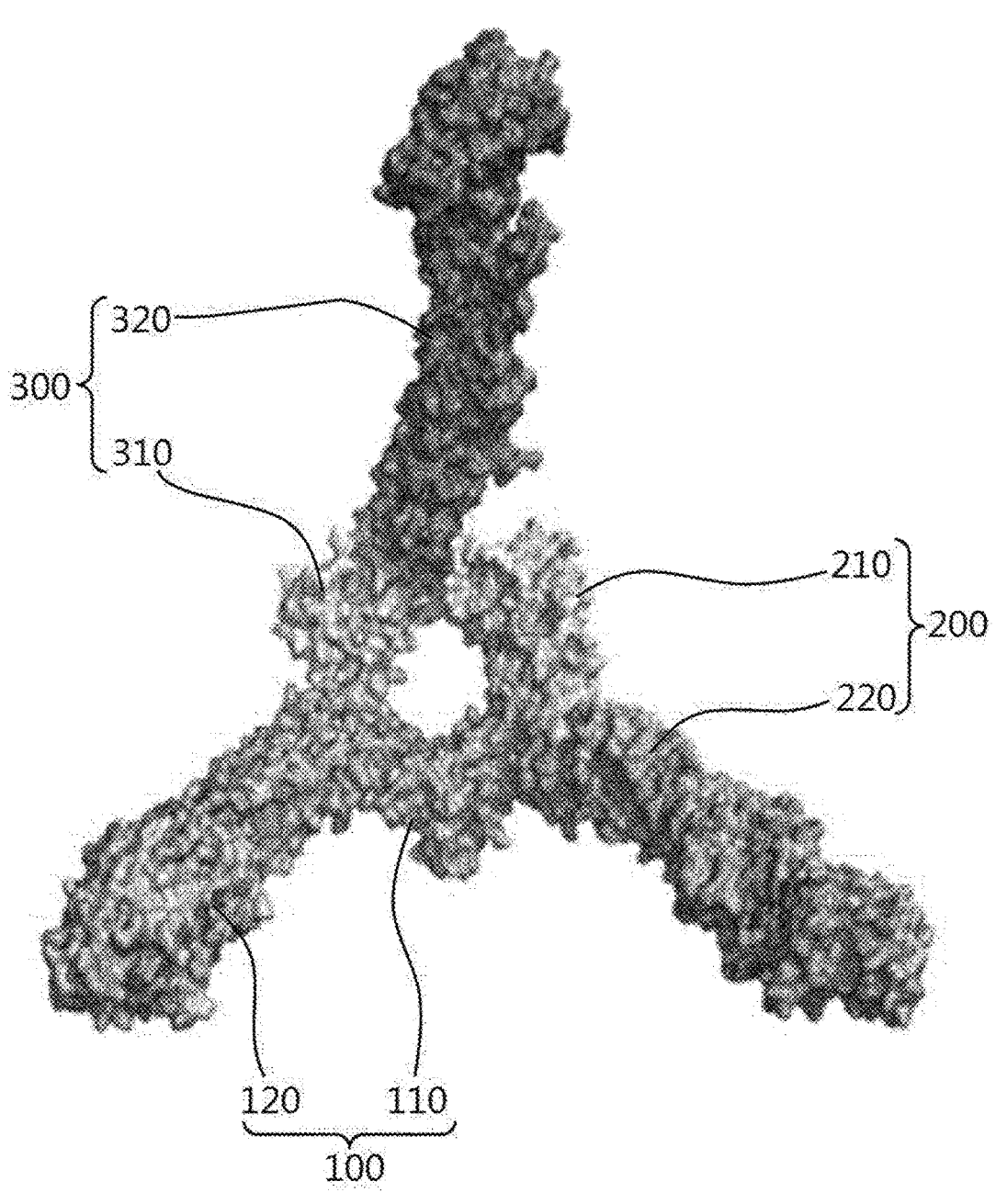

【Fig.10A】
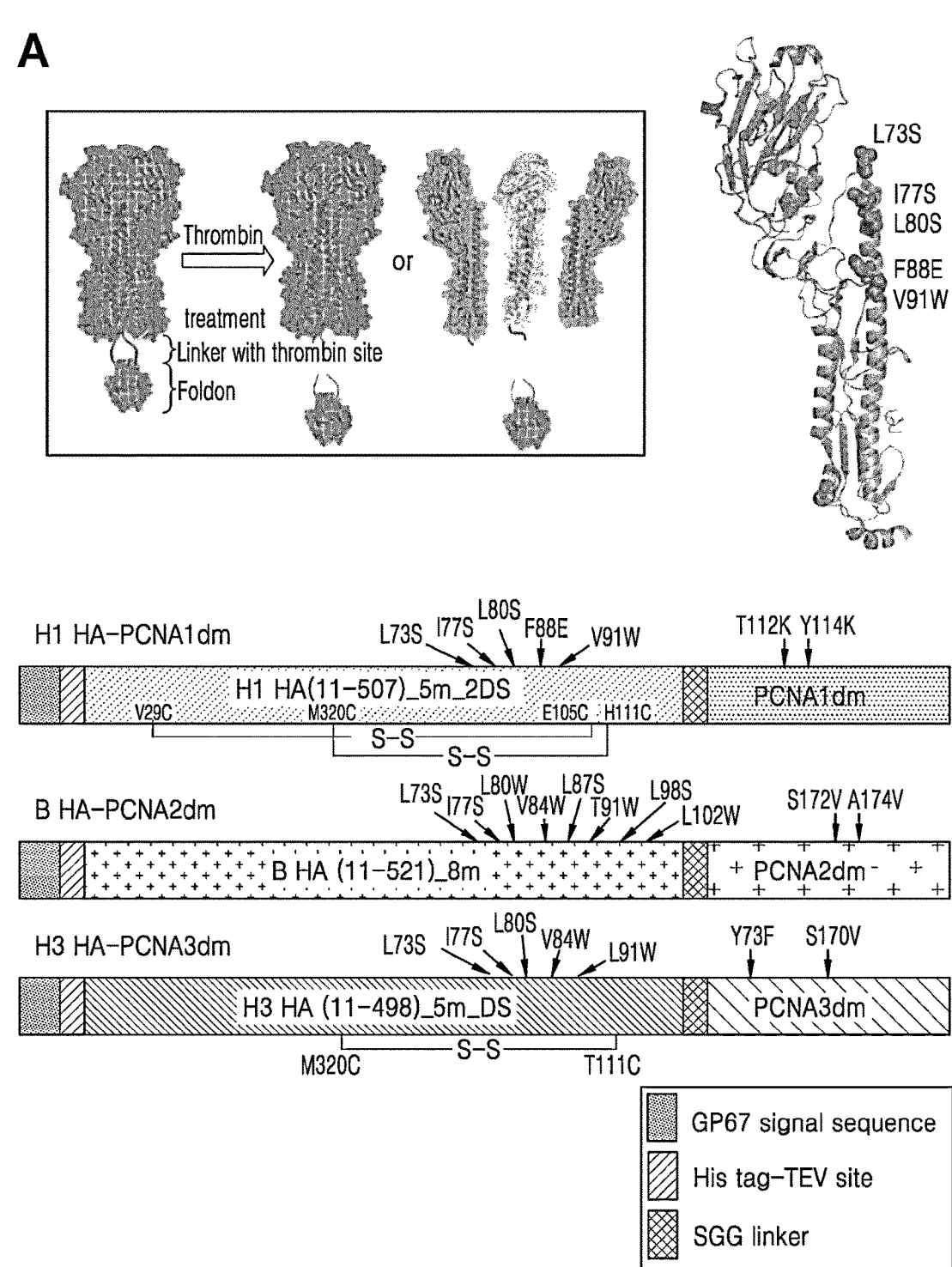

| HA subtypes | Mutant site |
|---|---|
| H1 HA<br>A/California/04/2009(CA04) | L73S/I77S/L80S/F88E/V91W<br>V20C-E105C/M320C-H111C |
| H3 HA<br>A/Gyeongnam/684/2006 (Gy684) | V73S/I77S/L80S/V84W/L91W<br>M320C-T111C |
| B HA<br>B/Florida/4/2006 (FL04) | L73S/I77S/L80W/V84W/L87S/<br>T91W/L98S/L102W |

H1_HA_5m_2DS

```
MSYYHHHHHHDYDIPTTENLYFQGAMDMLLVNQSHQGFNKEHTSKMVSAIVLYVLLAAAAHSAFAADPGDTL
CIGYHANNSTDTVDTCLEKNVTVTHSVNLLEDKHNGKLCKLRGVAPLHLGKCNIAGWILGNPECESLSTASS
WSYIVETPSSDNGTCYPGDFIDYEELREQLSSVSSFERFEIFPKTSSWPNHDSNKGVTAACPHAGAKSFYKN
LIWLVKKGNSYPKLSKSYINDKGKEVLVLWGIHHPSTSADQQSLYQNADAYVFVGSSRYSKKFKPEIAIRPK
VRDQEGRMNYYWTLVEPGDKITFEATGNLVVPRYAFAMERNAGSGIIISDTPVHDCNTTCQTPKGAINTSLP
FQNIHPITIGKCPRYVKSTKLRLATGCRNIPSIQSRGLFGAIAGFIEGGWTGMVDGWYGYHHQNEQGSGYAA
DLKSTQNAIDEITNKVNSVIERMNTQFTAVGKEFNHSEKRSENSNKKVDDGFLDWWTYNAELLVLLENCRTL
DYCDSNVKNLYEKVRSQLKNNAKEIGNGCFEFYHKCDNTCMESVKNGTYDYPKYSEEAKLNREEIDGVSGRL
VPRGSPGSGYIPEAPRDGQAYVRKDGEWVLLSTFLGHHHHHH
```

H3_HA_5m_DS

```
MSYYHHHHHHDYDIPTTENLYFQGAMDMLLVNQSHQGFNKEHTSKMVSAIVLYVLLAAAAHSAFAADPGATL
CLGRHAVQNGTIVKTITNDQIEVTNATELVQNSSTGGICDSPHQILDGENCTLIDALLGDPQCDGFQNKKWD
LFVERSKAYSNCYPYDVPDYASLRSLVASSGTLEFNNESFNWTGVTQNGTSSACKRGSNNSFFSRLNWLTHS
KFKYPALNVTMPNNEEFDKLYIWGVHHPGTDNDQIFLYAQASGRITVSTKRSQQTVIPNIGSRPRVRDIPSR
ISIYWTIVKPGDILLINSTGNLIAPRGYFKIRSGKSSIMRSDAPIGKCNSECITPNGSIPNDKPFQNVNRIT
YGACPRYVKQNTLKLATGCRNVPEKQTRGIFGAIAGFIENGWEGMVDGWYGFRHQNSEGIGQAADLKSTQAA
IDQINGKLNRLIGKTNEKFHQIEKEFSESEGRSQDSEKYWKDTKIIWWSYNAELLVALENQHTIDLCDSEMN
KLFERTKKQLRENAEDMGNGCFKIYHKCDNACIGSIRNGTYDHDVYRDEALNNRFQIKGLSGRLVPRGSPGS
GYIPEAPRDGQAYVRKDGEWVLLSTFLGHHHHHH
```

B_HA_8m

```
MSYYHHHHHHDYDIPTTENLYFQGAMDPEFKGLMLLVNQSHQGFNKEHTSKMVSAIVLYVLLAAAAHSAFAA
DPGYLLEFDRICTGITSSNSPHVVKTATQGEVNVTGVIPLTTTPTKSYFANLKGTRTRGKLCPDCLNCTDLD
VALGRPMCVGTTPSAKASILHEVRPVTSGCFPIMHDRTKIRQLPNLLRGYENIRLSTQNVIDAEKAPGGPYR
LGTSGSCPNATSKIGFFATMAWAVPKDNYKNATNPLTVEVPYICTEGEDQITVWGFHSDNKTQMKNLYGDSN
PQKFTSSANGVTTHYVSQIGDFPDQTEDGGLPQSGRIVVDYMMQKPGKTGTIVYQRGVLLPQKVWCASGRSK
VIKGSLPLIGEADCLHEKYGGLNKSKPYYTGEHAKAIGNCPIWVKTPLKLANGTKYRPPAKLLKERGFFGAI
AGFLEGGWEGMIAGWHGYTSHGAHGVAVAADLKSTQEAINKITKNLNSLSELEVKNLQRLSGAMDESHNESL
EWDEKWDDSRADWISSQIESAVLWSNEGIINSEDEHLLALERKLKKMLGPSAVDIGNGCFETRHKCNQTCLD
RIAAGTFNAGEFSLPTFDSSGRLVPRGSPGSGYIPEAPRDGQAYVRKDGEWVLLSTFLGHHHHHH
```

【Fig.10C】

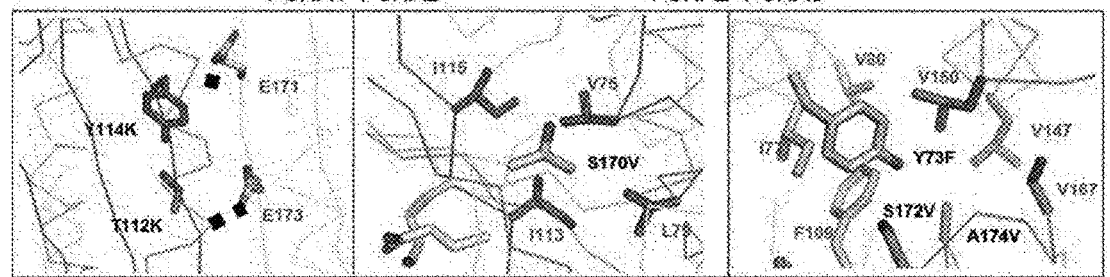

C

| Proteins | Remarks |
|---|---|
| PCNA1 | Wild type |
| PCNA2 | Wild type |
| PCNA3 | Wild type |
| PCNA1dm | T112K/Y114K double mutant |
| PCNA2dm | S172V/A174V double mutant |
| PCNA3dm | Y73F/S170V double mutant |

PCNA1~PCNA2                    PCNA2~PCNA3

PCNA1dm

>ORF sequence | 249 aa

```
MFKIVYPNARDFFSFINSITNVTDSIILNFTEDGIFSRHLTEDKVLMAIMRIPKDVLSEY   60
SIDSPTSVKLDVSSVKKILSKASSKKATIELTETDSGLKIIIRDEKSGAKSKIKIKAEKG  120
QVEQLTEPKVNLAVNFTTDESVLNVIAADVTLVGEEMRISTEEDKIKIEAGEEGKRYVAF  180
LMKDKPLKELSIDTSASSSYSAEMFKDAVKGLRGFSAPTMVSFGENLPMKIDVEAVSGGH  240
MIFWIAPRL  249
```

PCNA2dm

>ORF sequence | 266 aa

```
MGSSHHHHHHSSGLVPRGSHMMKAKVIDAVSFSYILRTVGDFLSEANFIVTKEGIRVSGI   60
DPSRVVFLDIFLPSSYFEGFEVSQEREIIGFKLEDVNDILKRVLKDDTLILSSNESKLTL  120
TFDGEFTRSFELPLIQVESTQPPSVNLEFPFKAQLLTITFADIIDELSDLGEVLNIHSKE  180
NKLYFEVIGDLVTVKVELSTDNGTLLEASGADVSSSYGMEYVANTTKMRRASDSMELYFG  240
SQIPLKLRFKLPQEGYGDFYIAPRAD  266
```

PCNA3dm

>ORF sequence | 273 aa

```
MGSSHHHHHHSQDPMIYLKSFERNIRLINMKVVYDDVRVLKDIIQALARLVDEAVLKFKQ   60
DSVELVALDRAHISLISVNLPREMFKEYDVNDEFKFGFNTQFLMKILKVAKRKEAIEIAS  120
ESPDSVIINIIGSTNREFNVRNLEVSEQEIPEINLQFDISATISSDGFKSAISEVSTVTD  180
NVVVEGHEDRILIKAEGEVEVEVEFSKDTGGLQDLEFSKESKNSYSAEYLDDVLSLTKLS  240
DYVKISFGNQKPLQLFFNMEGGGKVTYLLAPKV  273
```

【Fig.11A】
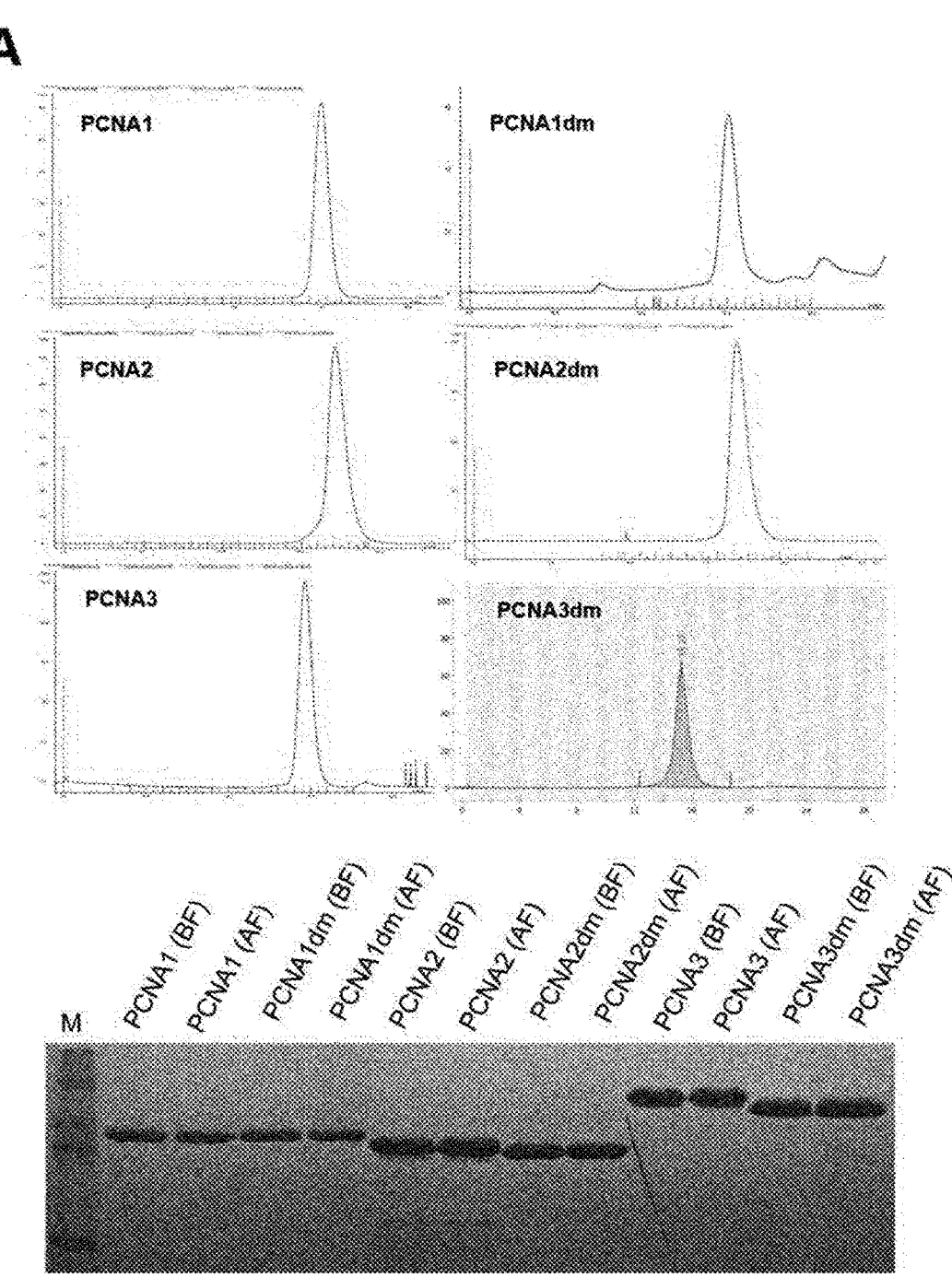

【Fig.11B】
B
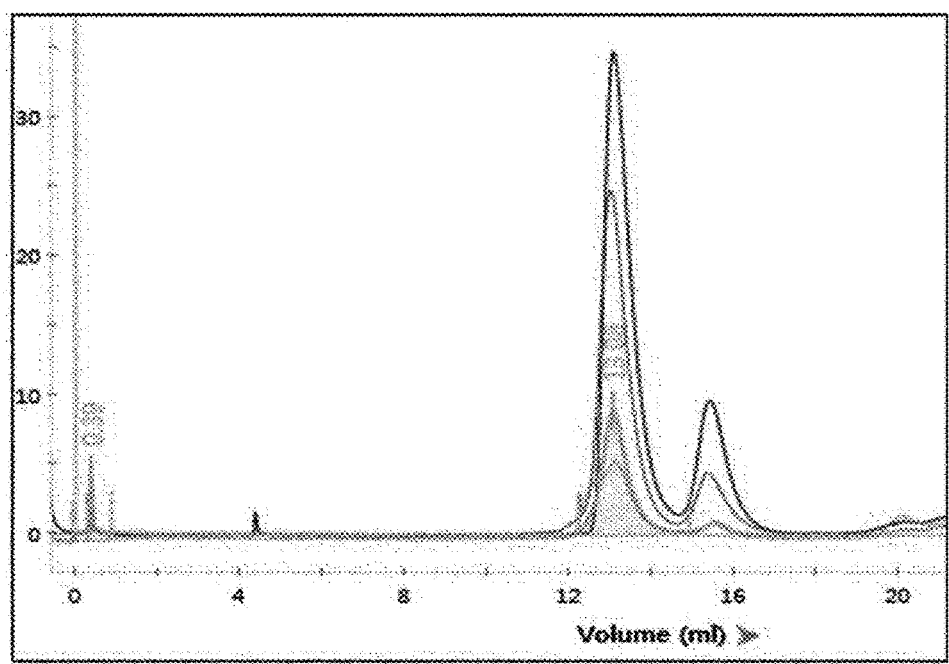
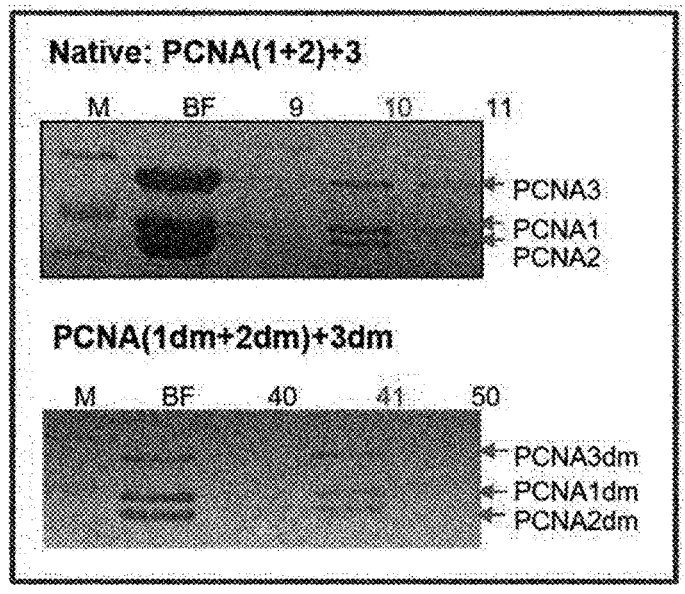

【Fig.11C】
C
| | $K_D$ (M) | $K_a$ | $K_d$ | $R^2$ |
|---|---|---|---|---|
| PCNA1-2 | $6.31 \times 10^{-9}$ | $2.55 \times 10^5$ | $1.61 \times 10^{-3}$ | 0.99 |
| PCNA3-2 | $3.17 \times 10^{-6}$ | $3.13 \times 10^3$ | $9.92 \times 10^{-3}$ | 0.92 |
| PCNA1dm-2dm | $2.65 \times 10^{-9}$ | $2.06 \times 10^5$ | $5.47 \times 10^{-4}$ | 0.99 |
| PCNA2dm-3dm | $5.71 \times 10^{-7}$ | $1.38 \times 10^4$ | $7.89 \times 10^{-3}$ | 0.94 |
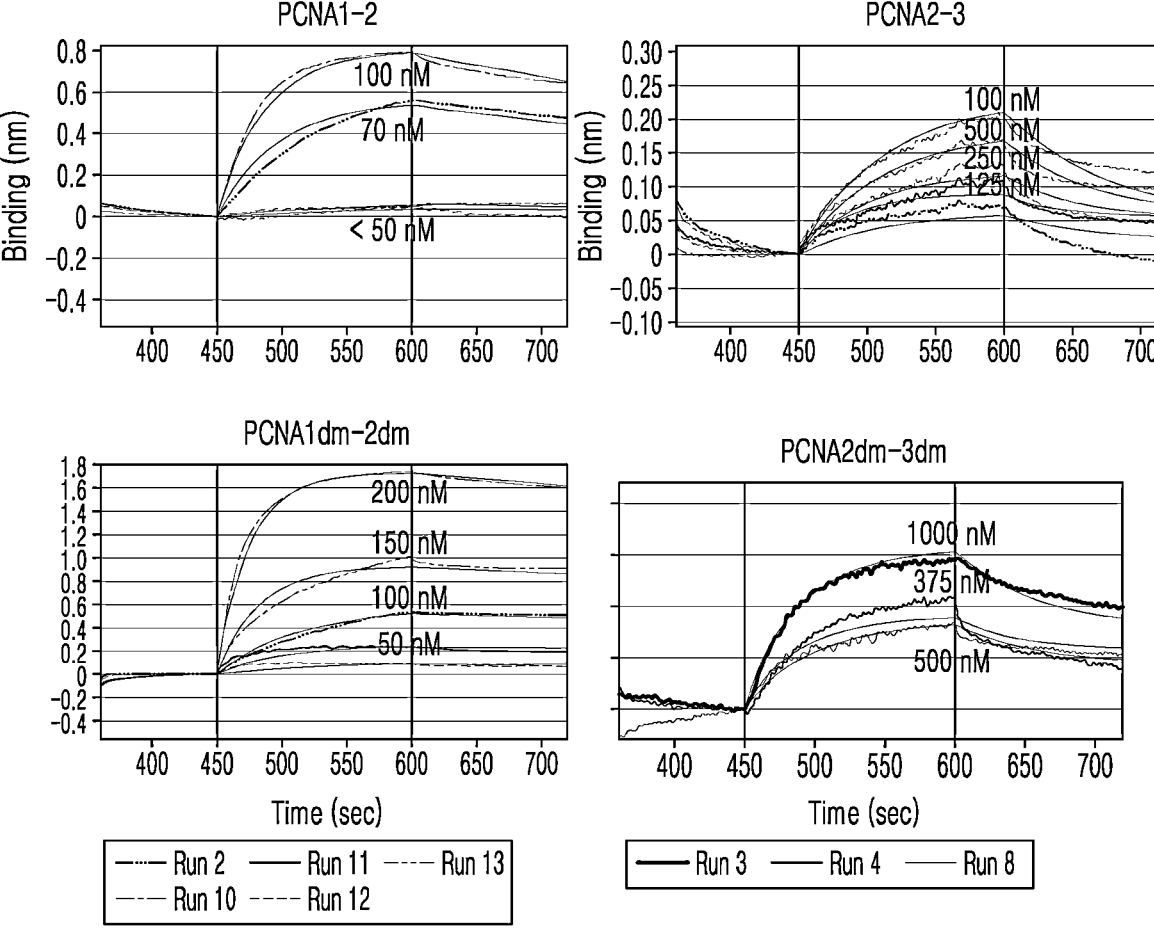

【Fig.12A】
A
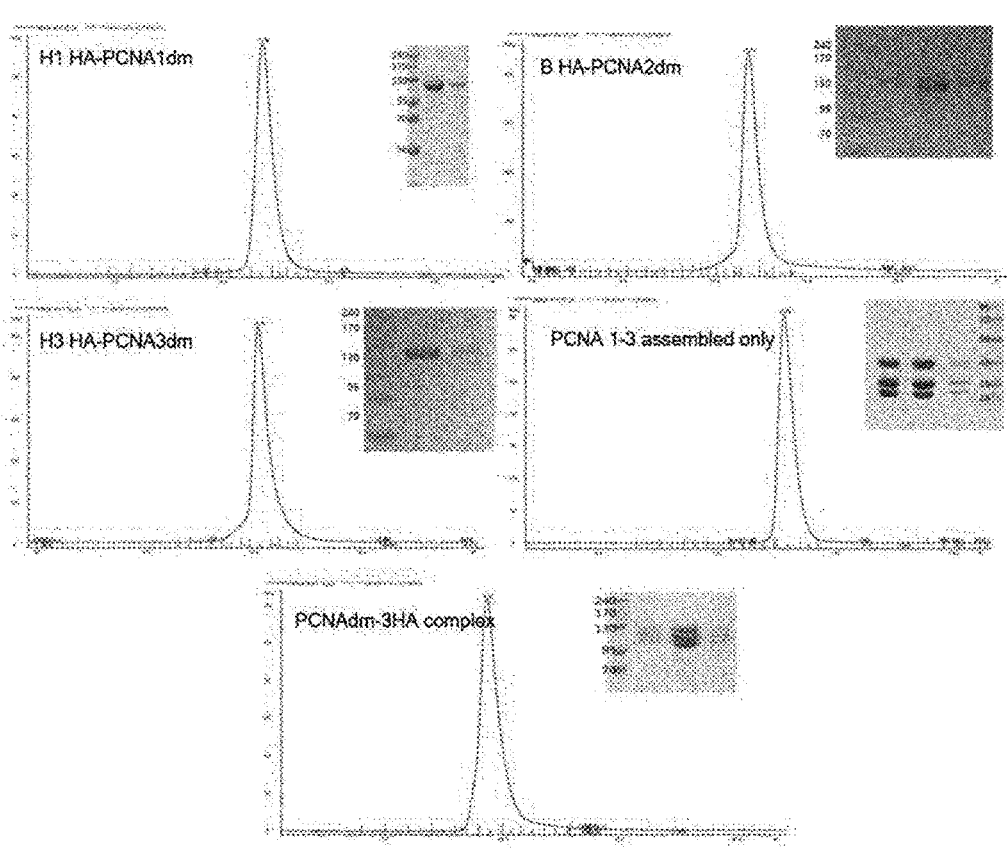
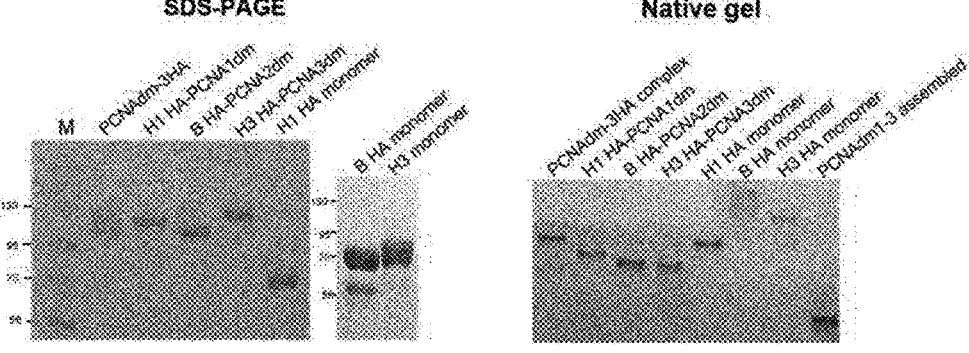

【Fig.12B】
B
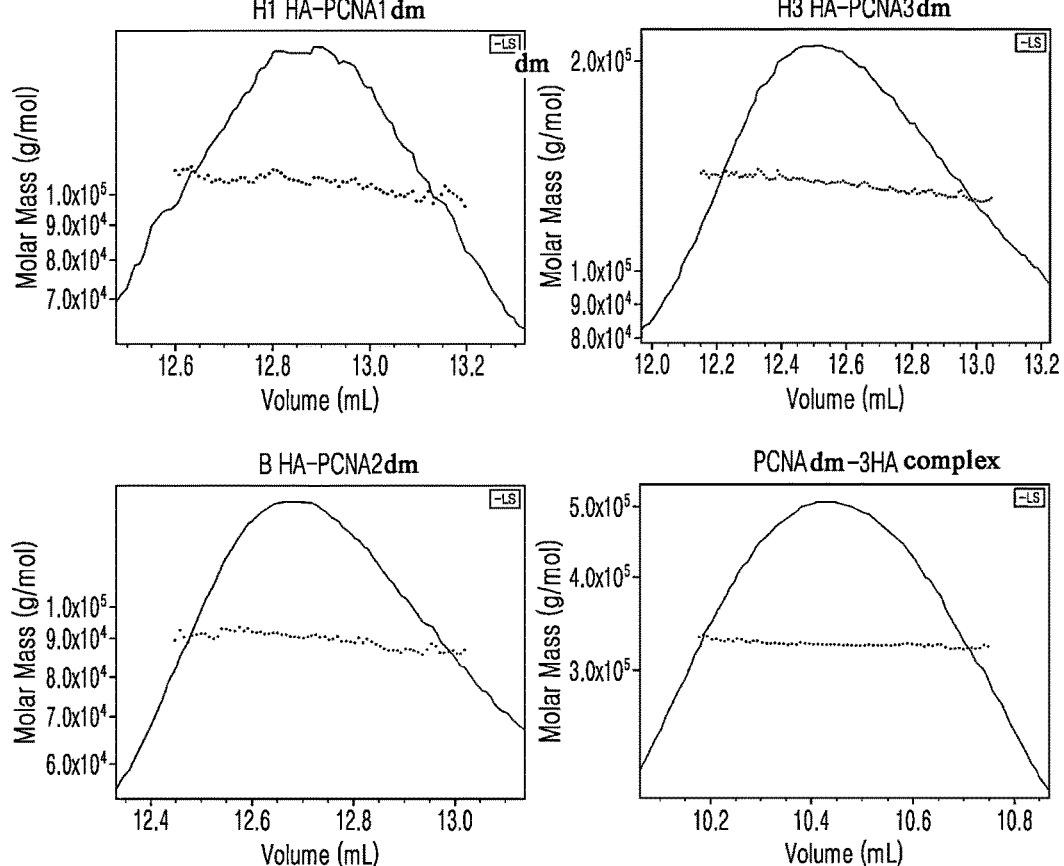

【Fig.12C】
C
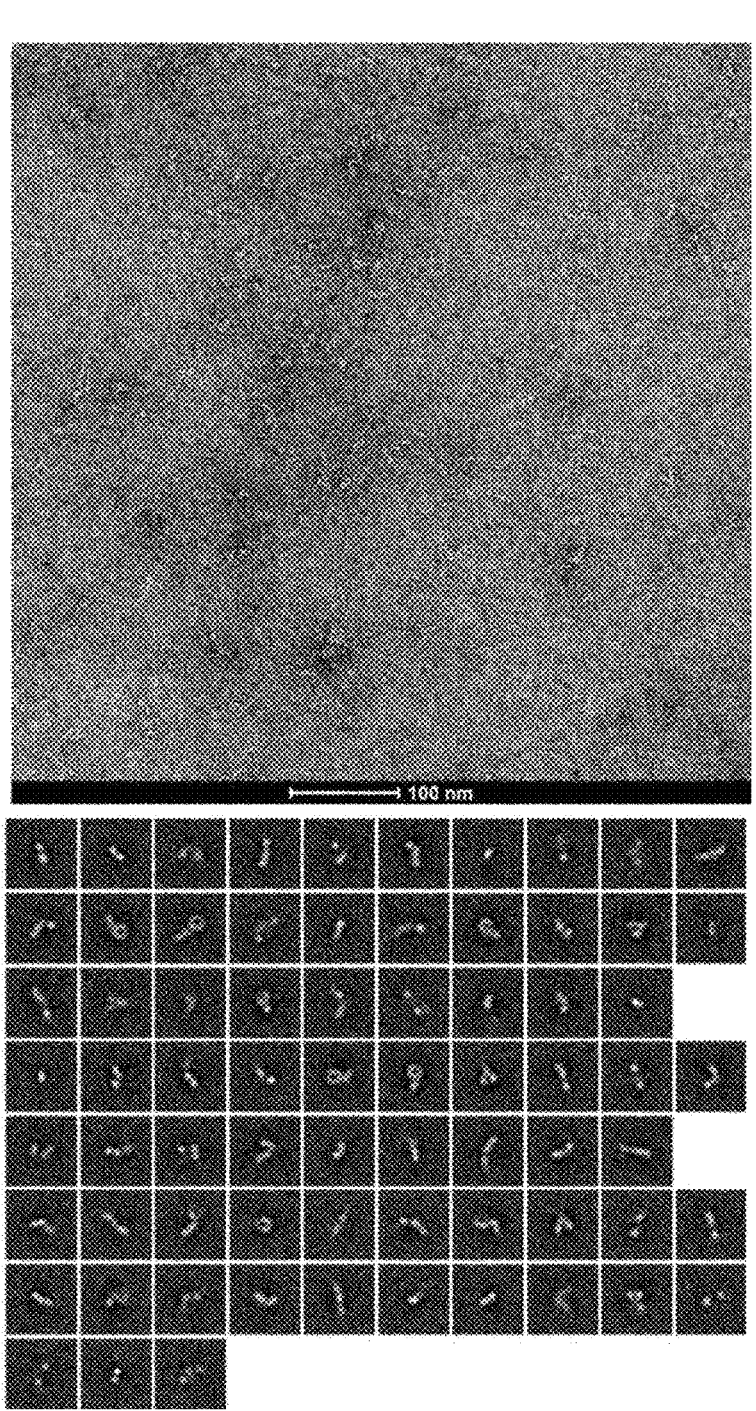

【Fig.13A】
A
H1 PR8 challenge
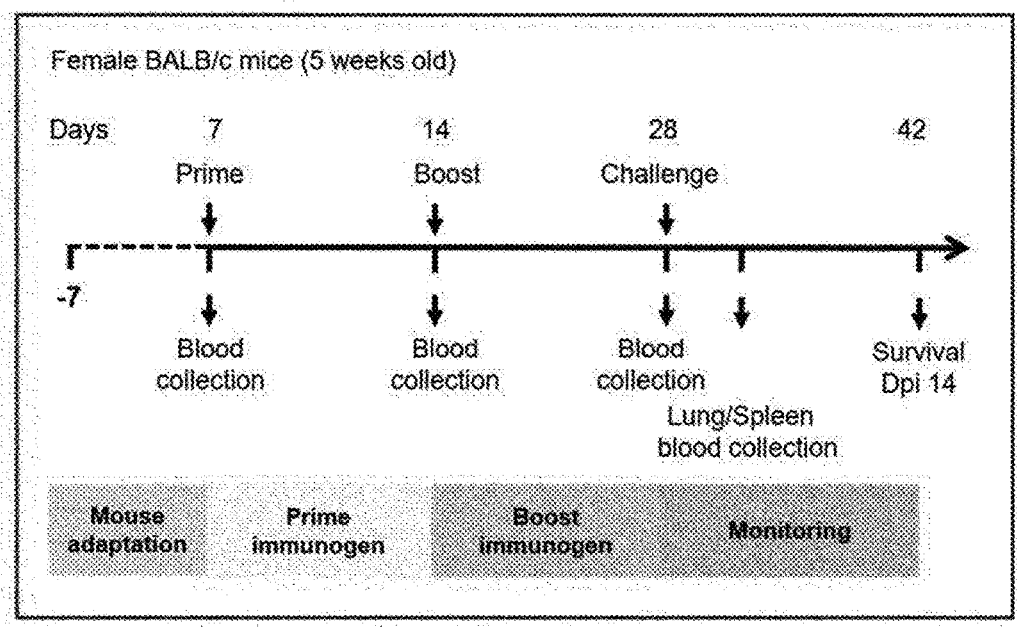
| | | Mouse group | No. of mouse (total 60) |
|---|---|---|---|
| 1 | | Naïve (No Vaccine, No Virus) | 5 |
| 2 | | PBS + adjuvant | 8 |
| 3 | | PCNA1/2/3dm assembled 15 µg+ adjuvant | 8 |
| 4 | PR8 or X47 infection (9x10 PFU ≈3MLD$_{50}$/mo use) | H1 HA monomer 15 µg + adjuvant | 8 |
| 5 | | H1 HA-PCNA1dm 15 µg + adjuvant | 8 |
| 6 | | SK Bioscience TIV, 15 µg (167 ul) | 8 |
| 7 | | H1, H3, B HA trimer mixture 15 µg + adjuvant | 8 |
| 8 | | H1, H3, B HA monomer mixture 15 µg + adjuvant | 8 |
| 9 | | PCNAdm-3HA 15 µg + adjuvant | 8 |

【Fig.13B】
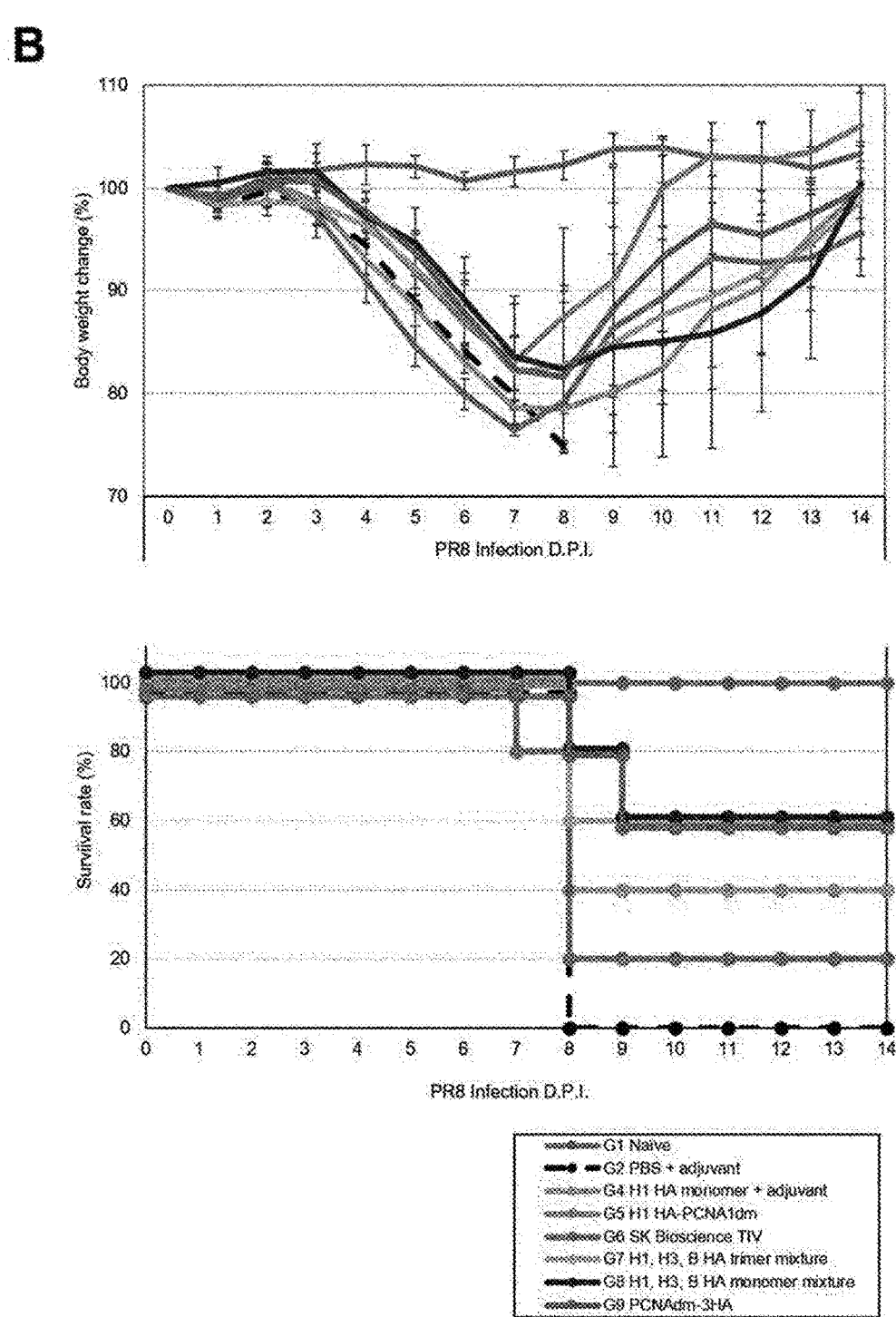

【Fig.13C】
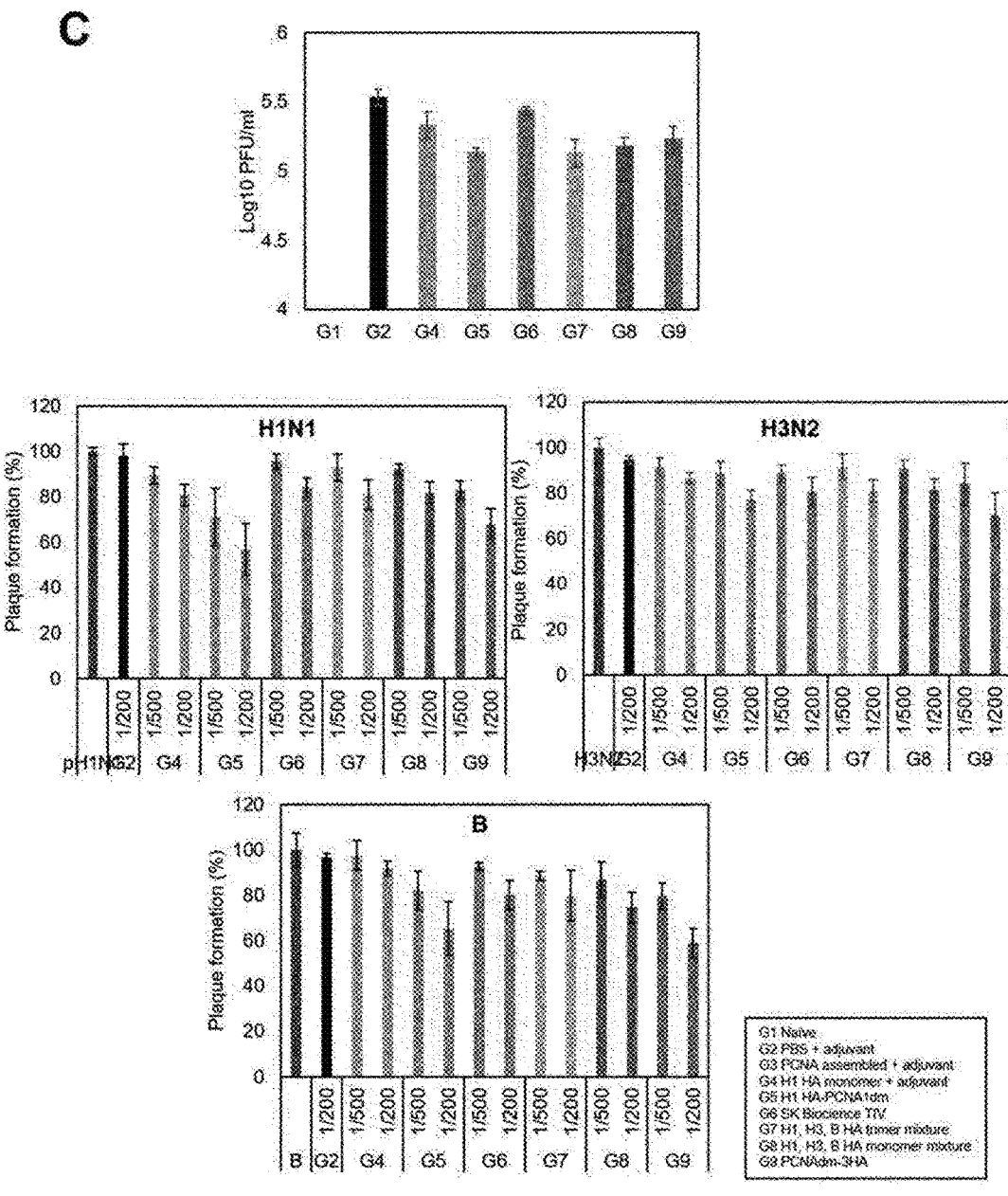

【Fig.13D】
D
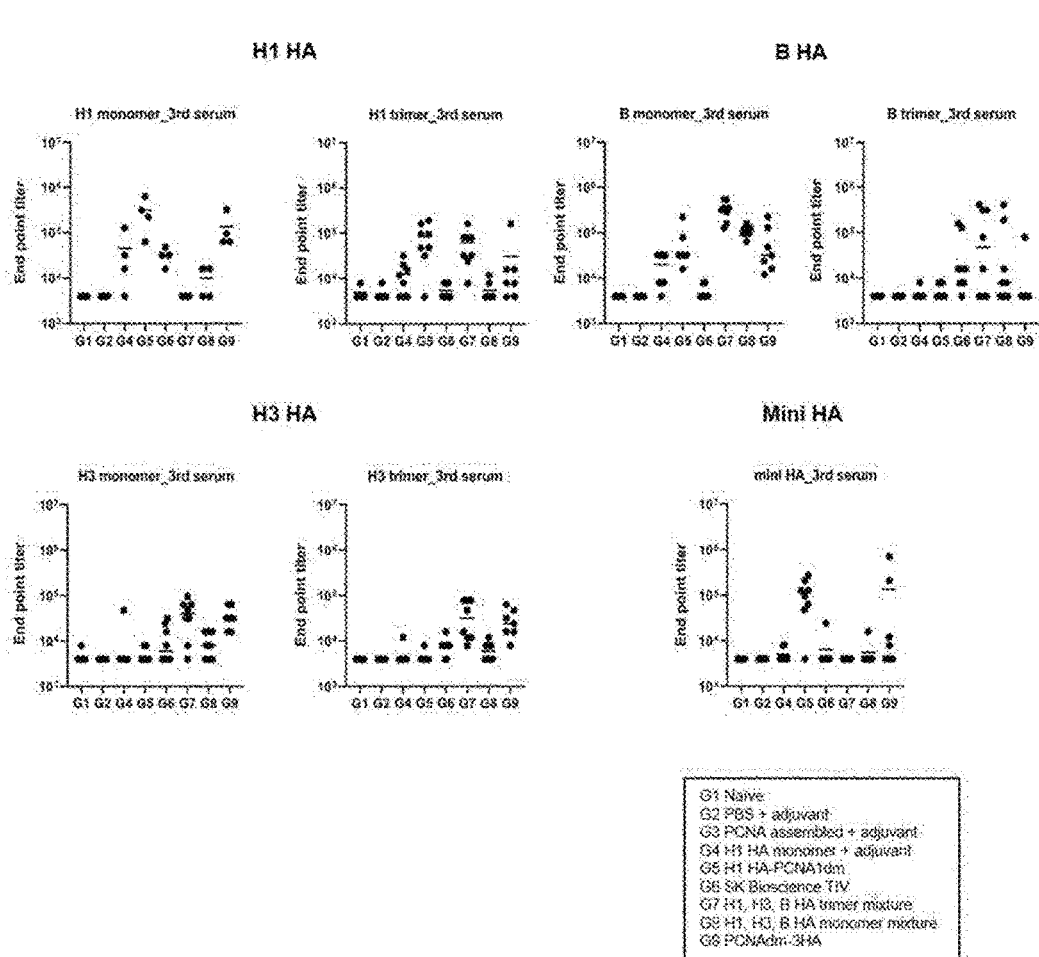

【Fig.14A】
A
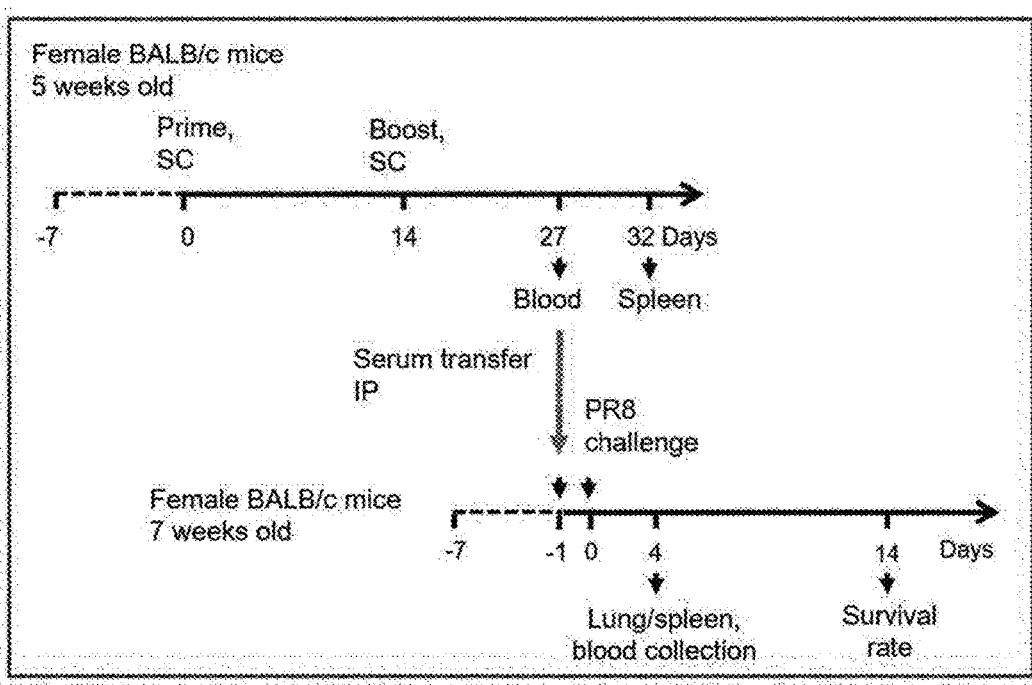
| Mouse group | | No. of mouse | |
|---|---|---|---|
| | | B cell&serum | passive |
| 1 | Naïve (No Vaccine, No Virus) | 2 | 5 |
| 2 | PBS + adjuvant | 2 | 7 |
| 4 | H1 HA monomer + adjuvant | 10 | 7 |
| 5 | H1 HA-PCNA1dm + adjuvant | 10 | 7 |
| 6 | SK Bioscience TIV | 10 | 7 |
| 9 | PCNAdm-3HA + adjuvant | 10 | 7 |

【Fig.14B】
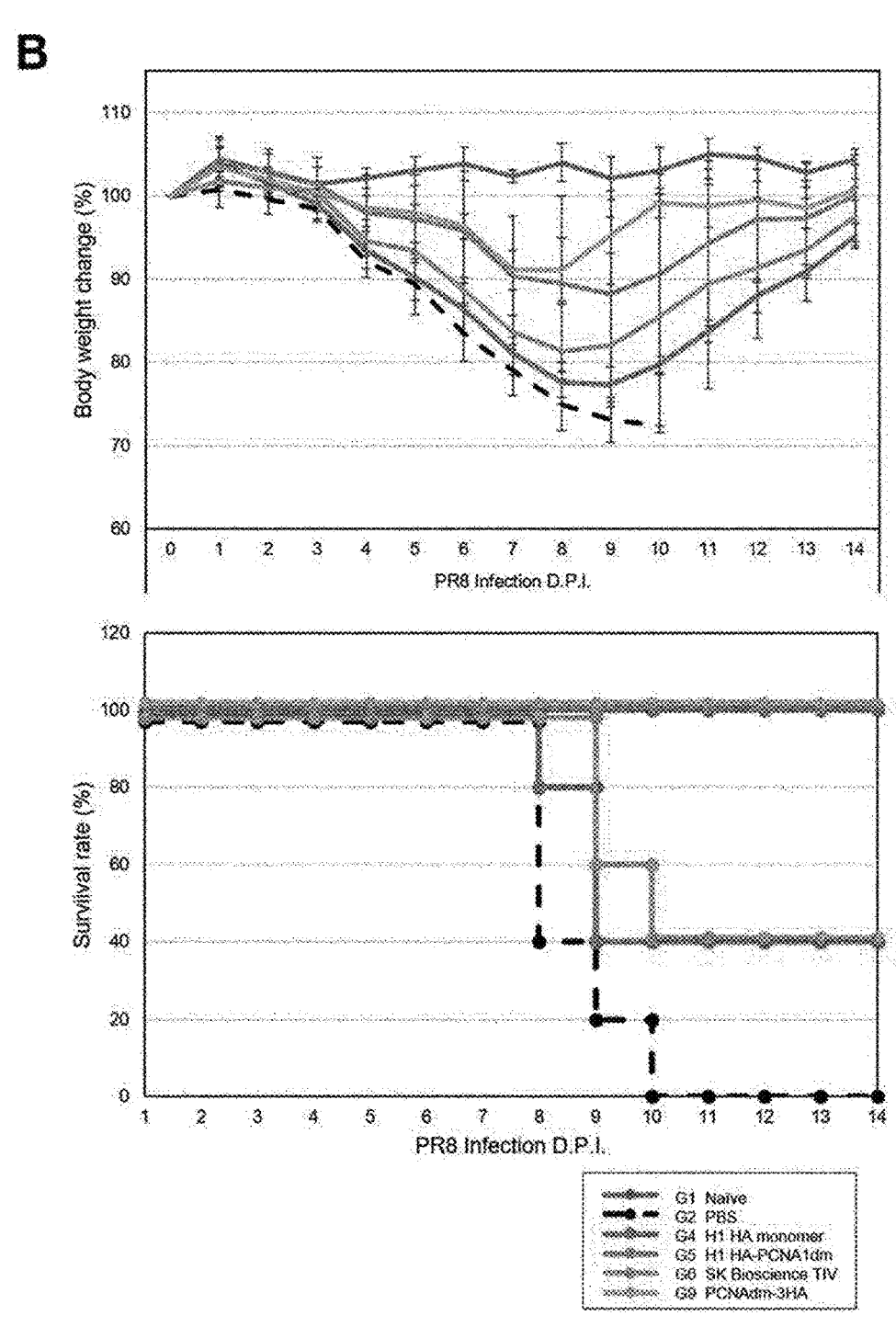

【Fig.14C】
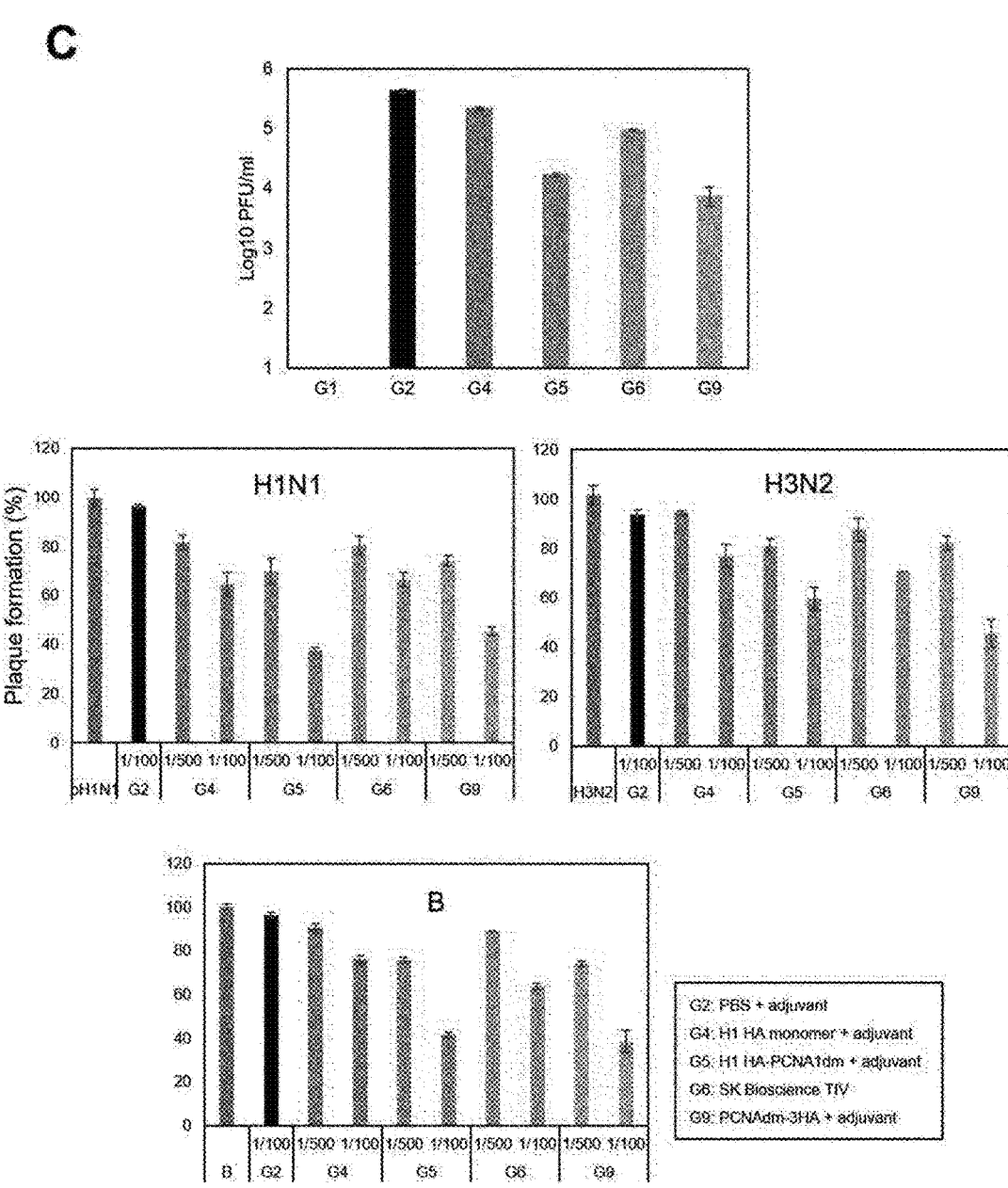

【Fig.14D】
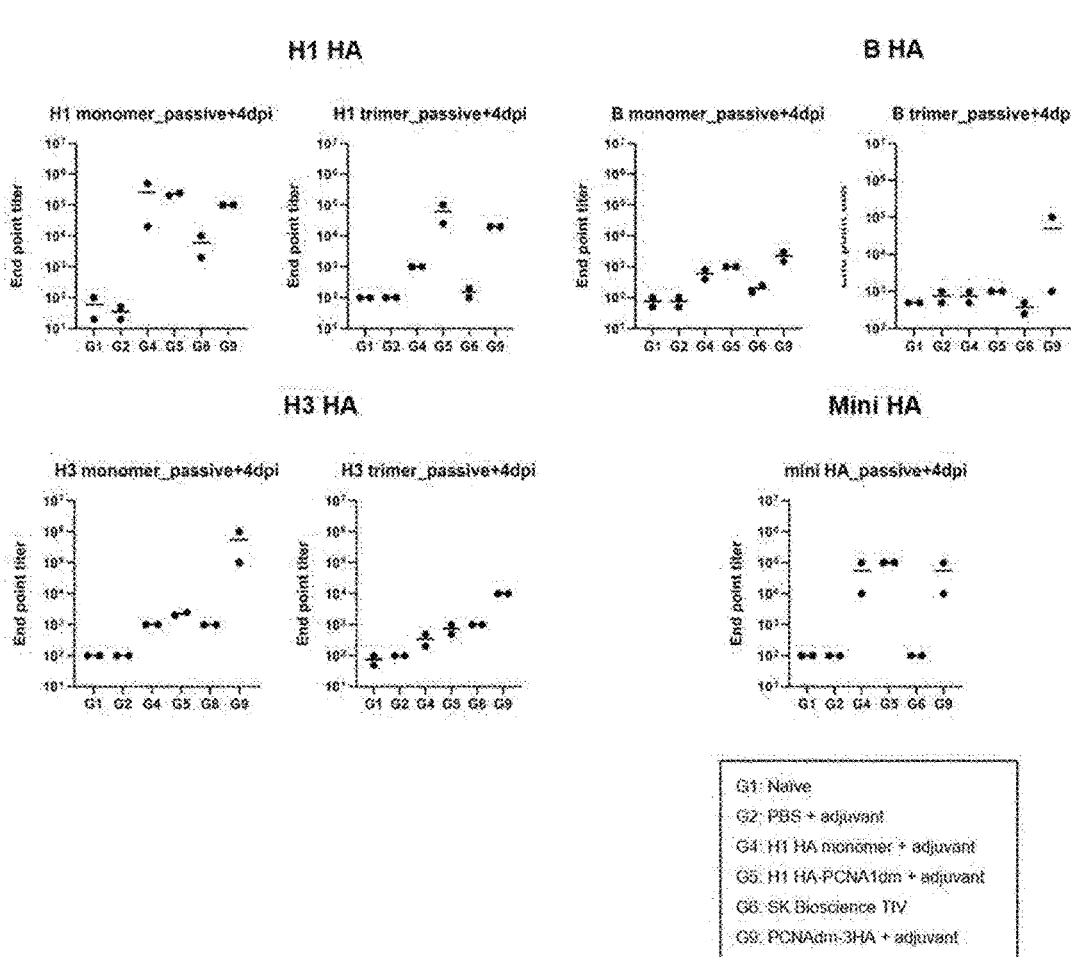

【Fig.15A】
A
H3 X47 challenge
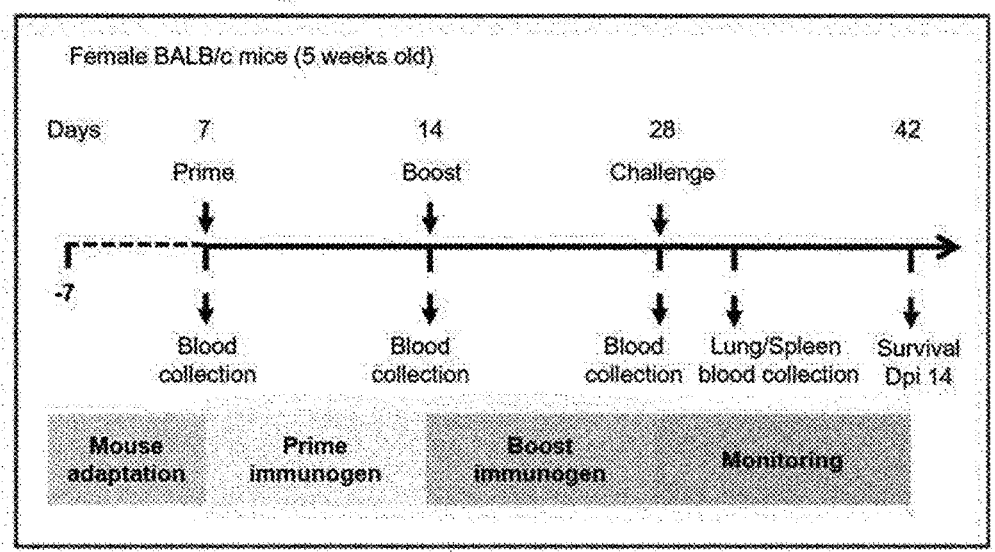
| | Mouse group | No. of mouse |
|---|---|---|
| 1 | Naïve (No vaccine, No virus) | 5 |
| 2 | PBS + adjuvant | 8 |
| 3 | Inactivated H3 X47 + adjuvant | 8 |
| 4 | SK Bioscience, TIV | 8 |
| 5 | PCNA1/2/3 assembled 15 µg + adjuvant | 8 |
| 6 | H3 HA monomer 15 µg + adjuvant | 8 |
| 7 | H3 HA-PCNA3dm 15 µg + adjuvant | 8 |
| 8 | H1, H3, B monomer mixture + adjuvant | 8 |
| 9 | PCNAdm-3HA 15 µg + adjuvant | 8 |

【Fig.15B】
B
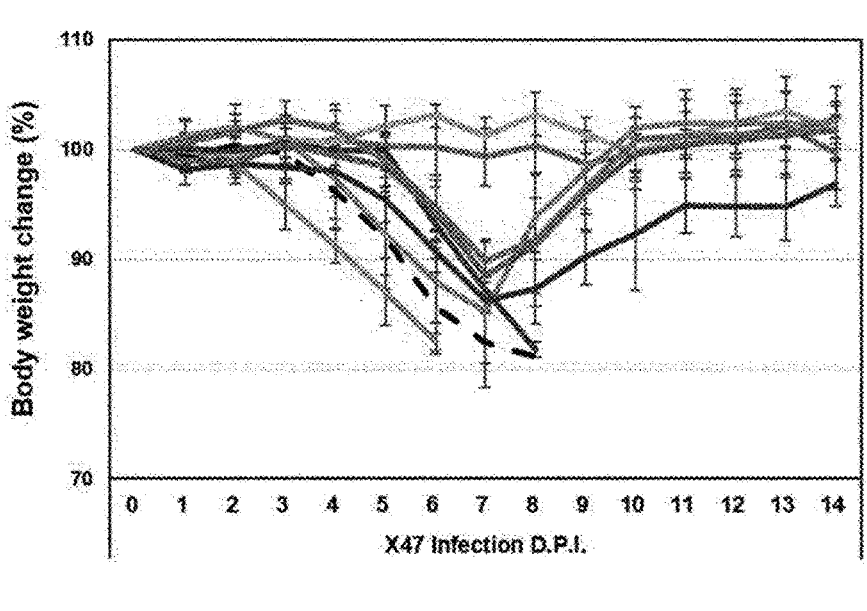
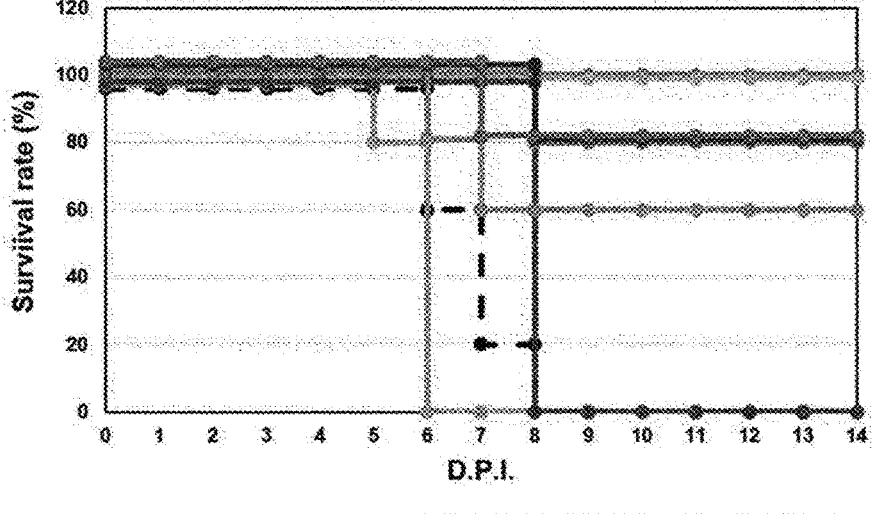
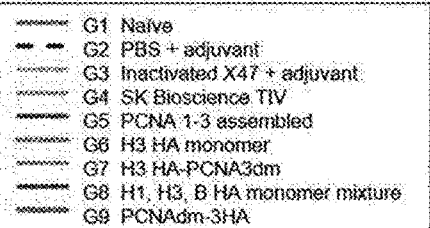

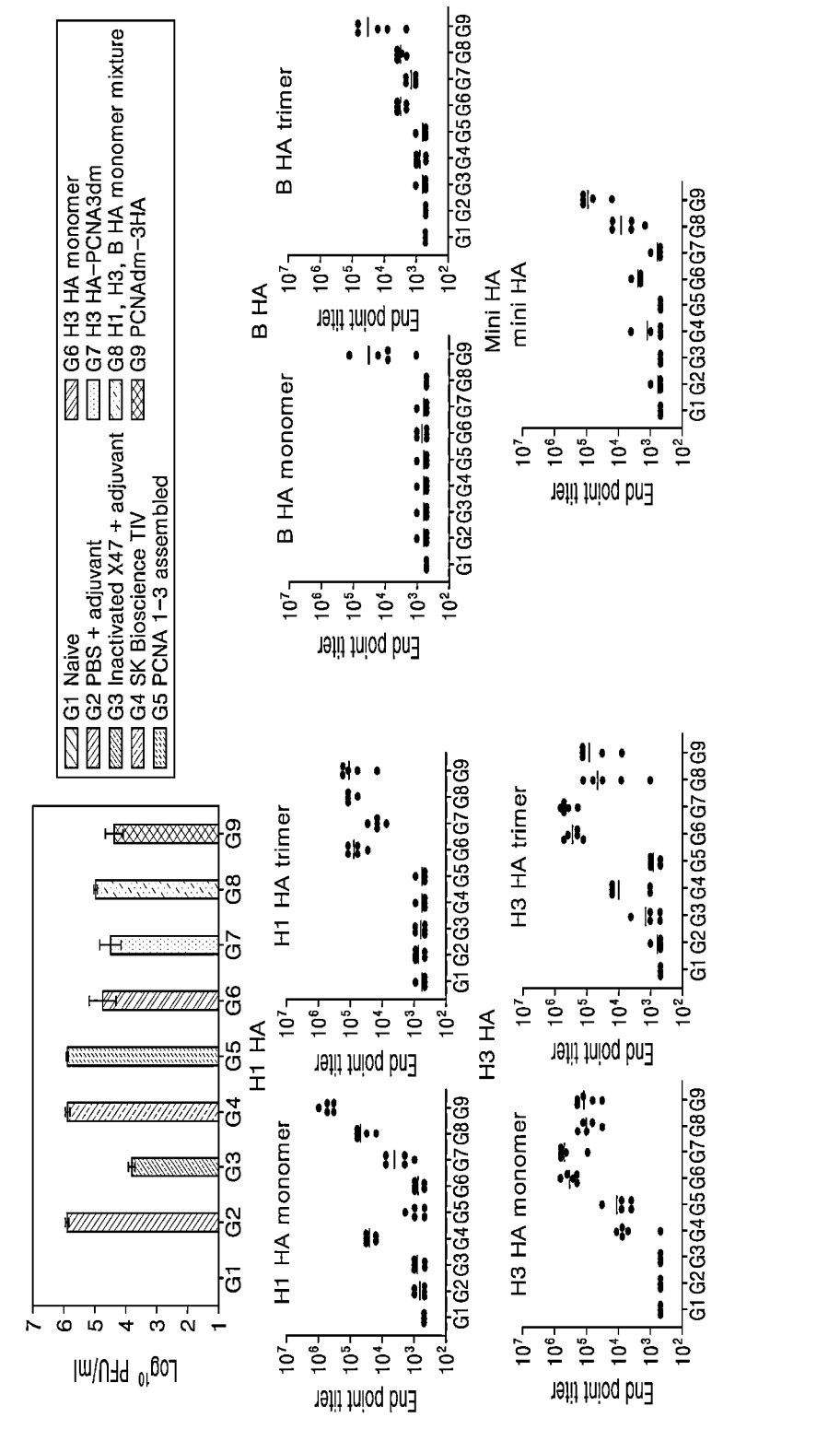
[Fig.15C]

ANTIGEN COMPOSITION FOR PREVENTING OR TREATING VIRAL INFECTIOUS DISEASES

CROSS REFERENCE TO RELATED APPLICATIONS

This application is a U.S. National Stage Application of International Application No. PCT/KR2021/000590, filed on Jan. 15, 2021, which claims the benefit under 35 USC 119(a) and 365(b) of Korean Patent Application Nos. 10-2020-0005553, filed on Jan. 15, 2020 and 10-2020-0124945 filed on Sep. 25, 2020, in the Korean Intellectual Property Office, the entire disclosures of which are incorporated herein by reference for all purposes.

TECHNICAL FIELD

The present invention relates to an antigen composition for preventing or treating viral infectious diseases containing an influenza virus recombinant hemagglutinin monomeric protein as an active ingredient.

The present invention also relates to an antigen composition for preventing or treating viral infectious diseases containing a scaffold-based fusion protein.

BACKGROUND ART

The development of vaccines that impart immunity against specific disease or pathogens to animals, including humans, has limitations due to various subtypes present in the target virus. For example, the flu is a respiratory disease caused by infection with the influenza virus, which occurs in 10-20% of the world's population each year. In particular, about 2 million cases and an economic loss of about $12 billion occur annually in the United States alone. Influenza viruses exist in various subtypes due to their biological characteristics. This is due to the diversity of two proteins that determine the immunogenicity of viruses, namely, hemagglutinin (HA) and neuraminidase (NA). For example, 16 types of HA and 9 types of NA for influenza A exist and mutations thereof often occur. Therefore, in order to develop flu vaccines, it is necessary to predict in advance strains expected to be prevalent in that year and use the strains to prepare vaccines. Therefore, disadvantageously, vaccines should be repeatedly prepared every year in line with the epidemic strains and existing vaccines are much less effective when the actual epidemic strain does not match the strain used for vaccine preparation, or when new greatly mutated strains are epidemic.

In an attempt to solve this problem, research is underway on the development of universal vaccines for influenza virus using sites with high conservation of amino acid residues present on the surface proteins of influenza viruses. For example, "mini-HA" using hemagglutinin proteins having highly conserved epitopes exhibits viral efficacy in the experiment performed using an H1 subtype protein as an antigen, which demonstrates the universality of influenza viruses (Impagliazzo A et al., Science 349.6254 (2015): 1301-1306).

Nevertheless, there is a continuing urgent need for the development of novel vaccines, which can be used as extensive versatile vaccines for a variety of variants, especially for viral vaccine compositions using fusion proteins that guarantee safety, enable mass production and are easy to prepare.

DISCLOSURE

Technical Problem

It is one object of the present invention to provide an antigen composition containing, as an active ingredient, an influenza virus recombinant hemagglutinin monomeric protein having five or eight mutations and disulfide bond mutation, which has no risk of side effects or toxicity and is highly effective in preventing and treating various viruses including influenza virus.

The present invention has been made in an attempt to develop a universal vaccine that can be widely used against various subtypes and variants and thus it is another object of the present invention to provide an antigen composition for preventing or treating viral infectious diseases, containing at least one fusion protein including a scaffold fragment and a recombinant antigen protein bound to the scaffold fragment.

Technical Solution

Since most universal vaccine development using antigens to influenza virus targets improvement in the effect of inducing an antibody recognizing a protein region with high amino acid conservation, in order to achieve the above objects, the present inventors found based on the results of animal experiments using mice and cell-based expression that the recombinant hemagglutinin monomer proteins have an excellent antiviral effect against influenza virus. Based thereon, the present invention was completed.

Thus, the present invention provides an antigen composition for preventing or treating viral infectious diseases containing, as an active ingredient, an influenza virus recombinant hemagglutinin monomeric protein having five or eight protein mutations and/or a disulfide bond mutation, represented by any one of SEQ ID NO: 1 to SEQ ID NO: 3.

The monomeric protein represented by SEQ ID NO: 1 is H1 subtype influenza virus recombinant hemagglutinin having five protein mutations and two disulfide bond mutations, the monomeric protein represented by SEQ ID NO: 2 is influenza B virus recombinant hemagglutinin having eight protein mutations, and the monomeric protein represented by SEQ ID NO: 3 is H3 subtype influenza virus recombinant hemagglutinin having five protein mutations and one disulfide bond mutation.

In addition, the present invention provides an antigen composition for preventing or treating viral infectious diseases containing at least one fusion protein including a scaffold fragment and a recombinant antigen protein bound to the scaffold fragment.

Advantageous Effects

The antigen composition for preventing or treating viral infectious diseases according to the present invention is highly effective in inhibiting the proliferation and replication of viruses having various subtypes and mutations, and is considered to have recyclability and safety due to the use of recombinant proteins and is thus widely used in the pharmaceuticals, life science and the like.

DESCRIPTION OF DRAWINGS

FIG. 1A shows the primary structure of influenza virus hemagglutinin and the tertiary structure of the monomer (top). The head region (blue) and stem region (orange) of the H1 hemagglutinin structure are shown and the positions of L73S, I77S, L80S, F88E, and V91W mutant amino acids are shown in the primary and tertiary structure models. The inset shows the interface between the monomers viewed from the top of the 3-fold axis of a trimer. In H1 subtype hemagglutinin, L73S, among the five mutations, exhibited an at least 5-fold increase in the expression rate (middle). As a result, B and H3 hemagglutinins have eight mutations, namely, L73S, I77S, L80W, V84W, L87S, T91W, L98S, and L102W, of B/Florida/4/2006 (FL04) virus hemagglutinin and five mutations, V73S, I77S, L80S, V84W, and L91W, of A/Gyeongnam/684/2006 (H3N2) (Gy684) virus hemagglutinin, respectively (bottom). In addition, a disulfide bond mutation of V20C-E105C/M320C-H111C is formed in H1 hemagglutinin and a disulfide bond mutation of M320C-T111C is formed in H3 hemagglutinin.

FIG. 1B shows an amino acid sequence of a monomer protein (H1 hemagglutinin monomer with five mutations and two disulfide bond mutations is represented by SEQ ID No.: 1, B hemagglutinin monomer with eight mutations is represented by SEQ ID No.: 2, and H3 hemagglutinin monomer with five mutations and one disulfide bond mutation is represented by SEQ ID No.: 3) including five or eight mutations and a disulfide bond mutation in H1, H3, and B hemagglutinin. Mutated amino acid residues are indicated in red.

FIG. 1C shows conversion of a trimer into a monomer through hemagglutinin mutation (top, left). The position of the amino acid with disulfide bond mutation is represented through the structure of the H1 hemagglutinin (top, right). Mutation site of the monomer final product obtained by hemagglutinin mutation is shown for each hemagglutinin through H1-, H3- and B-type hemagglutinin gene cloning design (bottom). H1-, H3-, and B-type virus-derived hemagglutinin genes in each stain are fused to the foldon to produce constructs and the GP67 signal sequence and His-tag are used for each construct for easy purification.

FIG. 2A shows the results of purification through chromatography and denaturing electrophoresis of the monomer including H1 subtype hemagglutinin five mutations and disulfide bond mutation (top) and the exact molecular size of the hemagglutinin monomer measured through size exclusion chromatography-multi angle light scattering) (bottom). In the monomer with disulfide bond mutation, the expression of the mutant protein having two disulfide bonds is improved and the molecular weight of the final monomer (H1 HA_5m_2DS) is 70.1 kDa.

FIG. 2B shows the results of purification through chromatography and denaturing electrophoresis of the monomer having H3 subtype hemagglutinin five mutations and one disulfide bond mutation (top) and the exact molecular size of the hemagglutinin monomer measured through gel filtration chromatography-multi-angle light scattering (bottom). The molecular weight of the final monomer (H3 HA_5m_DS) is 85.0 kDa.

FIG. 2C shows the results of purification through chromatography and denaturing electrophoresis of the monomer having B-type hemagglutinin eight mutations (top) and the exact molecular size of the hemagglutinin monomer measured through gel filtration chromatography-multi-angle light scattering (bottom). The molecular weight of the final monomer (B HA_8m) is 62.5 kDa.

FIG. 3A shows a transition temperature (Tm), indicating the stability of the monomer measured through differential scanning fluorimetry (DSF) when disulfide bond mutation is performed in addition five mutations H1 (top) and H3 (bottom) subtype hemagglutinins. The result of electrophoresis shows that the transit ion temperature of the H1 and H3 hemagglutinin antigen monomers is at least 4° C. higher than that of the five protein when disulfide bond mutation is performed, which indicates that the stability of the monomer is improved.

FIG. 3B shows the exact molecular size of the seasonal influenza virus and swine influenza virus hemagglutinin wild-type trimers, two-mutation monomer and five-mutation monomer measured through gel filtration chromatography-multi-angle light scattering. The hemagglutinin wild-type trimer, two-mutation monomer and five-mutation monomer have molecular weights of 205.9, 67.2, and 70.1 kDa, respectively. The difference in molecular weight between the monomers is caused by seasonal influenza A/Thailand/CU44/2006 (CU44) and A/California/07/2009 (CA09)-derived hemagglutinin proteins.

FIG. 3C shows the transition temperature of the hemagglutinin wild-type trimer and two-mutation monomer and five-mutation monomer of the seasonal influenza virus CU44 and swine influenza virus CA09. H1 subtype virus hemagglutinins have different transition temperatures and there is a difference of about 10° C. in transition temperature between the monomer and the trimer for the seasonal influenza, and there is a difference of about 10° C. in the transition temperature between the monomer and the trimer for the swine influenza. In particular, the five mutant monomer has a 2° C. higher transition temperature than the double mutant monomer, which is the result of the previous research, which indicates that the stability of the monomer is improved by five mutations.

FIG. 4 shows a mouse animal experiment scheme of the monomer having five or eight mutations and disulfide bond mutation in H1-, H3-subtype and B-type hemagglutinin. Eight mice were used in each group, an antigenic substance was administered twice at 2-week intervals, blood was collected at 0, 2, 4, and 5 weeks after antigen administration and priming, and viral infection was performed by intranasal administration. The total duration of the experiment was 42 days. Group 1: naive mouse, Group 2: PBS buffer+adjuvant, Group 3: monomer including H1 hemagglutinin having five mutations and two disulfide bond mutations+adjuvant, Group 4: cell-cultured influenza trivalent vaccine manufactured by commercial SK bioscience, Group 5: mixture of mutant monomer including H1, H3 and B hemagglutinin having five or eight mutations and disulfide bond mutation+adjuvant.

FIG. 5 shows the results of the mouse animal experiments using the H1 hemagglutinin mutant monomer, and the mixture of H1, H3 and B hemagglutinin mutant monomers. Daily weight change (top) and survival rate (bottom) in mice infected with PR8 (H1N1) virus are monitored, and each group is the same as the group set forth in FIG. 4.

FIG. 6 shows virus concentration in lung tissue as the result of mouse animal experiments using the H1 hemagglutinin mutation monomer, the mixture of H1, H3 and B hemagglutinin mutant monomers and the like. FIG. 6 shows virus titers (Pfu/ml) measured from lung tissue of mice sacrificed on the 4th day after PR8 (H1N1) virus infection and each group is the same as the group set forth in FIG. 4.

FIG. 7 shows the results of plaque reduction neutralization analysis using mouse serum in animal experiments and specifically, using serum collected from mice of each group. A PR8 virus-diluted mouse serum sample was added to MDCK cells and each group is the same as the group set forth in FIG. 4. The number of plaques was measured after staining with crystal violet.

FIG. 8A shows the antibody titer, which is the result of ELISA analysis using mouse serum in an animal experiment. H1 HA_5m_2DS (top) and H1 HA CU44 trimer (bottom) are used as immobilized antigens and serum collected from mice of each group is used. The results of ELISA experiments using the serum collected from mice after antigen administration (prime-boost) are shown, the ELISA experiment is performed using serum collected from mice, and each group is the same as the group set forth in FIG. 4. The absorbance of the secondary antibody-horseradish peroxidase reaction is measured at a wavelength of 450 nm by ELISA using a microplate.

FIG. 8B shows the antibody titer, which is the result of ELISA analysis using mouse serum in an animal experiment. H3 subtype hemagglutinin (top) and type B hemagglutinin (bottom) are used as immobilized antigens and serum collected from mice of each group is used. The results of ELISA experiments using the serum collected from mice after antigen administration (prime-boost) are shown, the ELISA experiment is performed using serum collected from mice, and each group is the same as the group set forth in FIG. 4. The absorbance of the secondary antibody-horseradish peroxidase reaction was measured at a wavelength of 450 nm by ELISA using a microplate.

FIG. 8C shows the hemagglutinin antibody titer (top) using mouse serum in an animal experiment using mini-HA having the hemagglutinin stem region. Results of denaturing electrophoresis, when using Mini-HA as immobili zed antigen, which is a trimer consisting only of a stem region (Impagliazzo A et al., 2015. Science 349: 1301-1306) (middle) and concentration-dependent activity when a known stem-specific antibody (C179) is used as a control group (bottom). Therefore, only the stem-specific antibody in the serum can participate in the reaction and the specific antibody is detected by ELISA using serum collected from mice after antigen administration (prime-boost). Each group is the same as the group set forth in FIG. 4.

FIG. 9 is a schematic diagram illustrating the mechanism by which a plurality of recombinant antigen proteins is exposed to the outside of a cyclic scaffold formed by self-assembly of scaffold fragments included in a plurality of fusion proteins according to the present invention.

FIG. 10A shows the trimer-monomer relationship (top left), and head region (blue) and stem region (orange), the positions of mutant amino acids, L73S, I77S, L80S, F88E, and L73S of the H1 HA monomer structure using the seasonal mutant influenza virus HA tertiary structure model (top right). The H1 HA, B HA, and H3 HA mutant proteins are HA derived from viruses A/California/07/2009 (CA09), B/Florida/4/2006 (FL04), A/Gyeongnam/684/2006 (H3N2) (Gy684), respectively. H1 HA, B HA, and H3 HA mutant proteins have five mutations of L73S, I77S, L80S, F88E, and T91W, eight mutations of V91W, L73S, I77S, L80W, V84W, L87S, L98S, and L102W, and five mutations of V73S, I77S, L80S, V84W, and L91W (below). In addition, FIG. 10A is a schematic diagram illustrating the relative positions in the primary structure of the protein having two disulfide bond mutations, of V29C/E105C and M320C/H111, and one disulfide bond mutation of M320C/T111C, in H1 HA and H3 HA, respectively, and PCNA1, PCNA2, and PCNA3 mutations. Each HA mutant gene was fused with a foldon to produce a construct, and H1 HA, B HA, and H3 HA mutant genes were bound to PCNA1dm, PCNA2dm and PCNA3dm N-terminals, respectively, and these products are called "H1 HA-PCNA1dm", "B HA-PCNA2dm" and "H3 HA-PCNA3dm", respectively. The fused construct is obtained by attaching an SGG linker between each HA and PCNA, and the GP67 signal sequence and His-tag are used for each construct for easy purification.

FIG. 10B shows mutations of amino acid residues of the H1 HA, B HA, and H3 HA monomeric proteins (indicated in red) in the entire amino acid sequence.

FIG. 10C is a table showing the assembly-improved mutation residues of PCNA1, PCNA2, and PCNA3, which are PCNA subunits (scaffold fragments) (top), mutation residues at the PCNA1-PCNA2 and PCNA2-PCNA3 interfaces in the PCNA tertiary structure (middle), and each mutation amino acid residue (indicated in red) in each subunit amino acid sequence of the PCNA (bottom).

FIG. 11A shows the result of final size-exclusion chromatography (SEC) of PCNA wild-type subunits, namely, PCNA1, PCNA2, and PCNA3 and mutant subunits, namely, PCNA1dm, PCNA2dm, and PCNA3dm in the chromatographic purification step after bacterial expression (top), the results of denaturing SDS-PAGE indicating the relative molecular weight of the highly purified PCNA subunits (bottom), and the results before (BF) and after (AF) syringe filtering to check the aggregation of PCNA subunit wild-type and mutant proteins.

FIG. 11B shows the results of final size-exclusion chromatography (SEC) of PCNA wild-type subunits, namely, PCNA1, PCNA2, and PCNA3 and mutant subunits, namely, PCNA1dm, PCNA2dm, and PCNA3dm in the chromatographic purification step after bacterial expression (top). Each of PCNA1dm, PCNA2dm, and PCNA3dm exhibits an elution volume of about 13 ml in the SEC and the result of denaturing electrophoresis (SDS-PAGE) that purified PCNA wild-type and mutant protein subunits exhibited identical size in the range of 28 to 40 kDa (bottom).

FIG. 11C shows comparison in the assembly binding constant $K_D$ between the PCNA1dm, PCNA2dm, and PCNA3dm mutant subunits and the PCNA protein wild-type subunits. Bio-layer interferometer (BLI) blitz system (ForteBio, Menlo Park, CA, U.S.A.) is used to measure the binding constant between PCNA1-PCNA2 and PCNA2-PCNA3 wild-type and mutant subunits. The rate constants $k_a$, and $k_d$ and the binding constant $K_D$ for the PCNA1dm-PCNA2dm reaction and PCNA3dm-PCNA2dm reaction are measured in the concentration range from 50 to 1,000 nM, as compared to the wild-type protein binding reaction. The result shows that the binding of PCNA mutant is improved 3 to 6 times compared to the wild type.

FIG. 12A shows the results of size exclusion chromatography and denaturation electrophoresis (SDS-PAGE), indicating the results of purification and assembly of the fusion proteins, namely, H1 HA-PCNA1dm, B HA-PCNA2dm, and H3 HA-PCNA3dm, formed by binding H1, B, and H3 HA mutant monomers for animal experiments to PCNA1dm, PCNA2dm and PCNA3dm, respectively, and shows the results of denaturing and non-denaturing electrophoresis (FIG. 12A below) of highly purified PCNA subunits (top, inset). The final assembled and purified PCNAdm subunits have a molecular weight of 28 to 40 kDa and the PCNAdm3HA complex bound with HA has a molecular weight of 100 to 130 kDa. FIG. 12A shows the results of analysis of H1 HA, B HA, and H3 HA monomers, in addition to PCNAdm-3HA, H1 HA-PCNA1dm, B HA-PCNA2dm, and H3 HA-PCNA3dm, in denaturing and non-denaturing electrophoresis experiments of antigens used in animal experiments (below). In addition to the relative molecular weight of the antigens used, purity and concentrations are determined.

FIG. 12B shows molecular weights of fusion proteins, H1 HA-PCNA1dm, B HA-PCNA2dm, and H3 HA-PCNA3dm in which H1, B, and H3 HA mutant monomers are bound to PCNA1dm, PCNA2dm, and PCNA3dm, respectively, measured using a multi-angle light scattering (SEC-MALS) device, after final purification. The molecular weights of the H1 HA-PCNA1dm, B HA-PCNA2dm, and H3 HA-PCNA3dm fusion proteins are 103.8, 89.9, and 133.2 kDa, respectively, and the molecular weight of the final assembled PCNAdm-3HA is 326.3 kDa (top, left). Denaturing electrophoresis (SDS-PAGE) results show the relative molecular weights of H1 HA-PCNA1dm and PCNAdm-3HA complexes (top, right), and show the results of SEC-MALS of H1 HA-PCNA1dm, B HA-PCNA2dm, H3 HA-PCNA3dm and PCNAdm-3HA antigens (bottom).

FIG. 12C shows the results of observation of PCNAdm-3HA using transmission electron microscope (TEM) with negative staining (top) and 2D averaging (bottom). FIG. 12C shows the results of observation of partially assembled PCNAdm-3HA and the structure of PCNAdm-3HA heterotrimers having a particle size of 20 to 30 nm.

FIG. 13A shows a challenge mouse animal experiment daily scheme of the PR8 H1N1 virus belonging to influenza virus group 1 using HA monomers, scaffold multivalent antigens and the like. Eight mice were used in each group (5 mice in the control naive group), the antigen substance was administered twice at an interval of 2 weeks, and blood was collected after 0 weeks, 2 weeks, 4 weeks, and 4 weeks+4 days after antigen priming and PR8 H1N1 subtype virus infection was performed by intranasal administration. The total duration of the experiment was 42 days, and each group was as follows. Group 1: naive mice, Group 2: PBS buffer+adjuvant, Group 3: PCNA1dm-PCNA2dm-PCNA3dm assembled+adjuvant, Group 4: H1 HA monomer+adjuvant, Group 5: H1 HA-PCNA1dm+adjuvant, Group 6: Commercial SK bioscience trivalent vaccine, Group 7: H1 HA, H3 HA, B HA trimer mixture+adjuvant, Group 8: H1 HA, H3 HA, B HA mutant mixture+adjuvant, Group 9: PCNAdm-3HA+adjuvant.

FIG. 13B shows the results of mouse animal experiments using the H1 HA monomer, H1 HA-PCNA1dm, and the multivalent antigen PCNAdm-3HA protein fused with H1, B, and H3 HA. The daily weight change (top) and survival rate (bottom) are shown in mice infected with PR8 (H1N1) virus. A commercial trivalent vaccine purchased from SK bioscience is used as a positive control, a reduction in mouse body weight of 20% or more is considered lethal, and each group is the same as in FIG. 13A.

FIG. 13C shows the virus titers in lung tissue expressed as log PFU/ml (top) after sacrifice of mice 4 days after PR8 (H1N1) virus infection as the results of mouse animal experiments using the H1 HAmonomer, H1 HA-PCNA1dm and the multivalent antigen PCNAdm-3HA protein fused with H1, B, and H3 HA. Whether or not antibodies are formed in blood collected 4 days after viral infection from the time of antigen inoculation is determined based on the result of the calculation of plaque reduction neutralization titer (PRNT) after reaction with H1N1, H3N2 and B viruses for 1 hour and infection of MDCK cells (middle, bottom).

FIG. 13D shows the antibody titers of H1 HA, H3 HA, and B HA trimers and monomers and stem-region mini HA used as antigens, based on ELISA using serum collected from mice. After an ELISA microplate is coated with 200 ng of HA antigen overnight at 4° C., the collected serum is serially diluted and primary antibody binding is performed at 37° C. for 1 hour. ELISA is performed using a microplate and the absorbance of the secondary antibody-horseradish peroxidase reaction is measured at a wavelength of 450 nm. The groups were the same as in FIG. 13A.

FIG. 14A shows the passive immunization animal experiment scheme using the immune serum induced with the HA monomer, scaffold multivalent antigens and the like. After acclimatization of 5-week-old mice for 1 week, the antigen substance was administered thereto twice at 2-week intervals, and 4 days after antigen administration (boosting), blood is collected and serum is separated. 7-week-old mice are divided into 6 groups (7 mice in each group, mice in the control native group), and the separated serum is subjected to intraperitoneal injection into the mice in each group. One day later, the mice are infected with PR8 H1N1 subtype virus in an intranasal manner and then the survival rate is measured. The total duration of the experiment is 42 days, and each group is as follows. Group 1: naive mice, Group 2: PBS buffer+adjuvant, Group 4: H1 HA monomer+adjuvant, Group 5: H1 HA-PCNA1+adjuvant, Group 6: SK bioscience commercial trivalent vaccine, Group 9: PCNAdm-3HA+adjuvant. The group number is the same as that of the group in FIG. 13A.

FIG. 14B shows the results of passive immunization animal experiment scheme using the immune serum induced with mouse animal experiments using the H1 HAmonomer, H1 HA-PCNA1dm, and the multivalent antigen PCNAdm-3HA proteins fused with H1, B, and H3 HA. The immune effect in mice infected with PR8 (H1N1) virus is shown based on daily body weight change (top) and survival rate (bottom). A commercial trivalent vaccine purchased from SK bioscience is used as a positive control, and a reduction in mouse body weight of 20% or more is considered lethal.

FIG. 14C shows the virus titers in lung tissue expressed as log PFU/ml (top) after sacrifice of mice on the $4^{th}$ day as the results of passive immunization animal experiment using the immune serum induced with the H1 HA monomer, H1 HA-PCNA1dm and the multivalent antigen PCNAdm-3HA proteins fused with H1, B, and H3 HA. Whether or not antibodies are formed in blood collected 4 days after viral infection from the time of antigen inoculation is determined based on the result of the calculation of plaque reduction neutralization titer (PRNT) after infecting MDCK cells after reaction with H1N1, H3N2 and B viruses for 1 hour (middle, bottom).

FIG. 14D shows antibody titers to H1 HA, H3 HA, and B HA trimers and monomers or mini-HA as antigens through ELISA using serum obtained from mice to which serum IP is transferred to determine whether or not antibodies are formed in mice administered mouse serum inoculated with influenza virus HA antigen. After an ELISA microplate is coated with 200 ng of each antigen overnight at 4° C., the collected serum is serially diluted and primary antibody binding is performed at 37° C. for 1 hour. ELISA is performed using a microplate and the absorbance of the secondary antibody-horseradish peroxidase reaction is measured at a wavelength of 450 nm. The groups are the same as in FIG. 14A.

FIG. 15A shows the challenge mouse animal experiment daily scheme of the X47 H3N2 subtype belonging to influenza virus group 2 using the HA monomer and scaffold multivalent antigens. Eight mice are used in each group (5 mice in the control naive group), the antigen substance is administered thereto twice at an interval of 2 weeks, and blood was collected after 0 weeks, 2 weeks, 4 weeks, and 4 weeks+4 days after antigen administration and priming, and viral infection is performed by intranasal administration. The total duration of the experiment is 42 days, and each group is as follows. Group 1: naive mice, Group 2: PBS buffer+adjuvant, Group 3: inactivated H3 X47+adjuvant, Group 4: commercial SK bioscience trivalent vaccine+adjuvant, Group 5: PCNA1dm-PCNA2dm-PCNA3dm assembled+adjuvant Bunt, Group 6: H3 HA monomer+ adjuvant, Group 7: H3 HA-PCNA3dm+adjuvant, Group 8: H1 HA, H3 HA, B HA mutant mixture+adjuvant, Group 9: PCNAdm-3HA+adjuvant.

FIG. 15B shows the results of the challenge mouse animal experiment daily scheme of the X47 H3N2 subtype belonging to influenza virus group 2 using the H1 HA monomer, H1 HA-PCNA1dm, and the multivalent antigen PCNAdm-3HA protein fused with H1, B, and H3 HA. The daily weight change (top) and survival rate (bottom) are shown in mice infected with the X47 (H3N2) virus. A commercial trivalent vaccine purchased from SK bioscience is used as a positive control, a reduction in mouse body weight of 20% or more is considered lethal, and each group is the same as in FIG. 13A.

FIG. 15C shows the virus titer (log PFU/ml) in lung tissue after sacrifice of mice 4 days after PR8 (H1N1) virus infection as the result of mouse animal experiments using the H1 HA monomer, H1 HA-PCNA1dm and the multivalent antigen PCNAdm-3HA protein fused with H1, B, and H3 HA (top) and antibody titers to H1, H3, B HA monomer, trimer, and mini HA as antigens in an ELISA experiment performed using serum collected from 4-day mice (bottom). After an ELISA microplate is coated with 200 ng of each antigen overnight at 4° C., the collected serum is serially diluted and primary antibody binding is performed at 37° C. for 1 hour. ELISA is performed using a microplate and the absorbance of the secondary antibody-horseradish peroxidase reaction is measured at a wavelength of 450 nm. The groups are the same as in FIG. 13A.

BEST MODE

Unless defined otherwise, all technical and scientific terms used herein have the same meanings as appreciated by those skilled in the field to which the present invention pertains. In general, the nomenclature used herein is well-known in the art and is ordinarily used.

Structural change of hemagglutinin proteins plays the most important role in the invasion of influenza virus into host cells through the mechanism of membrane fusion. In particular, hemagglutinin proteins maintain overall trimeric stability because the inherent instability of the stem is offset by capping the stem with the head. Over the past decade, universal vaccines have been developed to produce stem-specific antibodies through stable exposure of unstable stems. The present invention is based on the development of stable monomeric antigens capable of exposing the conserved sites from a different viewpoint from the prior art and thus the finding that the structural advantage of the monomer capable of exposing the interface better than the trimer causes great improvement in immune activity.

Specifically, in the present invention, in order to stabilize influenza virus hemagglutinin monomers, the following amino acid residue mutations are formed in H1 subtype, H3 subtype, and B type hemagglutinin proteins: monomers having five mutations of L73S, I77S, L80S, F88E, and V91W; monomers having five mutations of V73S, I77S, L80S, V84W, L91W in H3 HA; and monomers having eight mutations of L73S, I77S, L80W, V84W, L87S, T91W, L98S, and L102W in B HA are prepared and a disulfide bond mutation is formed as V20C-E105C/M320C-H111C in H1 HA and M320C-T111C in H3 HA, respectively. The final monomeric mutant protein with H1 HA five mutations and two disulfide bond mutations is represented by SEQ ID NO: 1, the final monomeric mutant protein with B HA eight mutations is represented by SEQ ID NO: 2, and the final monomeric mutant protein with H3 HA five mutations and one disulfide bond mutation is represented by SEQ ID NO: 3, and the monomeric properties thereof were confirmed.

Next, cell-based expression and animal experiments based on mice were performed using the influenza virus recombinant hemagglutinin monomeric protein singly or in combination thereof. As can be seen from the results of Examples below, the monomeric protein according to the present invention exhibits immune activity comparable to conventional commercially-available trivalent influenza vaccines and has a monomer-based structural advantage of being highly likely to induce formation of an antibody specific to the monomer-monomer interface site, which is difficult to expose with conventional trivalent influenza vaccines.

In one aspect, the present invention provides an antigen composition for preventing or treating viral infectious diseases containing, as an active ingredient, an influenza virus recombinant hemagglutinin monomeric protein represented by any one of SEQ ID NO: 1 to SEQ ID NO: 3.

The monomer monomeric protein represented by SEQ ID NO: 1 is H1 subtype influenza virus recombinant hemagglutinin having five protein mutations and two disulfide bond mutations, the monomeric mutant protein represented by SEQ ID NO: 2 is influenza B virus recombinant hemagglutinin having eight protein mutations, and the monomeric mutant protein represented by SEQ ID NO: 3 is H3 subtype influenza virus recombinant hemagglutinin having five protein mutations and one disulfide bond mutation.

According to the present invention, any one may be used as the virus as long as it infects humans and animals and for example, the virus may be selected from the group consisting of Orthomyxoviridae including influenza virus, transmissible gastroenteritis virus, porcine epidemic diarrhea (PED) virus, SARS, MERS, Coronavirus including SARS-CoV-2, zika virus, Flavivirus including bovine viral diarrhea (BVD) virus, Calicivirus including norovirus, respiratory syncytial virus (RSV), porcine respiratory reproductive syndrome (PRRS) virus, porcine circovirus type 2 (PCV2) virus, rotavirus, parvovirus, picornavirus, pestivirus, rhabdovirus, birnavirus, retrovirus and herpesvirus.

As used herein, the term. "prevention" or "treatment" refers to alleviation or amelioration of disease symptoms, reduction of disease ranges, delay or amelioration of disease progression, amelioration, alleviation or stabilization of disease states, partial or complete recovery, prolongation of survival, all other beneficial treatment results and the like.

As used herein, the term "composition" is intended to include any product obtained directly or indirectly by combining specific ingredients, in addition to a product including the specific ingredients.

The antigen composition according to the present invention may be applied in all known forms, such as pharmaceutical compositions administered to vertebrates, preferably mammals including humans, food compositions, and conventional prophylactic and therapeutic antiviral agents.

In the present invention, the antigen composition containing an influenza virus recombinant hemagglutinin monomeric protein represented by any one of SEQ ID NOs: 1 to 3 or a mixture thereof as an active ingredient is effective in preventing a variety of viruses, in particular, is highly effective in preventing influenza viruses belonging to the family Orthomyxoviridae.

Specifically, as can be seen from the following examples, animal experiments show that the mutant monomers exhibited immune activity comparable or superior to a PBS buffer solution or commercial trivalent influenza vaccine (from SK bioscience) used as a control group, and the immune activity of highly purified monomers present as a solution is considered to be directly related to the content of these recombinant proteins in the sample.

The influenza virus recombinant hemagglutinin monomeric proteins according to the present invention are effective in preventing or treating animal and human influenza by inhibiting the proliferation and replication of orthomyxovirus.

In the present invention, the orthomyxovirus is an influenza virus, but is not limited thereto.

In another aspect, the present invention provides an antigen composition for preventing or treating an orthomyxovirus infectious disease containing, as an active ingredient, an influenza virus recombinant hemagglutinin monomeric protein represented by any one of SEQ ID NO: 1 to SEQ ID NO: 3 or a combination thereof.

Influenza hemagglutinin monomers are purified protein antigens that may be easily mutated using the Bac-to-Bac system, may be easily expressed using insect cells sf9 and hi5 cells, and may be easily characterized after purification to a purity of 90% or more using column chromatography. Antigen protein mutations may be achieved by introducing (transfecting), into cells, the bacmid into which the target genes are accurately inserted through a selection process in bacteria, preferably in a Bac-to-Bac system. More preferably, the antigen proteins may be obtained by other genetic engineering methods.

The hemagglutinin proteins are more preferably proteins expressed in other cells including animals and bacteria in addition to sf9 and hi5 insect cells.

The purification of hemagglutinin proteins to a purity of 90% or more using a Ni-NTA affinity column, a Mono Q ion exchange column, and a Superdex gel filtration 200HR column chromatography enables easy characterization and production of hemagglutinin antigens derived from various influenza viruses. Highly pure proteins can be purified using other purification methods.

In particular, highly pure proteins can be prepared by purification in an active form using trypsin or degrading enzymes other than trypsin. The purification removes cell residuals or the like left in the extracts.

The pharmaceutical composition for preventing or treating an orthomyxovirus infectious disease according to an embodiment of the present invention contains each of the influenza virus recombinant hemagglutinin monomeric proteins represented by SEQ ID NOs: 1 to 3, a mixture thereof or a bond thereof to a scaffold molecule. In addition, the pharmaceutical composition may include a pharmaceutically acceptable carrier, excipient, or diluent according to a conventional method used in the art depending on the formulation, method of use, and application. In addition, the pharmaceutical composition may be administered as a single therapeutic agent or in combination with another therapeutic agent, and may be administered sequentially or simultaneously with conventional therapeutic agents.

The composition may be administered orally or parenterally depending on a conventional method, for example, when administered orally, and may be provided as a formulation such as a powder, granule, tablet, capsule, suspension, emulsion, syrup, or the like. The composition may be prepared in any commonly known form, such as in the form of a pharmaceutical composition administered to animals including birds, preferably animals including humans and birds.

The influenza virus recombinant hemagglutinin monomeric protein (or a mixture thereof) represented by any one of SEQ ID NO: 1 to SEQ ID NO: 3, a mixture thereof, or a mixture thereof with other components, as an active ingredient in the composition for preventing or treating orthomyxovirus infectious diseases, is present in an amount of 0.001 wt % to 99.9 wt %, preferably 0.1 wt % to 99 wt %, and more preferably 1% by weight to 50% by weight.

A preferred dosage may be an amount suitable for the treatment or prevention of a subject and/or disease, may be controlled and suitably selected depending on various factors including the age, gender, general health condition and weight of the subject, the type and severity of the disease, the type of formulation, the type and content of other ingredients, the secretion rate of the composition, the route and duration of administration, and the like, and is preferably 50 to 100 mg per day for an adult (70 kg).

In another aspect, the present invention provides a food composition for preventing or treating an orthomyxovirus infectious disease containing, as an active ingredient, an influenza virus recombinant hemagglutinin monomeric protein represented by any one of SEQ ID NO: 1 to SEQ ID NO: 3 or a combination thereof.

The food composition of the present invention may be in any herbal form suitable for administration to animals including humans, in any ordinary form suitable for oral administration, for example, solids such as food or feed, additives and adjuvants of food or feed, fortified food or feed, tablets, pills, granules, capsules and effervescent blends, or liquids, such as solutions, suspensions, emulsions, and beverages. In addition, the food composition may contain nutrients, vitamins, electrolytes, and the like, and these components may be used singly or in combination.

Antibiotics are effective only in secondary infections such as bacterial diseases because the orthomyxovirus infection is caused by a virus. Accordingly, the present inventors provide a composition containing the recombinant antigen protein as an active ingredient, thereby effectively preventing infection.

The present invention also provides an antigen composition for preventing or treating viral infectious diseases containing at least one fusion protein including a scaffold fragment and a recombinant antigen protein bound to the scaffold fragment.

Here, the fusion proteins (100, 200, 300) are present in plural and are different from each other, the respective scaffold fragments (110, 210 and 310) of the fusion proteins are self-assembled to form a cyclic scaffold, and the recombinant antigen proteins (120, 220, 320) are exposed to the outside of the cyclic scaffold (see FIG. 9).

In addition, the fusion protein includes the plurality of scaffold fragments different from each other and the plurality of recombinant antigen proteins different from each other.

Here, the first fusion protein 100, which is any one of the plurality of fusion proteins, includes the first scaffold fragment 110 represented by SEQ ID NO: 4 (referred to as "PCNA1dm" in the following Example) and the first recombinant antigen protein 120 (referred to as "H1 HA monomer mutant protein" in the following Example) which is bound to the first scaffold fragment 110 and is represented by SEQ ID NO: 1 (see FIG. 9).

Also, the second fusion protein 200, which is any one of the plurality of fusion proteins, includes the second scaffold fragment 210 represented by SEQ ID NO: 5 (referred to as "PCNA2dm" in the following Example) and the second recombinant antigen protein 220 (referred to as "B HA monomer mutant protein" in the following Example) which is bound to the second scaffold fragment and is represented by SEQ ID NO: 2 (see FIG. 9).

Also, the third fusion protein 300, which is any one of the plurality of fusion proteins, includes the third scaffold fragment 310 represented by SEQ ID NO: 6 (referred to as "PCNA3dm" in the following Example) and the third recombinant antigen protein 320 (referred to as "H3 HA monomer mutant protein" in the following Example) which is bound to the third scaffold fragment and is represented by SEQ ID NO: 3 (see FIG. 9).

Also, the first fusion protein 100, which is any one of the plurality of fusion proteins, includes the first scaffold fragment 110 represented by SEQ ID NO: 4 and the first recombinant antigen protein 120 which is bound to the first scaffold fragment 110 and is represented by SEQ ID NO: 1, the second fusion protein 200, which is any one of the plurality of fusion proteins, includes the second scaffold fragment 210 represented by SEQ ID NO: 5 and the second recombinant antigen protein 220, which is bound to the second scaffold fragment and is represented by SEQ ID NO: 2, and the third fusion protein 300, which is any one of the plurality of fusion proteins, includes the third scaffold fragment 310 represented by SEQ ID NO: 6 and the third recombinant antigen protein 320 which is bound to the third scaffold fragment and is represented by SEQ ID NO: 3 (see FIG. 9).

According to the present invention, the scaffold fragment may be a proliferating cell nuclear antigen (PCNA).

According to the present invention, the recombinant antigen protein may be an influenza virus recombinant hemagglutinin protein monomer mutant protein.

According to the present invention, any one may be used as the virus as long as it infects humans and animals and for example, the virus may be selected from the group consisting of Orthomyxoviridae including influenza virus, transmissible gastroenteritis virus, porcine epidemic diarrhea (PED) virus, SARS, MERS, coronavirus including SARS-CoV-2, Zika virus, Flavivirus including bovine viral diarrhea (BVD) virus, Calicivirus including norovirus, respiratory syncytial virus (RSV), porcine respiratory reproductive syndrome (PRRS) virus, porcine circovirus type 2 (PCV2) virus, rotavirus, parvovirus, picornavirus, pestivirus, rhabdovirus, birnavirus, retroviruses and herpesvirus.

The pharmaceutical composition according to the present invention includes a pharmaceutically acceptable carrier, excipient, or diluent according to a conventional method used in the art depending on the formulation, method of use, and application. In addition, the pharmaceutical composition may be administered as a single therapeutic agent or in combination with another therapeutic agent, and may be administered sequentially or simultaneously with conventional therapeutic agents.

The composition may be administered orally or parenterally depending on a conventional method, for example, when administered orally, and may be provided as a formulation such as a powder, granule, tablet, capsule, suspension, emulsion, syrup, or the like. The composition may be prepared in any commonly known form, such as in the form of a pharmaceutical composition administered to animals including birds, preferably animals including humans and birds.

The composition may contain the fusion protein in an amount of 0.001 wt % to 99.9 wt %, preferably 0.1 wt % to 99 wt %, more preferably 1 wt % to 50 wt %, based on the total weight of the composition.

A preferred dosage may be an amount suitable for the treatment or prevention of a subject and/or disease, may be controlled and suitably selected depending on various factors including the age, gender, general health condition and weight of the subject, the type and severity of the disease, the type of formulation, the type and content of other ingredients, the secretion rate of the composition, the route and duration of administration, and the like, and is preferably 50 to 100 mg per day for an adult (70 kg).

In addition, the present invention provides a food composition for preventing or treating viral infectious diseases containing at least one fusion protein including a scaffold fragment and a recombinant antigen protein bound to the scaffold fragment.

The food composition of the present invention may be in any herbal form suitable for administration to animals including humans, in any ordinary form suitable for oral administration, for example, solids such as food or feed, additives and adjuvants of food or feed, fortified food or feed, tablets, pills, granules, capsules and effervescent blends, or liquids, such as solutions, suspensions, emulsions, and beverages. In addition, the food composition may contain nutrients, vitamins, electrolytes, and the like, and these components may be used singly or in combination.

According to a preferred embodiment of the present invention, the present invention relates to a scaffold-based multivalent antigen composition having a structure in which stable mutant monomers of recombinant virus surface fusion proteins are bound to scaffold molecules. More specifically, the present invention relates to a universal antigen composition that contains, as an active ingredient, a multivalent antigen complex (refer to FIG. 9) formed by binding stable recombinant mutant monomers of influenza virus surface protein hemagglutinin to scaffold molecule proliferating cell nuclear antigens (PCNA), thereby exhibiting a preventive or therapeutic effect on diseases caused by a variety of mutant viral strains.

In addition, the multivalent antigen composition of the present invention is based on two base technologies. First, compared to the recombinant HA protein trimeric antigen, the monomeric antigen exhibits immune activity comparable to commercially available vaccines and is more effective in inducing a specific antibody response. Second, in terms of protein production, the monomer mutant protein has no problem of trimeric aggregation when fused to scaffolds, and exhibits improvement in properties such as stability and water solubility when assembled. Third, it takes time and effort to prepare stable monomer mutant proteins, but when the stability of the monomer is achieved, as a result, the highly conserved region epitope is more easily exposed and thus the value of the monomeric antigen as a universal antigen increases. In order to stabilize the influenza virus HA monomer, in the present invention, five or eight amino acid residues were mutated in each of the H1 subtype HA, B type HA, and H3 subtype HA proteins (H1 HA: L73S, I77S, L80S, F88E, and V91W; B HA: L73S, I77S, L80W, V84W, L87S, T91W, L98S, and L102W; H3 HA: V73S, I77S, L80S, V84W, L91W; represented by SEQ ID NOs: 1 to 3, respectively) and these mutant proteins were identified as monomers through characterization (see Example below).

The scaffold protein disclosed herein is a proliferating cell nuclear antigen (PCNA) derived from *Sulfolobus solfataricus* (Dionne et al., 2003) and various viral protein antigens can be bound to the N- or C-terminal of the scaffold protein. Up to six different antigens can be bound to the N- or C-terminal of the scaffold protein, and the scaffold protein, to which the HA antigen is fused, has a nanoparticle size of 30 to 40 nm, although the nanoparticle size depends on the size of the antigen. Based thereon, as described below, the result of animal experiments showed that immune activity was greatly improved. *S. solfataricus* PCNA proteins consist of PCNA1, PCNA2, and PCNA3 subunits (scaffold fragments), and after a dimer is formed by PCNA1 and PCNA2, PCNA3 is assembled to form a heterotrimer (Dionne et al., 2003). The PCNA heterotrimer is well assembled in a solution even when PCNA1, PCNA2, and PCNA3 are mixed at the same time (data not shown). In order to enhance electron transfer of *Pseudomonas putida* cytochrome P450 monooxygenase, ferredoxin, and ferredoxin reductase, the assembly of three PCNA-HA antigen fusion proteins was fused with each of PCNA3, PCNA2, and PCNA1, the fusions were assembled each other and the resulting complex functions to transfer protein electrons (Hirakawa and Nagamune, 2010). At this time, the electron transfer function of the complex was enhanced by increasing the length of the linkers (10, 16, and 3 amino acids in length, respectively) between the enzyme and PCNA to consider the flexibility of the fusion complex protein.

An assembly of H1 HA-PCNA1, B HA-PCNA2 and H3 HA-PCNA3 was not formed well in vitro using PCNA-HA bound with influenza antigen protein HA in the previous study. In order to increase assembly binding affinity, two mutations were performed at the interface where PCNA1, PCNA2, and PCNA3 interact with each other (T112K/ Y114K, S172V/A174V, and Y73F/S170V), and these results were called "PCNA1dm", "PCNA2dm", and "PCNA3dm", respectively (represented by SEQ ID NOs: 4 to 6). It was confirmed that binding between PCNA1 and PCNA2, and binding between PCNA3 and PCNA2 of the mutant protein was 3 to 5 times stronger than those of the wild-type protein (see the results below). Accordingly, the present inventors fused the stable HA monomer mutant proteins of recombinant H1, H3 subtype and B type into the scaffold PCNA protein mutant subunits, PCNA1dm, PCNA2dm, and PCNA3dm, respectively, and called the fusions "H1 HA-PCNA1dm", "B HA-PCNA2dm", and "H3 HA-PCNA3dm" (corresponding to respective fusion proteins, collectively called "HA-PCNAdm"), the assembled multivalent antigen was characterized using size exclusion chromatography and the final result was called "PCNAdm-3HA".

Structural change of hemagglutinin proteins plays the most important role in the invasion of influenza virus into host cells through the mechanism of membrane fusion. In particular, hemagglutinin proteins maintain overall trimeric stability because the inherent instability of the stem region is offset by capping the stem region with the head region. Conventional universal vaccine research has focused on producing specific antibodies to highly conserved stem regions through stable exposure of unstable stems. The present inventors developed stable monomeric antigens capable of exposing the conserved sites from a different viewpoint from the prior art and improved immune activity using the fusion proteins bound with the scaffold PCNA capable of binding to multivalent antigens (HA-PCNAdm and PCNAdm-3HA).

In the present invention, it was found that the antigen composition containing the fusion protein (HA-PCNAdm or PCNAdm-3HA) according to the present invention as an active ingredient has excellent antiviral efficacy against influenza viruses belonging to Orthomyxoviridae. The HA-PCNAdm and PCNAdm-3HA antigen compositions bound with various recombinant HA monomers exhibit better immune activity than the PBS buffer solution used as a control group in animal experiments or commercial trivalent influenza vaccines from SK bioscience, and the immune activity of HA-PCNAdm and PCNAdm-3HA protein antigens bound with high-purity recombinant HA monomers is directly related to the content of these recombinant protein antigens in the sample.

In the present invention, the HA-PCNAdm and PCNAdm-3HA multivalent antigens exhibit a preventive or therapeutic effect on animal and human influenza by inhibiting the proliferation and replication of orthomyxovirus, and the orthomyxovirus is an influenza virus, but is not limited thereto. This is mainly because, most viruses such as coronavirus, human pneumovirus, and paramyxovirus, in addition to influenza virus, have trimer-type surface proteins very similar to HA, and surprisingly, the structural change from prefusion to postfusion required for host entry also depends on a very similar mechanism. Therefore, monomer forms of the surface proteins of various viruses may be prepared and developed as PCNA scaffold-based multivalent antigens.

Influenza virus-derived HA monomer mutant proteins, fusion proteins in which the PCNA is fused with each mutant protein (HA-PCNAdm), and fusion proteins formed by self-assembly of PCNA (PCNAdm-3HA) may be prepared using a Bac-to-Bac system and may be easily expressed using insect cells sf9 and High Five cells. The antigen proteins can be produced by selecting the bacmid, into which the target gene is accurately inserted, through a selection process in bacteria using the Bac-to-Bac system and then infecting the cells with the bacmid. In addition, the antigen proteins may be produced by other genetic engineering methods and may be expressed by transfecting genes into other cells including animals, plants and bacteria, in addition to sf9 and High Five insect cells.

The HA monomer, each of HA-PCNAdm and PCNAdm-3HA protein antigens were purified to a purity of 90% or more using a Ni-NTA affinity column, a Mono Q ion exchange column and a Superdex gel filtration 200HR column chromatography, and are easily characterized and then produced into HA antigen proteins derived from various influenza viruses that will occur in the future. Highly pure proteins can be purified using other purification methods. In particular, highly pure proteins can be prepared by purification in an active form using trypsin or degrading enzymes other than trypsin. The purification removes cell residuals or the like left in the extracts.

Antibiotics are ineffective unless the viral infection is a secondary infection problem such as a bacterial disease. Accordingly, the present inventors provide a composition containing HA-PCNAdm and PCNAdm-3HA proteins fused with the recombinant HA monomer as active ingredients, thereby effectively preventing infection.

MODE FOR INVENTION

Example

Hereinafter, the present invention will be described in more detail with reference to examples. However, it will be obvious to those skilled in the art that these examples are provided only for illustration of the present invention, and should not be construed as limiting the scope of the present invention. Accordingly, the substantial scope of the present invention is defined by the appended claims and equivalents thereto. All technical and scientific terms used herein have the same meanings as appreciated by those skilled in the field to which the present invention pertains. In general, the nomenclature used herein is well-known in the art and is ordinarily used.

Example 1: Influenza Virus-Derived Hemagglutinin Monomer and Design and Preparation of Mixture Thereof 1-1: Preparation of Structure-Based Hemagglutinin Monomer Protein 1-1-1: Influenza Virus Hemagglutinin Monomer The present inventors have identified the tertiary structure of 2009 pandemic influenza A/Korea/01/2009 (KR01) HA and HA-Fab complex, and the identified structure is not a conventional trimeric structure, but is a monomeric structure having a monomer-monomer interaction (Cho K J et al., 2013. J Gen Virol, 64, 1712-1722; Cho K J et al., 2014. PLoS One. 9, e89803). The present inventors suggested that, since the 2009 pandemic virus hemagglutinin protein had a monomeric structure in which the head region is relaxed from the stem region and is much more flexible, it could structurally facilitate membrane fusion, the role of the hemagglutinin molecule, and considered the membrane fusion as one of the molecular mechanisms of the pandemic virus that could infect a number of people. Since hemagglutinin trimers have evolved to have the appropriate stability until they begin to infect humans and animals through membrane fusion at an acidic pH, the monomers are much less stable than trimers and in fact, the denaturation transition temperature of the monomers is lower than that of the trimers (below).

Considering the fact that the development of influenza universal vaccines is made in an effort to expose, as epitopes, highly conserved amino acid moieties, such as hemagglutinin (mini-HA) having no head region, chimeric HA, and nanoparticles having only stem regions on molecular scaffolds, other universal vaccines are expected to be developed based on the characteristics of the monomers. That is, the trimer has a hidden monomer interface having the monomer-monomer interaction, whereas the monomer has an exposed highly conserved interface. In addition, in the trimer, it is difficult to expose the stem region for antibody induction and the immune response of this region is immunosubdominant, whereas in the monomer, antibody accessibility is relatively easy, since the interface region is exposed. Antibodies that recognize the hemagglutinin trimer interface have been found (Watanabe A. et al., 2019. Cell 177: 1124-1135; Bangaru S. et al., Cell 177: 1139-1152; Bajic G. et al., Cell Host & Microbe 25: 1-9), and the fact that these antibodies have very universal protection indicates the importance of the interface as a highly conserved epitope.

In addition, since the monomer has most of the epitope of the trimer, there is no significant difference in the antibody recognition between the monomer and the trimer (there is no great difference in the dissociation constant $K_D$ indicating antibody binding affinity), and the substrate specificity is the same. Although some papers reported that a trimer is necessary because a part of the monomer-monomer interface of the trimer acts as an epitope, an antigen-antibody reaction having a part of the interface of the trimer as an epitope does not have a great difference even if there is no interface (Cho K J et al., 2013. J Gen Virol, 64: 1712-22; Magadan J G. et al., 2013. J. Virol. 87: 9742-9753).

1-1-2: Structure-Based Hemagglutinin Monomer Design

Hemagglutinin has a stabilized trimeric form and amino acid mutation is required to produce hemagglutinin as a monomeric form. The present inventors selected six amino acid residues involved in monomer-monomer interaction inside the trimer from the seasonal mutant A/Thailand/CU44/2006 (CU44) HA gene, which has a trimeric structure in consideration of the fact that the trimer-monomer transformation should be generally applied to various viruses, and changed charges or sizes thereof. Thereamong, mutations of two amino acid residues (F88E, V91W) inhibited the formation of trimers, thereby successfully forming a monomer (Seok J H et al., 2017. Sci. Rep. 7: 7540). However, the produced monomer is much less stable because the trimer is destabilized and thus dissociated.

In an attempt to solve the problem of the preparation of monomers by dissociation of influenza virus hemagglutinin trimers, the present invent ion focused on mutations of the monomers to stabilize the monomers. Structure-based analysis was performed on amino acid residues that are disposed at the hemagglutinin protein monomer-monomer interface and are exposed to the outside when they become monomers. Protein solubility and stability were improved by changing hydrophobic amino acid residues exposed to the outside to hydrophilic residues. That is, in addition to conventional two amino acid mutations (F88E and V91W), L73S, I77S, and L80S mutations, among various mutations, were further performed using point mutation, to produce a mutant protein having five mutations in the H1 subtype hemagglutinin protein (A/California/04/2009 (H1N1) (CA09) H1 HA: L73S, I77S, L80S, F88E, V91W) (FIG. 1A). In particular, the L73S mutation caused a great increase (5 to 10 times) in expression compared to conventional wild type proteins, and two disulfide bond mutations of V20C-E105C and M320C-H111C were performed. The conventional double mutant protein was derived from the CU44 virus in 2006, but the present invention targeted CA09 as H1 HA since the CA09 virus changed from a pandemic mutant to a seasonal mutant after the 2009 swine flu pandemic. Also, for each of H3 HA and type B HA, mutant proteins having five and eight mutations, were prepared: A/Gyeongnam/684/2006(H3N2) (Gy684): V73S, I77S, L80S, V84W, L91W), and M320C-T111C disulfide bond mutation, B/Florida/4/2006 (FL04) B HA: L73S, I77S, L80S, V84W, L87S, T91W, L98S, and L102W (FIG. 1C). Furthermore, mutant proteins were prepared by forming disulfide bond mutations, that is, V20C-E105C/M320C-H111C for H1 HA and M320C-T111C for H3 HA. The amino acid sequences of these influenza virus recombinant H1 HA, H3 HA, and B HA protein mutant monomers are shown in FIGS. 1A, 1B, and 1C.

A his-tag (6×His-tag) and a foldon domain were attached to the 5' end and the 3' end, respectively, together with a thrombin cleavage site for each construct, the result was injected into a transfer vector, and each hemagglutinin mutant protein was designed to select the bacmid into which the correct target gene was inserted through a bacterial selection process (FIG. 1C). The trimer is converted into the monomer and stability is secured because the foldon domain is cut off due to proteolytic cleavage when the mutant protein is expressed, purified and treated with thrombin.

1-2: Production of Influenza Virus Hemagglutinin Monomer

Influenza virus recombinant hemagglutinin mutant monomers were expressed using insect cells sf9 and a Bac-to-Bac system using High Five. For viral proteins in insect cells, conditions for expressing proteins having optimal yield and solubility were set through small-scale experiments, viral proteins were cloned in pFastBac vector, and recombinant bacmid DNAs are produced in DH10Bac. The recombinant bacmid DNAs were transfected into sf9 cells using Cellfectin and incubated for 2 to 3 days to produce virus, the virus was serially amplified in sf9 cells and stored in a refrigerator. High Five cells were injected with the virus, the multiplicity of infection (MOI) (the amount of inoculated virus/the number of cells) of the construct whose expression was confirmed was adjusted using P3 baculoviral stock, and then incubated at 27° C. for 3 days. The cell pellet was removed by centrifugation and the protein-secreted supernatant was collected.

The supernatant expressed in insect cells was concentrated using a Centramate Lab Tangential Flow Filtration (TTF) system and then the expressed CA09, Gy684, and FL04 HA mutant monomers were each consecutively purified in three steps using the AKTA BASIC chromatography system. Purification was performed to a purity of 90% or more using a Ni-NTA affinity column, a Mono Q ion exchange column, and a Superdex 200HR gel filtration column chromatography (FIGS. 2A, 2B and 2C).

In order to analyze the specificity of the stem region, not the head region of hemagglutinin, in the antigen-antibody reaction of H1 subtype, H3 subtype, and B type hemagglutinin mutation monomers, mini-HA (#4900 construct-stem HA; Impagliazzo A et al., 2015. Science 349: 1301-1306) protein nucleotide sequences consisting of only the stem region were synthesized and then expressed using insect cells sf9 and High Five. Continuous purification was performed using the AKTA BASIC chromatography system, and binding of the antibody of the C179 stem region as a control group was observed in a concentration-dependent manner (FIG. 8C, middle, bottom).

Example 2: Influenza Mutant Virus Hemagglutinin Monomer Properties 2-1: Characteristics of Influenza Virus Hemagglutinin Mutation Monomer Characterization of each viral hemagglutinin mutant monomer was performed on the proteins that have been mass-expressed and purified. CA09, Gy684, and FL04 hemagglutinin mutant monomers to improve the stability of hemagglutinin monomers were each purified, cleaved with thrombin, and then characterized through denaturation electrophoresis (SDS-PAGE) (FIGS. 2A, 2B and 2C). By measuring the exact molecular size of each virus hemagglutinin mutant protein through gel filtration chromatography and multi-angle light scattering, it was confirmed that each protein existed as a monomer (FIGS. 2A, 2B and 2C). This indicates that the selected mutation in the hemagglutinin protein contributes to dissociation of the trimer and the stability of the monomer. In addition, the result of differential scanning fluorescence showed that the denaturation transition temperature indicating the stability of the H1 hemagglutinin mutant monomer was 4° C. higher than that of the previously reported double mutant protein (Seok J H et al. 2017. Sci. Rep. 7: 7540), which indicates that it contributed to improvement in the stability as well as the expression yield of the monomer (FIGS. 3A and 3B). However, the fact that the transition temperature is still lower than that of the trimer suggests that more mutations may be required to obtain a monomer because the hemagglutinin protein is originally a stable trimer. In addition, it was confirmed that there was no great difference in seasonal viral hemagglutinin protein protomers.

It is considered that the industrial application value is high if the monomer-monomer interface, which is difficult to expose in the trimer, can be exposed, and the immune activity can be increased by utilizing a stable hemagglutinin-mutated monomer. That is, the monomeric hemagglutinin protein does not need to be restricted by trimer symmetry when preparing a scaffold protein such as VLP compared to the trimer, and it does not cause problems of solubility and protein aggregation and can be stably present as a fusion protein, thus having an advantage of being easily introduced into nanoparticles. In particular, the monomer is considered to be a beneficial substance for the development of universal vaccines that can overcome a low vaccination effect caused by various subtypes of the virus in the development of influenza virus vaccines requiring transfection of various viral antigens.

In order to perform animal experiments to determine the value of respective recombinant hemagglutinin mutant monomers and the mixture of these monomers as antigens, the expression size was expanded to enable mass purification in mg units, and mouse animal experiments were performed to verify immune activity against influenza virus.

Example 3: Recombinant Hemagglutinin Mutation Monomer Animal Experiment 3-1: Hemagglutinin Mutation Monomer Antigen-Based Animal Experiment In accordance with the daily scheme for mouse animal experiments, 8-week-old BALB/c mice were subcutaneously injected with hemagglutinin mutant monomers, etc. at 2-week intervals, and injected at $5 LD_{50}$ ($5 \times 10^2$ PFU/mouse) with the PR8 virus (mouse acclimated A/PuertoRico/8/34 virus: PR8) from the Center for Disease Control and Prevention and the vaccine efficacy was evaluated (FIG. 4). Mice used for animal experiments were classified into a total of 5 groups, PBS buffer and SAS adjuvant were used for a control group, and respective groups are as follows. Group 1: naïve mice, Group 2: PBS buffer+adjuvant, Group 3: H1 (CA09) hemagglutinin mutant monomer+adjuvant, Group 4: commercially available trivalent vaccine from SK bioscience, and Group 5: mixture of H1, H3, B hemagglutinin mutant monomers+adjuvant. The adjuvant used herein was the Sigma adjuvant system (S6322) from Sigma-Aldrich. Vaccine efficacy was evaluated by measuring changes in body weight and survival rates in mice infected with PR8 virus.

From the results of changes in body weight and survival rate, it is noteworthy that the H1, H3, and B hemagglutinin mutant monomer mixture mouse group exhibited survival rates very similar to those in the naïve mouse group (FIG. 5). The mouse group vaccinated with the commercially available trivalent vaccine from SK bioscience and the hemagglutinin mutant monomer group were linked next to the mutant monomer mixture group in terms of survival (FIG. 7). The control group, the mouse group not injected with the hemagglutinin antigen, was observed to lose 20% or more in body weight over 6-7 days. A reduction in body weight of 20% or more indicates the end of an ethical and humane experiment in animal testing. Interestingly, all of the hemagglutinin mutant monomer mixture group, the commercially available SK bioscience trivalent vaccine group, and the hemagglutinin mutant monomer group exhibited a 10-15% decrease in weight from the initial 6-8 days, but an increase in survival rate after 7-8 days, whereas Group 1 of mice not injected with the antigen exhibited a weight change of 20% or more, and a great decrease in the survival rate. Therefore, it was found that the hemagglutinin mutation monomer mixture group, the commercial SK Chem trivalent vaccine group, and the hemagglutinin mutation monomer group were superior in this order in terms of weight change and survival rate changes. As descried above, the mixture group of hemagglutinin mutant monomers showed a 100% survival rate, the mouse group vaccinated with commercial SK bioscience trivalent vaccine showed an 80% survival rate, and the hemagglutinin mutant monomer group showed a 40% survival rate. The immune activity against the antigen of these groups is noteworthy. The mutant proteins and a mixture group thereof according to the present invention exhibited an increase in weight gain and survival rate comparable to or superior to that of the commercial SK bioscience trivalent vaccine group, which indicates that the technical value thereof was high.

3-2: Analysis of Virus in Animal Experiment Mouse Lung Tissue

After virus infection, changes in body weight and survival rate were observed for 2 weeks. On the $3^{rd}$ day of infection, 3 animals per group were sacrificed, virus was extracted from lung tissue in PBS buffer, and then infected with MDCK (Madin-Darby canine kidney) cells, and virus concentration (titer) was calculated. In detail, a mouse was sacrificed 3 days after infection with influenza virus to obtain lung tissue, the lung tissue was homogenized using a tissue homogenizer, and then centrifuged (4,000×g) at 4° C. for 5 minutes to obtain a supernatant. MDCK cells were infected with 500 μl of the lung tissue supernatant diluted at 1:10 for 3 hours. After infection, the lung tissue supernatant was removed, and the cells were washed 3 times using PBS and incubated in Eagle's medium (DMEM, Gibco BRL, Karlsruhe, Germany) supplemented with 1 μg/ml TPCK-treated trypsin and 1% agarose in a 37° C. and 5% carbon dioxide incubator for 72 hours. After incubation, the cells were stained with 0.5% (v/v) crystal violet, a plaque reduction assay was performed and the results were measured.

The result of lung tissue virus analysis showed that, compared to the control PBS buffer group that was not administered with an antigen, among the PR8 virus-infected experimental groups, the hemagglutinin mutant monomer mixture group, the commercial SK bioscience trivalent vaccine group, and the hemagglutinin mutation monomer group exhibited a virus reduction in this order, and in particular, the hemagglutinin mutation monomer mixture group showed a difference of 2.0 log or more (FIG. 6). The results of the groups in the changes of body weight and survival rate were consistent with the results of the reduction rate of influenza virus titer in lung tissue.

3-3: Animal Test Serum Analysis 3-3-1: Plaque Reduction Neutralization Assay

The mouse serum sample was diluted at 1:10 and 1:40 and put in an Eppendorf tube, and the PR8 virus was added at a ratio of 9:1 (v/v) to the diluted mouse serum sample, followed by performing reaction for 60 minutes. The reacted virus-diluted mouse serum sample was added to MDCK cells and infection was induced in a 37° C. and 5% carbon dioxide incubator for 60 minutes. After infection, the virus-diluted mouse serum sample was removed, the cells were washed 3 times with PBS, and incubated in Eagle's medium (DMEM, Gibco BRL, Karlsruhe) supplemented with 1 μg/ml TPCK-treated trypsin and 1% agarose, Germany) in a 37° C. and 5% carbon dioxide incubator for 72 hours. After incubation, the cells were stained with 0.5% (v/v) crystal violet and the number of plaques was measured.

The result of the lytic plaque neutralization analysis showed that among the PR8 virus-infected experimental groups, all of the hemagglutinin mutant monomer mixture group, the commercial SK bioscience trivalent vaccine group, and the hemagglutinin mutant monomer group exhibited a significant plaque reduction compared to the control, PBS buffer group. In the case of H1N1 virus, the commercial SK bioscience trivalent vaccine group showed a great decrease, in the case of H3N2 virus, the commercial SK bioscience trivalent vaccine group and the mutant monomer mixture group showed a great decrease, and in the case of B virus, the hemagglutinin mutant monomer mixture group showed a great decrease (FIG. 7). Although there are differences depending on the subtype of influenza virus used in the experiment, the hemagglutinin mutant monomer mixture group, the commercial SK bioscience trivalent vaccine group and the hemagglutinin mutant monomer group exhibited a great neutralization reduction.

3-3-2: Mouse Serum Antibody Titer Analysis

In order to determine whether or not antibodies are formed in the blood after virus infection from the time of antigen inoculation in an animal experiment, orbital blood collection was performed and the antibody titer to each virus antigen protein was measured by ELISA. A hemagglutinin antigen derived from each strain virus was immobilized in the microplate and then binding was induced based on the interaction of the antibody with the antigen induced in the serum. Serum from each group was used for primary antigen-antibody reaction and a secondary antibody conjugated with horseradish peroxidase was used. Reaction between the antibody and the antigen in the serum was induced. 100 μl of TMB (3,3', 5,5'-tetramethylbenzidine, Sigma-Aldrich, St. Louis, MO) was added and the color was developed at room temperature for 10 minutes. The reaction was stopped and absorbance was measured at a wavelength of 450 nm through a microplate reader (Molecular Devices, Spectra-Max 190, Sunnyvale, CA).

The result of ELISA showed that the hemagglutinin mutated monomer group had a high antibody titer to the H1 hemagglutinin monomer, and all of the hemagglutinin mutant monomer mixture group, the commercial SK bioscience trivalent vaccine group and the hemagglutinin mutant monomer group exhibited a significant increase in the antibody titer to the H1 hemagglutinin trimer (FIG. 8A). In addition, all of the hemagglutinin mutant monomer mixture group, the commercial SK bioscience trivalent vaccine group and the hemagglutinin mutant monomer group exhibited higher H3 and B hemagglutinin antibody titers (FIG. 8B). In particular, the hemagglutinin mutant monomer mixture group exhibited a very high B-type hemagglutinin antibody titer, which was much higher than that of the commercial SK bioscience trivalent vaccine group or the hemagglutinin mutant monomer group. Naturally, the monomer mixture group has a higher B-type hemagglutinin antibody titer than that of the monomer group and has a higher B-type hemagglutinin antibody titer than that of the commercial SK bioscience trivalent vaccine group, which supports that the monomer has high technical potential. Although antibody titers have been tested to date depending on hemagglutinin-head region-specific antibodies or hemagglutination inhibitory reactions, recently, as molecular mechanisms controlling viruses have been reported through stem region-specific antibodies and antibody-dependent cell-mediated cytotoxicity (ADCC) analysis (DiLillo D J et al., 2014. Nat Med. 20: 143-151), concerns about conventional antibody titers that depend only on specific head region of hemagglutinin have arisen. Therefore, the correlation of the group having a high survival rate will be investigated through anti-stem antibody titer analysis in more detail.

3-3-3: Serum Anti-Stem Antibody Titer Analysis

In order to select the titer of the antibody that specifically reacts with the stem region rather than the head region based on the antibody titers to each virus antigen protein evaluated by ELISA using mouse serum obtained through orbital blood sampling in animal experiments, mini-HA (#4900 construct-stem HA) was used. mini-HA having only the stem region, instead of the hemagglutinin antigen derived from each strain virus in the microplate, was immobilized and then binding was induced based on the interaction of the antibody with the antigen in the serum. Serum from each group was used for the primary antigen-antibody reaction and a secondary antibody conjugated with horseradish per-oxidase was used. Color was developed with TMB at room temperature, the reaction was stopped and absorbance was measured at a wavelength of 450 nm through a microplate reader.

The stem region-specific antibody titer was significantly high in the hemagglutinin mutant monomer mixture group, the commercial SK bioscience trivalent vaccine group, and the hemagglutinin mutant monomer group (FIG. 8C) and the monomer group and the monomer antigen mixture group exhibited stem-specific antibody titers comparable to that of the commercial SK bioscience trivalent vaccine group. When the stability of the hemagglutinin monomer is equivalent to that of the hemagglutinin trimer, it is considered that further improved results can be obtained.

Example 4: Preparation of HA-PCNAdm and PCNAdm-3HA Antigen Proteins in which Influenza Virus-Derived HA Monomer Mutant Protein is Fused with PCNA 4-1: Structure-Based HA Monomer Protein Preparation
4-1-1: Significance of Influenza Virus HA Monomer In the prior art, the tertiary structure of the 2009 pandemic influenza A/Korea/01/2009 (KR01) HA and HA-Fab com-plex showed that HA is not a trimeric structure but is a monomeric structure having a monomer-monomer interac-tion (Cho et al., 2013; 2014). The HA protein has been suggested as a pandemic virus that can structurally facilitate membrane fusion due to the monomeric structure in which the head region is relaxed from the stem region and is much more flexible (Cho et al., 2013; 2014). A trimer has a hidden monomer interface having the monomer-monomer interac-tion, whereas a monomer has an exposed highly conserved interface. A trimer has been considered to be required as an antigen because a part of the monomer-monomer interface of the trimer acts as an epitope. However, since the HA monomer has most of the epitope of the trimer, there is no significant difference in the antibody recognition between the HA monomer and the trimer (there is no great difference in the dissociation constant $K_D$ indicating an antibody bind-ing affinity), and the substrate specificity is the same. There-fore, an antigen-antibody reaction having a part of the interface of the trimer as an epitope does not have a great difference even if there is no interface (Magadan et al., 2013; Cho et al., 2013).

4-1-2: Structure-Based HA Monomer Design

Influenza virus HA monomer is less stable than a trimeric structure. Structure-based analysis was performed on amino acid residues that are disposed at the monomer-monomer interface and are exposed to the outside. As a result, stable monomeric mutant proteins that have five mutations in H1 HA (A/California/04/2009(H1N1):L73S, I77S, L80S, F88E, V91W), five mutations (A/Gyeongnam/684/2006 (H3N2): V73S, I77S, L80S, V84W, and L91W) in H3 HA, or eight mutations (B/Florida/4/2006: L73S, I77S, L80W, V84W, L87S, T91W, L98S, and L102W) in B HA, and are capable of forming two V29C/E105C and M320C/H111C disulfide bonds in H1 HA and one M320C/T111C disulfide bond in H3 HA, respectively, were designed (FIGS. 10A and 10B).

A his-tag (6×His-tag) and a foldon domain were attached to the 5' end and the 3' end, respectively, together with a thrombin cleavage site for each construct, the result was injected into a transfer vector, each HA mutant protein was designed using a Bac-to-Bac system, and the bacmid, into which the correct target gene was inserted, was selected through a bacterial selection process (FIG. 1C). This aims at improving the stability before the foldon domain is cut off due to proteolytic cleavage after the protein is expressed in inset cells and purified (FIG. 10A, bottom).

4-1-3: Preparation and Characterization of PCNAdm

In order to improve the in vitro assembly of respective subunit proteins, PCNA1, PCNA2, and PCNA3 to forma scaffold PCNA heterotrimer derived from *S. solfataricus*, mutant proteins containing amino acid residue mutations located at the PCNA1-PCNA2- or PCNA2-PCNA3-binding interface were designed. Two mutations were performed on PCNA1, PCNA2, and PCNA3, to design T112K/Y114K, S172V/A174V, and Y73F/S170V mutant proteins, respec-tively (FIG. 10C).

PCNA wild-type subunits, PCNA1, PCNA2, and PCNA3, and mutant subunits, PCNA1dm, PCNA2dm, and PCNA3dm were expressed in *E. coli* bacterial cells and purified to obtain highly pure protein subunits (FIGS. 11A and 11B). In order to compare the PCNA assemblies, the binding kinetic constants $k_a$ and $k_d$ and the binding constant $K_D$ of PCNA1dm-PCNA2dm and PCNA2dm-PCNA3dm were calculated in a concentration range of 50 to 1,000 nM using the Bio-layer interferometer (BLI) Blitz system (ForteBio, Menlo Park, CA, U.S.A.) (FIG. 11C). The result showed that the mutant PCNA exhibited 3 to 6-fold improvement in binding compared to the wild-type PCNA.

4-2: Production of Influenza Virus HA-PCNAdm Antigen and Multivalent Antigen PCNAdm-3HA In the next step, H1 subtype CA09 HA, B type FL04 HA, and H3 subtype Gy684 HA monomer mutant protein genes were bound to PCNA1dm, PCNA2dm, and PCNA3dm, respectively. The H1, B, and H3 virus-derived HA genes had five or eight mutations, and GP67 signal sequences were disposed at the 5' end and was expressed outside the cells, and were bound to the N-terminal of each of PCNA1dm, PCNA2dm, and PCNA3dm (FIGS. 10A and 10B). Each HA gene was linked to PCNA through an SGG linker to produce a fused construct and His-tag was used for each construct for easy purification.

H1 HA-PCNA1dm, B HA-PCNA2dm, and H3 HA-PCNA3dm recombinant proteins, to which CA09, Gy684, and FL04 HA mutant proteins with improved mono-mer stability are fused, respectively, were expressed in a Bac-to-Bac system using insect cell sf9 and High Five. After cloning into the pFastBac vector, recombinant bacmid DNAs were produced in DH10Bac. sf9 cells were trans-fected with Cellfectin and incubated for 2 to 3 days to produce virus, and then the virus was amplified and stored in a refrigerator. High Five cells were injected with the virus, the multiplicity of infection (MOI) (the amount of inocu-lated virus/the number of cells) of the construct whose expression was confirmed was adjusted using P3 baculoviral stock, and then incubated at 27° C. for 3 days. The cell pellet was removed by centrifugation and the protein-secreted supernatant was collected. Recombinant proteins, H1 HA-PCNA1dm, B HA-PCNA2dm, and H3 HA-PCNA3dm were each purified using an AKTA BASIC chromatography system. The proteins were purified to a purity of 90% or more using Ni-NTA affinity, Mono Q ion exchange, and Superdex 200HR size exclusion chromatography (FIG. 12A, top). After protein purification, the H1 HA-PCNA1dm and B HA-PCNA2dm proteins were first incubated, and then the H3 HA-PCNA3dm protein was incubated to induce assembly and to thus prepare a fusion multivalent antigen PCNAdm-3HA protein (FIG. 12A, bottom). To analyze the specificity of the stem region, not the HA head region, in the antigen-antibody reaction, a mini HA (#4900 construct-stem HA) protein consisting of only the stem region was synthesized with reported nucleotide sequences and then insect cells sf9 and High Five were expressed using the AKTA BASIC chromatography system, and were continuously purified using an AKTA basic chromatography system (data not shown).

Example 5: Properties of Monomeric Fusion HA-PDNAdm and Multivalent Antigen PCNAdm-3HA 5-1: Properties of HA-PCNAdm and PCNAdm-3HA Antigen Proteins The expressed and purified H1 HA-PCNA1dm, B HA-PCNA2dm, and H3 HA-PCNA3dm recombinant complex proteins were subjected to size exclusion chromatography-multi-angle light scattering (SEC-MALS). As a result, the molecular weights of H1 HA-PCNA1dm, B HA-PCNA2dm and H3 HA-PCNA3dm complex proteins were 103.8, 89.9, and 133.2 kDa, respectively (FIG. 12B). In addition, the molecular weight of PCNAdm-3HA formed by assembly of each of the H1 HA-PCNA1dm, B HA-PCNA2dm, and H3 HA-PCNA3dm complex proteins was 326.3 kDa. When the assembled PCNAdm-3HA was observed using a transmission electron microscope negative staining-based 2D averaging method, the PCNAdm-3HA heterotrimer had an average particle with a size of 20 to 30 nm, indicating well-formed assembly (FIG. 12C). It is considered that the mutant monomer HAs with improved stability were fused with the PCNAdm heterotrimer.

5-2: Single Toxicity Test of PCNA Scaffold

For the single toxicity test, 20-200 μg/350 μl of the assembled PCNA1-PCNA2-PCNA3 or PCNA1dm-PCDNA2dm-PCNA3dm protein was administered once to acclimated 8-week-old BALB/c mice by intramuscular injection and the body weight thereof was measured daily for 7 days to analyze in vivo toxicity. The result of the single toxicity test showed that wild and mutant PCNA scaffolds had no toxicity in the concentration range of 20-200 μg/350 μl (data not shown).

Example 6: Animal Experiment Using Multivalent Antigen PCNAdm-3HA Antigen: Group 1 PR8 (H1N1) Virus Challenge 6-1: HA Mutant Monomer and Multivalent Antigen PCNAdm-3HA Antigen-Based Animal Experiment In accordance with the daily scheme for mouse animal experiment, 5-week-old BALB/c mice were subcutaneously injected with the HA monomer, HA-PCNAdm antigen, PCNAdm-3HA multivalent antigen, and the like at 2-week intervals, and injected with the PR8 virus (mouse acclimated A/PuertoRico/8/34 virus: PR8) from the Center for Disease Control and Prevention at 5 $LD_{50}$ ($5\times10^2$ PFU/mouse) and the vaccine efficacy was evaluated (FIG. 13A). Mice used for animal experiments were classified into a total of 8 groups, PBS buffer and SAS adjuvant were used for a control group, and respective groups are as follows. Group 1: naïve mice, Group 2: PBS buffer+adjuvant, Group 3: PCNA1-PCNA2-PCNA3 assembled+adjuvant, Group 4: H1 HA monomer+adjuvant, Group 5: H1 HA-PCNA1dm+adjuvant, Group 6: commercially available SK bioscience trivalent vaccine, Group 7: H1 HA, H3 HA, B HA mutant monomer mixture+adjuvant, Group 8: H1 HA, H3 HA, B HA trimer mixture+adjuvant, and Group 9: multivalent antigen PCNAdm-3HA+adjuvant. The adjuvant used herein was the Sigma adjuvant system (S6322 SAS) purchased from Sigma-Aldrich. Vaccine efficacy was evaluated by measuring changes in body weight and survival rates in mice infected with PR8 virus. In the animal experiment, a reduction in body weight of 20% or more indicates the end of an ethical and humane experiment.

The mice of PR8 virus-infected experimental groups, namely, H1 HA-PCNA1dm, H1, H3, B HA trimer mixture, H1, H3, B HA monomer mixture, and PCNAdm-3HA groups, exhibited an increase in body weight and 60% survival rate after 7 to 8 days compared to mice not administered the antigen (G2) (FIG. 13B). However, the H1 HA monomer and SK bioscience trivalent group mice exhibited 40% and 20% survival rates. The control group, which was Group 2, PBS buffer solution not administered with the HA antigen, decreased by more than 25% over 7 days.

It is considered that all mouse groups exhibited a great reduction in body weight in animal experiments because new anesthetics were administered thereto due to the strict regulation of the purchase of anesthetics. Nevertheless, the H1 HA-PCNA1dm, PCNADM-3HA multivalent antigen and H1 HA, H3 HA, and B HA monomer mixture groups were found to exhibit greater weight gain and increased survival rate in this order as compared to commercial SK vaccine groups.

6-2: Virus Analysis in Mouse Lung Tissue

Four days after the virus infection, three mice for each group were sacrificed, the virus was extracted from the PBS buffer solution from the lung tissue, MDCK (Madin-Darby Canine Kidney) cells were injected with the virus, and the viral concentration (titer) was calculated. The lung tissue was homogenized and then the supernatant was obtained by centrifugation (4,000×g) at 4° C. for 5 minutes. 500 μL of the supernatant was added at 1:10 to MDCK cells, followed by inducing infection for 3 hours. The supernatant was removed, and the cells were washed 3 times with PBS, and incubated in EAGLE's medium supplemented with 1 μg/ml TPCK-treated trypsin and 1% agarose (EAGLE's Medium, DMEM, Gibco Brl, Karlsruhe, Germany) in a 37° C. and 5% carbon dioxide incubator for 72 hours. After incubation, the result was stained with 0.5% (V/V) crystal violet to perform a plaque reduction assay.

The result of lung titer analysis showed that, among the PR8 virus-infected experimental groups, the trimer, monomer antigen and PCNA multivalent antigen mouse groups exhibited an average virus reduction of 0.2-0.4 log PFU/ml, compared to the control group not administered with the antigen (FIG. 13C, top). In particular, compared to the control group, the H1 HA-PCNA1dm, H1, H3, B HA trimer, monomer mixture, and multivalent antigen PCNAdm-3HA groups exhibited a decrease in lung titer of about 0.2-0.4 log PFU/ml. However, the SK bioscience trivalent mouse group showed a relatively small virus decrease of 0.09 log PFU/ml.

6-3: Animal Experiment Serum Assay 6-3-1: Plaque Reduction Neutralization Assay

The mouse serum sample was diluted at 1:10 and 1:40 and put in an Eppendorf tube, and each of PR8 (H1N1), Gy684 (H3N2), and FL04 (B) viruses was added at a ratio of 9:1 (v/v) to the diluted mouse serum sample, followed by performing reaction for 60 minutes. The reacted virus-diluted mouse serum sample was added to MDCK cells and infection was induced in a 37° C. and 5% carbon dioxide incubator for 60 minutes. The virus and the serum were removed, the cells were washed with DMEM, and incubated in a medium supplemented with a mixture (1:1) of DMEM and agarose containing 1 µg/ml TPCK trypsin in a 37° C. and 5% carbon dioxide incubator for 72 hours to form plaques. The plaques were fixed in 4% formaldehyde, stained with 0.5% crystal violet and then counted. The result of neutralization assay showed that, among experimental groups infected with the PR8 virus, the commercial SK bioscience trivalent vaccine group, H1 HA, H3 HA, B HA monomer mixture group, and the PCNADM-3H multivalent group exhibited a significant plaque reduction, compared to the control group, PBS buffer solution. For the H1N1 and H3N2 viruses, the commercial SK bioscience trivalent vaccine group and PCNADM-3HHA multivalent antigen group exhibited high neutralization activity and for the B-virus, the monomer mixture group and the PCNADM-3HA multivalent antigen group exhibited high neutralization activity, although there was a slight difference therebetween (FIG. 13C, bottom).

6-3-2: Mouse Serum Antibody Titer Assay

H1 HA and mini HA antigens were immobilized in the microplate, and serum antibody-antigen interaction was induced. Each group serum was used for primary antigen-antibody reaction and a secondary antibody conjugated with horseradish peroxidase was used. An antigen-antibody reaction was performed. 100 µl of TMB (3,3',5,5'-tetramethyl-benzidine, Sigma-Aldrich, St. Louis, MO) was added and the color was developed at room temperature for 10 minutes. Absorbance was measured at a wavelength of 450 nm through a microplate reader (Molecular Devices, Spectra-Max 190, Sunnyvale, CA). The H1 HA-PCNA1dM group and the PCNAdM-3HA multivalent antigen group had a high H1 HA antibody titer and the H1, H3, and B HA trimer group also had high antibody titers to the H1 HA trimer antigens (FIG. 13D). The H1, H3 and B HA trimer and monomer groups and the PCNAdM-3HA multivalent antigen group had a high B HA antibody titer and the SK bioscience trivalent vaccine group also had a high antibody titer to the B HA trimer. H1, H3 and B HA trimer mixture and PCNADM-3HA multivalent antigen groups had high antibody titers to H3 HA. Mini-HA (#4900 Construct-Stem HA) was used to measure titers of antibodies that specifically react with the stem region using mouse serum. The mini HA was immobilized, each group serum was used for antigen-antibody reactions, a secondary antibody and TMB were added to induce color development at room temperature, and the absorbance was measured at a wavelength of 450 nm. The PCNAdm-3HA multivalent antigen group and the H1 HA-PCNA1dm group had the highest antibody titer specific for the stem region (FIG. 13D, bottom right).

Example 7: Animal Experiment Using Multivalent Antigen PCNAdm-3HA Antigen: Passive Immunization 7-1: HA Mutant and Multivalent Antigen PCNAdm-3HA Antigen-Based Passive Immunization According to the passive immunization animal experiment scheme, HA monomer, HA-PCNAdm complex, PCNAdm-3HA multivalent antigen, and the like were inoculated into 5-week-old BALB/c mice by subcutaneous injection every 2 weeks. After 13 days, blood was collected and serum was isolated. The isolated serum was subjected to intraperitoneal injection into pre-acclimated 7-week-old mice. One day later, the mice were infected with the PR8 H1N1 subtype virus through intranasal administration (FIG. 14A). The respective groups are as follows. Group 1: naïve mice, Group 2: PBS buffer+adjuvant, Group 4: H1 HA monomer+adjuvant, Group 5: H1 HA-PCNA1+adjuvant, Group 6: SK bioscience commercial trivalent vaccine, and Group 9: PCNAdm-3HA+adjuvant. The group number was the same as the PR8 animal experiment group number and the vaccine efficacy was evaluated by measuring the changes in mouse weight and survival rate.

The result of passive immunization using antigen-induced immune serum showed that the PCNAdm-3HA multivalent antigen group and the H1 HA-PCNA1dm group had the lowest weight change and the highest survival rate, followed by the SK bioscience trivalent vaccine group and the H1 HA monomer group (FIG. 14B). Lung tissue virus concentration was decreased by 1.9 and 1.4 log PFU/ml in the PCNAdm-3HA multivalent antigen group and H1 HA-PCNA1dm group, respectively, and by 0.2-0.6 log PFU/ml in the SK bioscience trivalent vaccine group and H1 HA monomer group (FIG. 14C, top).

7-2: Serum Analysis

The results of the plaque test after reaction with H1N1, H3N2, and B viruses for 1 hour showed that the PCNAdm-3HA multivalent antigen group and the H1 HA-PCNA1dm group exhibited the highest neutralization antibody titers against H1, H3, and B HA antigens (FIG. 14C, middle, bottom). The results of ELISA using serum showed that the PCNAdm-3HA multivalent antigen group had the highest antibody titer to H1 HA, B HA, H3 HA, and mini HA (FIG. 14D). The H1 HA-PCNA1dm group, the SK bioscience trivalent vaccine group, and the H1 HA monomer group exhibited high antibody titers to the H1 HA antigen in a descending order. In particular, the PCNAdm-3HA multivalent antigen group, the H1 HA-PCNA1dm group, and the H1 HA monomer group exhibited high antibody titers to mini HA. This result suggests that the monomer is very effective in inducing stem-specific antibodies.

Example 8: Animal Test Using Multivalent Antigen PCNAdm-3HA Antigen: Group 2 X47 (H3N2) Virus Challenge 8-1: Multivalent Antigen PCNAdm—3HA Antigen-Based Animal Experiment The mouse animal experiment scheme was the same as the Group 1 PR8 (H1N1) virus challenge experiment, except that only the group classification was changed, that is, group 2 was infected with X47 (H3N2) virus, as shown below (FIG. 15A). Animal experiment groups were classified as follow: Group 1: naïve mice, Group 2: PBS buffer+adjuvant, Group 3: inactivated H3 X47+adjuvant, Group 4: SK bioscience commercial trivalent vaccine, Group 5: PCNA1-PCNA2-PCNA3 assembled+adjuvant, Group 6: H3 HA monomer+adjuvant, Group 7: H3 HA-PCNA3dm+adjuvant, Group 8: H1 HA, H3 HA, B HA mutant monomer mixture+adjuvant, and Group 9: multivalent antigen PCNAdm-3HA+adjuvant.

The result of the animal experiment showed that the inactivated X47 virus group showed the smallest weight change and high survival rate, and the PCNAdm-3HA multivalent antigen group and the H3 HA monomer group also exhibited a small body weight change and high survival rate (FIG. 15B), followed by the H3 HA-PCNA3dm group. The SK bioscience commercial trivalent vaccine group had little effect. The H1 HA monomer antigen group and the H1, H3, and B HA monomer mixture group exhibited a decrease in the body weight by 15% and recovered after 7 days, whereas the SK bioscience group showed a weight change of 20% or more on the $6^{th}$ day, resulting in a significant survival rate decrease. Like the Group 1 PR8 challenge animal experiment, the PCNAdm-3HA multivalent antigen group and the H3 HA monomer group exhibited high survival rates, whereas the commercially available SK bioscience trivalent vaccine group did not exhibit the survival rate comparable to the control PBS group. X47 (H3N2) virus is a mouse-adapted virus produced by a reassortant from A/Victorial/3/75 (H3N2) and A/PR/8/34 (H1N1) viruses that were propagated in fertilized eggs. Therefore, the X47 (H3N2) virus possesses the 1970s virus HA epitope, which indicates that the SK bioscience vaccine having the seasonal virus H3 HA epitope since 2010 or the PCNAdm-3HA multivalent antigen and H3 HA monomer antigens having the H3 HA epitope derived from the A/Gyeongnam/684/2006 virus are considered to be the cause of decreased immune activity. Nevertheless, it is noteworthy that the PCNAdm-3HA group and the H3 HA-PCNA3dm monomer group had significantly higher survival rates compared to the commercial SK bioscience trivalent vaccine group and were capable of effectively inducing the stem-specific antibody.

8-2: Mouse Lung Tissue Virus and Serum Assay

The virus was extracted from the lung tissue on the 4$^{th}$ day after infection, MDCK (Madin-Darby canine kidney) cells were infected therewith, and the virus concentration (titer) was calculated by a plaque reduction assay. In the X47 (H3N2) experiment, the inactivated X47 virus group exhibited about 2 log virus reduction compared to the control PBS buffer group, and the PCNAdm-3HA multivalent antigen group, H3 HA monomer and H3 HA-PCNA3dm group exhibited 1.2-1.5 log virus reduction (FIG. 15C, top). Next, the monomer mixture group exhibited a difference of 0.8 log. In contrast, the commercial SK bioscience trivalent vaccine group did not exhibit a decrease in virus titer and was the same as the control PBS buffer group.

The result of the serum antibody titer detected using ELISA showed that the PCNAdm-3HA multivalent antigen, H3 HA monomer, H3 HA-PCNA3dm and H1, H3, B HA monomer mixture groups exhibited relatively high antibody titers, whereas the SK bioscience commercial vaccine group exhibited lower titers of antibodies to the H3 HA trimer antigen (FIG. 15C, bottom). A noteworthy point is that the inactivated X47 virus group exhibited the low antibody titer compared to the survival rate because the antigen used in the ELISA was the H3 HA antigen derived from the recent influenza virus strain, not the 1970s' virus. The high survival rate of the H3 HA monomer and PCNAdm-3HA antigen is considered a very meaningful result from the viewpoint that the X47 epitope is greatly different from the epitope of the used H3 HA antigen. More importantly, the PCNAdm-3HA multivalent antigen group exhibited the highest antibody titer to the mini HA antigen. This is significantly consistent with the results of PR8 (H1N1) animal experiments, which indicates that the PCNAdm-3HA multivalent antigen group is very effective in inducing stem-specific antibodies. Although antibody titers have been tested to date depending on HA head region-specific antibody or hemagglutination inhibitory reaction, stem region-specific antibody and antibody-dependent cell-mediated cytotoxicity (ADCC) virus control mechanisms have recently been developed and the importance of stem-specific antibodies has been highlighted. Although the monomer induces stem-specific antibodies relatively better than the trimer, it is noteworthy that the PCNA-bound monomeric form, particularly the PCNAdm-3HA multivalent antigen, increased the stem-specific antibody titers.

In conclusion, it was found that the HA monomer, HA-PCNAdm, and PCNAdm-3HA multivalent antigen used in the present invention exhibit virus reduction, antibody titers induced in serum and immune activity comparable or superior to conventional commercial trivalent vaccines. It is considered that the antigen composition of the present invention is highly applicable to Group 1 and 2 virus infections.

EXPLANATION OF REFERENCE NUMERALS

100: First fusion protein 110: First scaffold fragment
120: First recombinant antigen protein 200: Second fusion protein
210: Second scaffold fragment 220: Second recombinant antigen protein
300: Third fusion protein 310: Third scaffold fragment
320: Third recombinant antigen protein Although specific configurations of the present invention have been described in detail, those skilled in the art will appreciate that this detailed description is provided as preferred embodiments for illustrative purposes and should not be construed as limiting the scope of the present invention. Therefore, the substantial scope of the present invention is defined by the accompanying filed claims and equivalents thereto.

INDUSTRIAL APPLICABILITY

The antigen composition for preventing or treating viral infectious diseases according to the present invention is highly effective in inhibiting the proliferation and replication of viruses having various subtypes and mutations, and is considered to have recyclability and safety due to the use of recombinant proteins and is thus widely used in a variety of industrial fields such as pharmaceuticals, life science and the like.

The invention claimed is:

1. An antigen composition for preventing or treating viral infectious diseases comprising, as an active ingredient, an influenza virus recombinant hemagglutinin monomeric protein represented by any one of SEQ ID NO: 1 to SEQ ID NO: 3.

2. The antigen composition according to claim 1, wherein the influenza virus recombinant hemagglutinin monomeric protein represented by SEQ ID NO: 1 is H1 subtype influenza virus recombinant hemagglutinin having five protein mutations and two disulfide bond mutations, the influenza virus recombinant hemagglutinin monomeric protein represented by SEQ ID NO: 2 is influenza B virus recombinant hemagglutinin having eight protein mutations, and the influenza virus recombinant hemagglutinin monomeric protein represented by SEQ ID NO: 3 is H3 subtype influenza virus recombinant hemagglutinin having five protein mutations and one disulfide bond mutation.

3. The antigen composition according to claim 1, wherein the influenza virus recombinant hemagglutinin monomeric protein has a preventive or therapeutic effect on animal and human influenza by inhibiting proliferation and replication of orthomyxovirus.

4. The antigen composition according to claim 1, wherein the influenza virus recombinant hemagglutinin monomeric protein is present in an amount of 0.001% to 99.9% by weight in the antigen composition.

5. An antigen composition for preventing or treating viral infectious diseases comprising one or more fusion proteins, each comprising a scaffold fragment and a recombinant antigen protein bound to the scaffold fragment, wherein the fusion proteins are present in plural and are different from each other, respective scaffold fragments of the fusion proteins are self-assembled to form a cyclic scaffold, and a recombinant antigen protein is exposed to the outside of the cyclic scaffold, wherein the fusion proteins are present in plural and are different from each other, respective scaffold fragments of the fusion proteins are self-assembled to form a cyclic scaffold, and a recombinant antigen protein is exposed to the outside of the cyclic scaffold, and wherein a first fusion protein, which is any one of the plurality of fusion proteins, comprises a first scaffold fragment represented by SEQ ID NO: 4 and a first recombinant antigen protein bound to the first scaffold fragment and represented by SEQ ID NO: 1.

6. The antigen composition according to claim 5, wherein a second fusion protein, which is any one of the plurality of fusion proteins, comprises a second scaffold fragment represented by SEQ ID NO: 5 and a second recombinant antigen protein bound to the second scaffold fragment and represented by SEQ ID NO: 2.

7. The antigen composition according to claim 5, wherein a third fusion protein, which is any one of the plurality of fusion proteins, comprises a third scaffold fragment represented by SEQ ID NO: 6 and a third recombinant antigen protein bound to the third scaffold fragment and represented by SEQ ID NO: 3.

8. The antigen composition according to claim 5, wherein the second fusion protein, which is any one of the plurality of fusion proteins, comprises a second scaffold fragment represented by SEQ ID NO: 5 and a second recombinant antigen protein bound to the second scaffold fragment and represented by SEQ ID NO: 2, and a third fusion protein, which is any one of the plurality of fusion proteins, comprises a third scaffold fragment represented by SEQ ID NO: 6 and a third recombinant antigen protein bound to the third scaffold fragment and represented by SEQ ID NO: 3.

9. The antigen composition according to claim 5, wherein the scaffold fragment is a proliferating cell nuclear antigen (PCNA).

10. The antigen composition according to claim 5, wherein the recombinant antigen protein is an influenza virus recombinant hemagglutinin monomeric mutant protein.

11. The antigen composition according to claim 5, wherein the virus is selected from the group consisting of Orthomyxoviridae including influenza virus, transmissible gastroenteritis virus, porcine epidemic diarrhea (PED) virus, SARS, MERS, coronavirus including SARS-COV-2, Zika virus, Flavivirus including bovine viral diarrhea (BVD) virus, Calicivirus including norovirus, respiratory syncytial virus (RSV), porcine respiratory reproductive syndrome (PRRS) virus, porcine circovirus type 2 (PCV2) virus, rotavirus, parvovirus, picornavirus, pestivirus, rhabdovirus, birnavirus, retroviruses and herpesvirus.

12. The antigen composition according to claim 5, wherein the fusion protein is present in an amount of 0.001% to 99.9% by weight.

* * * * *

SEQUENCE LISTING

```
<160> NUMBER OF SEQ ID NOS: 6

<210> SEQ ID NO 1
<211> LENGTH: 618
<212> TYPE: PRT
<213> ORGANISM: Artificial Sequence
<220> FEATURE:
<223> OTHER INFORMATION: multiple mutant protein(H1 HA_5m_2DS)

<400> SEQUENCE: 1

Met Ser Tyr Tyr His His His His His His Asp Tyr Asp Ile Pro Thr
1               5                   10                  15
```

```
Thr Glu Asn Leu Tyr Phe Gln Gly Ala Met Asp Met Leu Leu Val Asn
            20                  25                  30

Gln Ser His Gln Gly Phe Asn Lys Glu His Thr Ser Lys Met Val Ser
            35                  40                  45

Ala Ile Val Leu Tyr Val Leu Leu Ala Ala Ala Ala His Ser Ala Phe
    50                  55                  60

Ala Ala Asp Pro Gly Asp Thr Leu Cys Ile Gly Tyr His Ala Asn Asn
65                  70                  75                  80

Ser Thr Asp Thr Val Asp Thr Cys Leu Glu Lys Asn Val Thr Val Thr
                85                  90                  95

His Ser Val Asn Leu Leu Glu Asp Lys His Asn Gly Lys Leu Cys Lys
            100                 105                 110

Leu Arg Gly Val Ala Pro Leu His Leu Gly Lys Cys Asn Ile Ala Gly
            115                 120                 125

Trp Ile Leu Gly Asn Pro Glu Cys Glu Ser Leu Ser Thr Ala Ser Ser
    130                 135                 140

Trp Ser Tyr Ile Val Glu Thr Pro Ser Ser Asp Asn Gly Thr Cys Tyr
145                 150                 155                 160

Pro Gly Asp Phe Ile Asp Tyr Glu Glu Leu Arg Glu Gln Leu Ser Ser
                165                 170                 175

Val Ser Ser Phe Glu Arg Phe Glu Ile Phe Pro Lys Thr Ser Ser Trp
            180                 185                 190

Pro Asn His Asp Ser Asn Lys Gly Val Thr Ala Ala Cys Pro His Ala
            195                 200                 205

Gly Ala Lys Ser Phe Tyr Lys Asn Leu Ile Trp Leu Val Lys Lys Gly
    210                 215                 220

Asn Ser Tyr Pro Lys Leu Ser Lys Ser Tyr Ile Asn Asp Lys Gly Lys
225                 230                 235                 240

Glu Val Leu Val Leu Trp Gly Ile His His Pro Ser Thr Ser Ala Asp
                245                 250                 255

Gln Gln Ser Leu Tyr Gln Asn Ala Asp Ala Tyr Val Phe Val Gly Ser
            260                 265                 270

Ser Arg Tyr Ser Lys Lys Phe Lys Pro Glu Ile Ala Ile Arg Pro Lys
            275                 280                 285

Val Arg Asp Gln Glu Gly Arg Met Asn Tyr Tyr Trp Thr Leu Val Glu
    290                 295                 300

Pro Gly Asp Lys Ile Thr Phe Glu Ala Thr Gly Asn Leu Val Val Pro
305                 310                 315                 320

Arg Tyr Ala Phe Ala Met Glu Arg Asn Ala Gly Ser Gly Ile Ile Ile
                325                 330                 335

Ser Asp Thr Pro Val His Asp Cys Asn Thr Thr Cys Gln Thr Pro Lys
            340                 345                 350

Gly Ala Ile Asn Thr Ser Leu Pro Phe Gln Asn Ile His Pro Ile Thr
            355                 360                 365

Ile Gly Lys Cys Pro Lys Tyr Val Lys Ser Thr Lys Leu Arg Leu Ala
    370                 375                 380

Thr Gly Cys Arg Asn Ile Pro Ser Ile Gln Ser Arg Gly Leu Phe Gly
385                 390                 395                 400

Ala Ile Ala Gly Phe Ile Glu Gly Gly Trp Thr Gly Met Val Asp Gly
                405                 410                 415

Trp Tyr Gly Tyr His His Gln Asn Glu Gln Gly Ser Gly Tyr Ala Ala
            420                 425                 430

Asp Leu Lys Ser Thr Gln Asn Ala Ile Asp Glu Ile Thr Asn Lys Val
```

-continued

---

```
            435                 440                 445
Asn Ser Val Ile Glu Lys Met Asn Thr Gln Phe Thr Ala Val Gly Lys
    450                 455                 460

Glu Phe Asn His Ser Glu Lys Arg Ser Glu Asn Ser Asn Lys Lys Val
465                 470                 475                 480

Asp Asp Gly Glu Leu Asp Trp Trp Thr Tyr Asn Ala Glu Leu Leu Val
                485                 490                 495

Leu Leu Glu Asn Cys Arg Thr Leu Asp Tyr Cys Asp Ser Asn Val Lys
                500                 505                 510

Asn Leu Tyr Glu Lys Val Arg Ser Gln Leu Lys Asn Asn Ala Lys Glu
                515                 520                 525

Ile Gly Asn Gly Cys Phe Glu Phe Tyr His Lys Cys Asp Asn Thr Cys
    530                 535                 540

Met Glu Ser Val Lys Asn Gly Thr Tyr Asp Tyr Pro Lys Tyr Ser Glu
545                 550                 555                 560

Glu Ala Lys Leu Asn Arg Glu Glu Ile Asp Gly Val Ser Gly Arg Leu
                565                 570                 575

Val Pro Arg Gly Ser Pro Gly Ser Gly Tyr Ile Pro Glu Ala Pro Arg
                580                 585                 590

Asp Gly Gln Ala Tyr Val Arg Lys Asp Gly Glu Trp Val Leu Leu Ser
                595                 600                 605

Thr Phe Leu Gly His His His His His His
    610                 615

<210> SEQ ID NO 2
<211> LENGTH: 641
<212> TYPE: PRT
<213> ORGANISM: Artificial Sequence
<220> FEATURE:
<223> OTHER INFORMATION: multiple mutant protein(B HA_8m)

<400> SEQUENCE: 2

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
                20                  25                  30

Leu Met Leu Leu Val Asn Gln Ser His Gln Gly Phe Asn Lys Glu His
        35                  40                  45

Thr Ser Lys Met Val Ser Ala Ile Val Leu Tyr Val Leu Leu Ala Ala
    50                  55                  60

Ala Ala His Ser Ala Phe Ala Ala Asp Pro Gly Tyr Leu Leu Glu Phe
65                  70                  75                  80

Asp Arg Ile Cys Thr Gly Ile Thr Ser Ser Asn Ser Pro His Val Val
                85                  90                  95

Lys Thr Ala Thr Gln Gly Glu Val Asn Val Thr Gly Val Ile Pro Leu
            100                 105                 110

Thr Thr Thr Pro Thr Lys Ser Tyr Phe Ala Asn Leu Lys Gly Thr Arg
            115                 120                 125

Thr Arg Gly Lys Leu Cys Pro Asp Cys Leu Asn Cys Thr Asp Leu Asp
    130                 135                 140

Val Ala Leu Gly Arg Pro Met Cys Val Gly Thr Thr Pro Ser Ala Lys
145                 150                 155                 160

Ala Ser Ile Leu His Glu Val Arg Pro Val Thr Ser Gly Cys Phe Pro
                165                 170                 175

Ile Met His Asp Arg Thr Lys Ile Arg Gln Leu Pro Asn Leu Leu Arg
```

-continued

```
                180                 185                 190
Gly Tyr Glu Asn Ile Arg Leu Ser Thr Gln Asn Val Ile Asp Ala Glu
            195                 200                 205

Lys Ala Pro Gly Gly Pro Tyr Arg Leu Gly Thr Ser Gly Ser Cys Pro
        210                 215                 220

Asn Ala Thr Ser Lys Ile Gly Phe Phe Ala Thr Met Ala Trp Ala Val
225                 230                 235                 240

Pro Lys Asp Asn Tyr Lys Asn Ala Thr Asn Pro Leu Thr Val Glu Val
                245                 250                 255

Pro Tyr Ile Cys Thr Glu Gly Glu Asp Gln Ile Thr Val Trp Gly Phe
            260                 265                 270

His Ser Asp Asn Lys Thr Gln Met Lys Asn Leu Tyr Gly Asp Ser Asn
        275                 280                 285

Pro Gln Lys Phe Thr Ser Ser Ala Asn Gly Val Thr Thr His Tyr Val
    290                 295                 300

Ser Gln Ile Gly Asp Phe Pro Asp Gln Thr Glu Asp Gly Gly Leu Pro
305                 310                 315                 320

Gln Ser Gly Arg Ile Val Val Asp Tyr Met Met Gln Lys Pro Gly Lys
                325                 330                 335

Thr Gly Thr Ile Val Tyr Gln Arg Gly Val Leu Leu Pro Gln Lys Val
            340                 345                 350

Trp Cys Ala Ser Gly Arg Ser Lys Val Ile Lys Gly Ser Leu Pro Leu
        355                 360                 365

Ile Gly Glu Ala Asp Cys Leu His Glu Lys Tyr Gly Gly Leu Asn Lys
    370                 375                 380

Ser Lys Pro Tyr Tyr Thr Gly Glu His Ala Lys Ala Ile Gly Asn Cys
385                 390                 395                 400

Pro Ile Trp Val Lys Thr Pro Leu Lys Leu Ala Asn Gly Thr Lys Tyr
                405                 410                 415

Arg Pro Pro Ala Lys Leu Leu Lys Glu Arg Gly Phe Phe Gly Ala Ile
            420                 425                 430

Ala Gly Phe Leu Glu Gly Gly Trp Glu Gly Met Ile Ala Gly Trp His
        435                 440                 445

Gly Tyr Thr Ser His Gly Ala His Gly Val Ala Val Ala Ala Asp Leu
    450                 455                 460

Lys Ser Thr Gln Glu Ala Ile Asn Lys Ile Thr Lys Asn Leu Asn Ser
465                 470                 475                 480

Leu Ser Glu Leu Glu Val Lys Asn Leu Gln Arg Leu Ser Gly Ala Met
                485                 490                 495

Asp Glu Ser His Asn Glu Ser Leu Glu Trp Asp Glu Lys Trp Asp Asp
            500                 505                 510

Ser Arg Ala Asp Trp Ile Ser Ser Gln Ile Glu Ser Ala Val Leu Trp
        515                 520                 525

Ser Asn Glu Gly Ile Ile Asn Ser Glu Asp Glu His Leu Leu Ala Leu
    530                 535                 540

Glu Arg Lys Leu Lys Lys Met Leu Gly Pro Ser Ala Val Asp Ile Gly
545                 550                 555                 560

Asn Gly Cys Phe Glu Thr Lys His Lys Cys Asn Gln Thr Cys Leu Asp
                565                 570                 575

Arg Ile Ala Ala Gly Thr Phe Asn Ala Gly Glu Phe Ser Leu Pro Thr
            580                 585                 590

Phe Asp Ser Ser Gly Arg Leu Val Pro Arg Gly Ser Pro Gly Ser Gly
        595                 600                 605
```

-continued

Tyr Ile Pro Glu Ala Pro Arg Asp Gly Gln Ala Tyr Val Arg Lys Asp
    610             615             620

Gly Glu Trp Val Leu Leu Ser Thr Phe Leu Gly His His His His His
625             630             635             640

His

<210> SEQ ID NO 3
<211> LENGTH: 610
<212> TYPE: PRT
<213> ORGANISM: Artificial Sequence
<220> FEATURE:
<223> OTHER INFORMATION: multiple mutant protein(H3 HA_5m_DS)

<400> SEQUENCE: 3

Met Ser Tyr Tyr His His His His His His Asp Tyr Asp Ile Pro Thr
1               5               10              15

Thr Glu Asn Leu Tyr Phe Gln Gly Ala Met Asp Met Leu Leu Val Asn
                20              25              30

Gln Ser His Gln Gly Phe Asn Lys Glu His Thr Ser Lys Met Val Ser
        35              40              45

Ala Ile Val Leu Tyr Val Leu Leu Ala Ala Ala Ala His Ser Ala Phe
    50              55              60

Ala Ala Asp Pro Gly Ala Thr Leu Cys Leu Gly His His Ala Val Gln
65              70              75              80

Asn Gly Thr Ile Val Lys Thr Ile Thr Asn Asp Gln Ile Glu Val Thr
                85              90              95

Asn Ala Thr Glu Leu Val Gln Asn Ser Ser Thr Gly Gly Ile Cys Asp
            100             105             110

Ser Pro His Gln Ile Leu Asp Gly Glu Asn Cys Thr Leu Ile Asp Ala
        115             120             125

Leu Leu Gly Asp Pro Gln Cys Asp Gly Phe Gln Asn Lys Lys Trp Asp
    130             135             140

Leu Phe Val Glu Arg Ser Lys Ala Tyr Ser Asn Cys Tyr Pro Tyr Asp
145             150             155             160

Val Pro Asp Tyr Ala Ser Leu Arg Ser Leu Val Ala Ser Ser Gly Thr
                165             170             175

Leu Glu Phe Asn Asn Glu Ser Phe Asn Trp Thr Gly Val Thr Gln Asn
            180             185             190

Gly Thr Ser Ser Ala Cys Lys Arg Gly Ser Asn Asn Ser Phe Phe Ser
        195             200             205

Arg Leu Asn Trp Leu Thr His Ser Lys Phe Lys Tyr Pro Ala Leu Asn
    210             215             220

Val Thr Met Pro Asn Asn Glu Glu Phe Asp Lys Leu Tyr Ile Trp Gly
225             230             235             240

Val His His Pro Gly Thr Asp Asn Asp Gln Ile Phe Leu Tyr Ala Gln
                245             250             255

Ala Ser Gly Arg Ile Thr Val Ser Thr Lys Arg Ser Gln Gln Thr Val
            260             265             270

Ile Pro Asn Ile Gly Ser Arg Pro Arg Val Arg Asp Ile Pro Ser Arg
        275             280             285

Ile Ser Ile Tyr Trp Thr Ile Val Lys Pro Gly Asp Ile Leu Leu Ile
    290             295             300

Asn Ser Thr Gly Asn Leu Ile Ala Pro Arg Gly Tyr Phe Lys Ile Arg
305             310             315             320

-continued

```
Ser Gly Lys Ser Ser Ile Met Arg Ser Asp Ala Pro Ile Gly Lys Cys
            325                 330                 335

Asn Ser Glu Cys Ile Thr Pro Asn Gly Ser Ile Pro Asn Asp Lys Pro
            340                 345                 350

Phe Gln Asn Val Asn Arg Ile Thr Tyr Gly Ala Cys Pro Arg Tyr Val
            355                 360                 365

Lys Gln Asn Thr Leu Lys Leu Ala Thr Gly Cys Arg Asn Val Pro Glu
        370                 375                 380

Lys Gln Thr Arg Gly Ile Phe Gly Ala Ile Ala Gly Phe Ile Glu Asn
385                 390                 395                 400

Gly Trp Glu Gly Met Val Asp Gly Trp Tyr Gly Phe Arg His Gln Asn
                405                 410                 415

Ser Glu Gly Ile Gly Gln Ala Ala Asp Leu Lys Ser Thr Gln Ala Ala
            420                 425                 430

Ile Asp Gln Ile Asn Gly Lys Leu Asn Arg Leu Ile Gly Lys Thr Asn
            435                 440                 445

Glu Lys Phe His Gln Ile Glu Lys Glu Phe Ser Glu Ser Glu Gly Arg
        450                 455                 460

Ser Gln Asp Ser Glu Lys Tyr Trp Glu Asp Thr Lys Ile Asp Trp Trp
465                 470                 475                 480

Ser Tyr Asn Ala Glu Leu Leu Val Ala Leu Glu Asn Gln His Thr Ile
                485                 490                 495

Asp Leu Cys Asp Ser Glu Met Asn Lys Leu Phe Glu Lys Thr Lys Lys
            500                 505                 510

Gln Leu Arg Glu Asn Ala Glu Asp Met Gly Asn Gly Cys Phe Lys Ile
            515                 520                 525

Tyr His Lys Cys Asp Asn Ala Cys Ile Gly Ser Ile Arg Asn Gly Thr
        530                 535                 540

Tyr Asp His Asp Val Tyr Arg Asp Glu Ala Leu Asn Asn Arg Phe Gln
545                 550                 555                 560

Ile Lys Gly Leu Ser Gly Arg Leu Val Pro Arg Gly Ser Pro Gly Ser
                565                 570                 575

Gly Tyr Ile Pro Glu Ala Pro Arg Asp Gly Gln Ala Tyr Val Arg Lys
            580                 585                 590

Asp Gly Glu Trp Val Leu Leu Ser Thr Phe Leu Gly His His His His
        595                 600                 605

His His
    610
```

```
<210> SEQ ID NO 4
<211> LENGTH: 249
<212> TYPE: PRT
<213> ORGANISM: Artificial Sequence
<220> FEATURE:
<223> OTHER INFORMATION: PCNA1dm

<400> SEQUENCE: 4

Met Phe Lys Ile Val Tyr Pro Asn Ala Lys Asp Phe Phe Ser Phe Ile
1               5                   10                  15

Asn Ser Ile Thr Asn Val Thr Asp Ser Ile Ile Leu Asn Phe Thr Glu
                20                  25                  30

Asp Gly Ile Phe Ser Arg His Leu Thr Glu Asp Lys Val Leu Met Ala
            35                  40                  45

Ile Met Arg Ile Pro Lys Asp Val Leu Ser Glu Tyr Ser Ile Asp Ser
        50                  55                  60
```

-continued

```
Pro Thr Ser Val Lys Leu Asp Val Ser Ser Val Lys Lys Ile Leu Ser
65              70                  75                  80

Lys Ala Ser Ser Lys Lys Ala Thr Ile Glu Leu Thr Glu Thr Asp Ser
                85                  90                  95

Gly Leu Lys Ile Ile Ile Arg Asp Glu Lys Ser Gly Ala Lys Ser Lys
            100                 105                 110

Ile Lys Ile Lys Ala Glu Lys Gly Gln Val Glu Gln Leu Thr Glu Pro
        115                 120                 125

Lys Val Asn Leu Ala Val Asn Phe Thr Thr Asp Glu Ser Val Leu Asn
    130                 135                 140

Val Ile Ala Ala Asp Val Thr Leu Val Gly Glu Glu Met Arg Ile Ser
145                 150                 155                 160

Thr Glu Glu Asp Lys Ile Lys Ile Glu Ala Gly Glu Glu Gly Lys Arg
                165                 170                 175

Tyr Val Ala Phe Leu Met Lys Asp Lys Pro Leu Lys Glu Leu Ser Ile
            180                 185                 190

Asp Thr Ser Ala Ser Ser Ser Tyr Ser Ala Glu Met Phe Lys Asp Ala
        195                 200                 205

Val Lys Gly Leu Arg Gly Phe Ser Ala Pro Thr Met Val Ser Phe Gly
    210                 215                 220

Glu Asn Leu Pro Met Lys Ile Asp Val Glu Ala Val Ser Gly Gly His
225                 230                 235                 240

Met Ile Phe Trp Ile Ala Pro Arg Leu
                245
```

```
<210> SEQ ID NO 5
<211> LENGTH: 266
<212> TYPE: PRT
<213> ORGANISM: Artificial Sequence
<220> FEATURE:
<223> OTHER INFORMATION: PCNA2dm

<400> SEQUENCE: 5

Met Gly Ser Ser His His His His His His Ser Ser Gly Leu Val Pro
1               5                   10                  15

Arg Gly Ser His Met Met Lys Ala Lys Val Ile Asp Ala Val Ser Phe
            20                  25                  30

Ser Tyr Ile Leu Arg Thr Val Gly Asp Phe Leu Ser Glu Ala Asn Phe
        35                  40                  45

Ile Val Thr Lys Glu Gly Ile Arg Val Ser Gly Ile Asp Pro Ser Arg
    50                  55                  60

Val Val Phe Leu Asp Ile Phe Leu Pro Ser Ser Tyr Phe Glu Gly Phe
65              70                  75                  80

Glu Val Ser Gln Glu Lys Glu Ile Ile Gly Phe Lys Leu Glu Asp Val
                85                  90                  95

Asn Asp Ile Leu Lys Arg Val Leu Lys Asp Asp Thr Leu Ile Leu Ser
            100                 105                 110

Ser Asn Glu Ser Lys Leu Thr Leu Thr Phe Asp Gly Glu Phe Thr Arg
        115                 120                 125

Ser Phe Glu Leu Pro Leu Ile Gln Val Glu Ser Thr Gln Pro Pro Ser
    130                 135                 140

Val Asn Leu Glu Phe Pro Phe Lys Ala Gln Leu Leu Thr Ile Thr Phe
145                 150                 155                 160

Ala Asp Ile Ile Asp Glu Leu Ser Asp Leu Gly Glu Val Leu Asn Ile
                165                 170                 175
```

-continued

```
His Ser Lys Glu Asn Lys Leu Tyr Phe Glu Val Ile Gly Asp Leu Val
            180                 185                 190

Thr Val Lys Val Glu Leu Ser Thr Asp Asn Gly Thr Leu Leu Glu Ala
            195                 200                 205

Ser Gly Ala Asp Val Ser Ser Ser Tyr Gly Met Glu Tyr Val Ala Asn
            210                 215                 220

Thr Thr Lys Met Arg Arg Ala Ser Asp Ser Met Glu Leu Tyr Phe Gly
225                 230                 235                 240

Ser Gln Ile Pro Leu Lys Leu Arg Phe Lys Leu Pro Gln Glu Gly Tyr
            245                 250                 255

Gly Asp Phe Tyr Ile Ala Pro Arg Ala Asp
            260                 265

<210> SEQ ID NO 6
<211> LENGTH: 273
<212> TYPE: PRT
<213> ORGANISM: Artificial Sequence
<220> FEATURE:
<223> OTHER INFORMATION: PCNA3dm

<400> SEQUENCE: 6

Met Gly Ser Ser His His His His His His Ser Gln Asp Pro Met Ile
1               5                   10                  15

Tyr Leu Lys Ser Phe Glu Arg Asn Ile Arg Leu Ile Asn Met Lys Val
            20                  25                  30

Val Tyr Asp Asp Val Arg Val Leu Lys Asp Ile Ile Gln Ala Leu Ala
            35                  40                  45

Arg Leu Val Asp Glu Ala Val Leu Lys Phe Lys Gln Asp Ser Val Glu
            50                  55                  60

Leu Val Ala Leu Asp Arg Ala His Ile Ser Leu Ile Ser Val Asn Leu
65                  70                  75                  80

Pro Arg Glu Met Phe Lys Glu Tyr Asp Val Asn Asp Glu Phe Lys Phe
                85                  90                  95

Gly Phe Asn Thr Gln Phe Leu Met Lys Ile Leu Lys Val Ala Lys Arg
            100                 105                 110

Lys Glu Ala Ile Glu Ile Ala Ser Glu Ser Pro Asp Ser Val Ile Ile
            115                 120                 125

Asn Ile Ile Gly Ser Thr Asn Arg Glu Phe Asn Val Arg Asn Leu Glu
            130                 135                 140

Val Ser Glu Gln Glu Ile Pro Glu Ile Asn Leu Gln Phe Asp Ile Ser
145                 150                 155                 160

Ala Thr Ile Ser Ser Asp Gly Phe Lys Ser Ala Ile Ser Glu Val Ser
                165                 170                 175

Thr Val Thr Asp Asn Val Val Val Glu Gly His Glu Asp Arg Ile Leu
            180                 185                 190

Ile Lys Ala Glu Gly Glu Val Glu Val Glu Val Glu Phe Ser Lys Asp
            195                 200                 205

Thr Gly Gly Leu Gln Asp Leu Glu Phe Ser Lys Glu Ser Lys Asn Ser
            210                 215                 220
```

-continued

```
Tyr Ser Ala Glu Tyr Leu Asp Asp Val Leu Ser Leu Thr Lys Leu Ser
225             230                 235                 240

Asp Tyr Val Lys Ile Ser Phe Gly Asn Gln Lys Pro Leu Gln Leu Phe
                245                 250                 255

Phe Asn Met Glu Gly Gly Gly Lys Val Thr Tyr Leu Leu Ala Pro Lys
            260                 265                 270

Val
```